(12) United States Patent
Matsumura et al.

(10) Patent No.: US 9,128,056 B2
(45) Date of Patent: Sep. 8, 2015

(54) SAMPLE HOLDING CARRIER, AND FLUORESCENCE DETECTION SYSTEM AND FLUORESCENCE DETECTION DEVICE THAT USE SAME

(71) Applicants: PANASONIC CORPORATION, Osaka (JP); SANYO Electric Co., Ltd., Osaka (JP)

(72) Inventors: Yoshiyuki Matsumura, Osaka (JP); Kenji Nagatomi, Osaka (JP); Masaya Nakatani, Hyogo (JP); Akio Oki, Kyoto (JP); Morio Nakatani, Miyagi (JP); Takuya Hayashi, Kyoto (JP); Masaaki Hayama, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 14/498,877

(22) Filed: Sep. 26, 2014

(65) Prior Publication Data

US 2015/0048256 A1 Feb. 19, 2015

Related U.S. Application Data

(63) Continuation of application No. PCT/JP2013/057462, filed on Mar. 15, 2013.

(30) Foreign Application Priority Data

Mar. 29, 2012 (JP) ................................. 2012-077896
Mar. 29, 2012 (JP) ................................. 2012-077902

(51) Int. Cl.
*G01J 1/58* (2006.01)
*G01N 21/64* (2006.01)
(Continued)

(52) U.S. Cl.
CPC ............ *G01N 21/645* (2013.01); *B01L 3/5085* (2013.01); *G01N 21/03* (2013.01);
(Continued)

(58) Field of Classification Search
CPC .......... G01N 21/645; G01N 35/00069; G01N 21/03; G01N 21/6447; G01N 21/6452; B01L 3/5085; B01L 2300/024; B01L 2300/0803; B01L 2300/168; B01L 2300/0806; B01L 2300/0819; G11B 7/00; G11B 7/09
USPC ........ 250/458.1, 459.1, 461.1, 461.2, 440.11, 250/442.11, 453.11
See application file for complete search history.

(56) References Cited

U.S. PATENT DOCUMENTS 5,892,577 A 4/1999 Gordon
6,071,702 A 6/2000 Yamamoto et al.
(Continued)

FOREIGN PATENT DOCUMENTS

DE 10112455 2/2002
EP 1510819 3/2005
(Continued)

OTHER PUBLICATIONS

International Search Report issued in International Application No. PCT/JP2013/057462 with Date of mailing Jun. 18, 2013, with English Translation.
(Continued)

*Primary Examiner* — Michael Maskell
(74) *Attorney, Agent, or Firm* — McDermott Will & Emery LLP

(57) ABSTRACT

The present invention provides a sample holding carrier that can accurately measure a sample with a simple configuration, and a fluorescence detection system and device that use the same. Biosensor substrate includes: base substrate on which excitation light is incident from a lower surface; reflecting film that is arranged on an upper surface of base substrate to partially reflect the excitation light; and plural wells that are arranged on an upper surface side of reflecting film and have bottom surface portions. The excitation light is converged to be incident on base substrate. Distance from reflecting surface that is of a boundary between reflecting film and base substrate to bottom surface portion of well is less than or equal to a focal depth of the excitation light. Therefore, the sample accommodated in bottom surface portion of well can surely and efficiently be irradiated with the excitation light, and accurately be measured.

13 Claims, 31 Drawing Sheets

(51) Int. Cl.
  *G01N 21/03* (2006.01)
  *G01N 35/00* (2006.01)
  *G11B 7/00* (2006.01)
  *G11B 7/09* (2006.01)
  *B01L 3/00* (2006.01)

(52) U.S. Cl.
  CPC ........ *G01N21/6447* (2013.01); *G01N 21/6452* (2013.01); *G01N 35/00069* (2013.01); *G11B 7/00* (2013.01); *G11B 7/09* (2013.01); *B01L 2300/024* (2013.01); *B01L 2300/0654* (2013.01); *B01L 2300/0803* (2013.01); *B01L 2300/0806* (2013.01); *B01L 2300/0819* (2013.01); *B01L 2300/0893* (2013.01); *B01L 2300/168* (2013.01); *G01N 2021/6463* (2013.01); *G01N 2021/6482* (2013.01); *G01N 2201/105* (2013.01)

(56) References Cited

U.S. PATENT DOCUMENTS

| | | | |
|---|---|---|---|
| 6,563,584 | B1 | 5/2003 | Yurino et al. |
| 7,285,789 | B2 * | 10/2007 | Wiki et al. ............... 250/453.11 |
| 7,466,408 | B2 * | 12/2008 | Tanaami ........................ 356/317 |
| 2001/0055114 | A1 | 12/2001 | Suzuki et al. |
| 2002/0139936 | A1 * | 10/2002 | Dumas ....................... 250/458.1 |
| 2003/0133840 | A1 | 7/2003 | Coombs et al. |
| 2004/0021867 | A1 | 2/2004 | Karthe et al. |
| 2005/0264805 | A1 | 12/2005 | Cromwell et al. |
| 2006/0275181 | A1 | 12/2006 | Takeda et al. |
| 2007/0026532 | A1 | 2/2007 | Ikami |
| 2011/0189723 | A1 | 8/2011 | Yamamura et al. |

FOREIGN PATENT DOCUMENTS

| | | |
|---|---|---|
| JP | 10-504397 A | 4/1998 |
| JP | 2000-078998 A | 3/2000 |
| JP | 2000-304698 A | 11/2000 |
| JP | 2000-321206 A | 11/2000 |
| JP | 2001-238674 A | 9/2001 |
| JP | 2003-248007 A | 9/2003 |
| JP | 2005-523684 A | 8/2005 |
| JP | 2006-153639 A | 6/2006 |
| JP | 2006-317426 A | 11/2006 |
| JP | 2006-322819 A | 11/2006 |
| JP | 2006-349501 A | 12/2006 |
| JP | 2007-033170 A | 2/2007 |
| WO | 2010/027003 A1 | 3/2010 |

OTHER PUBLICATIONS

The Extended European Search Report dated Mar. 31, 2015 for the related European Patent Application No. 13769735.5.

* cited by examiner

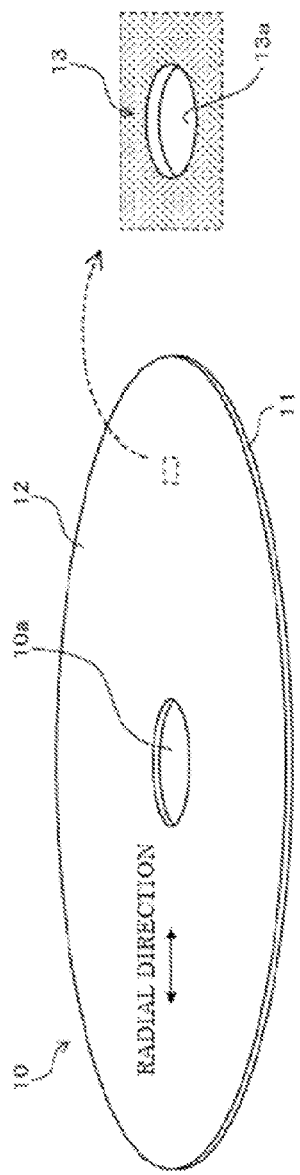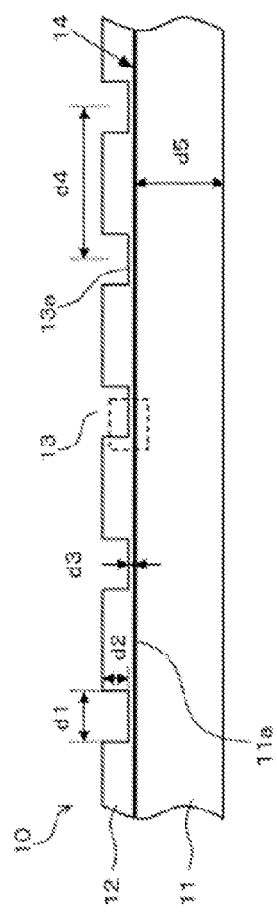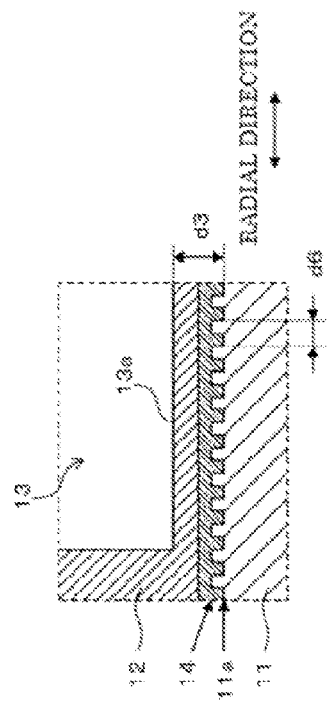
FIG. 1A
FIG. 1B
FIG. 1C

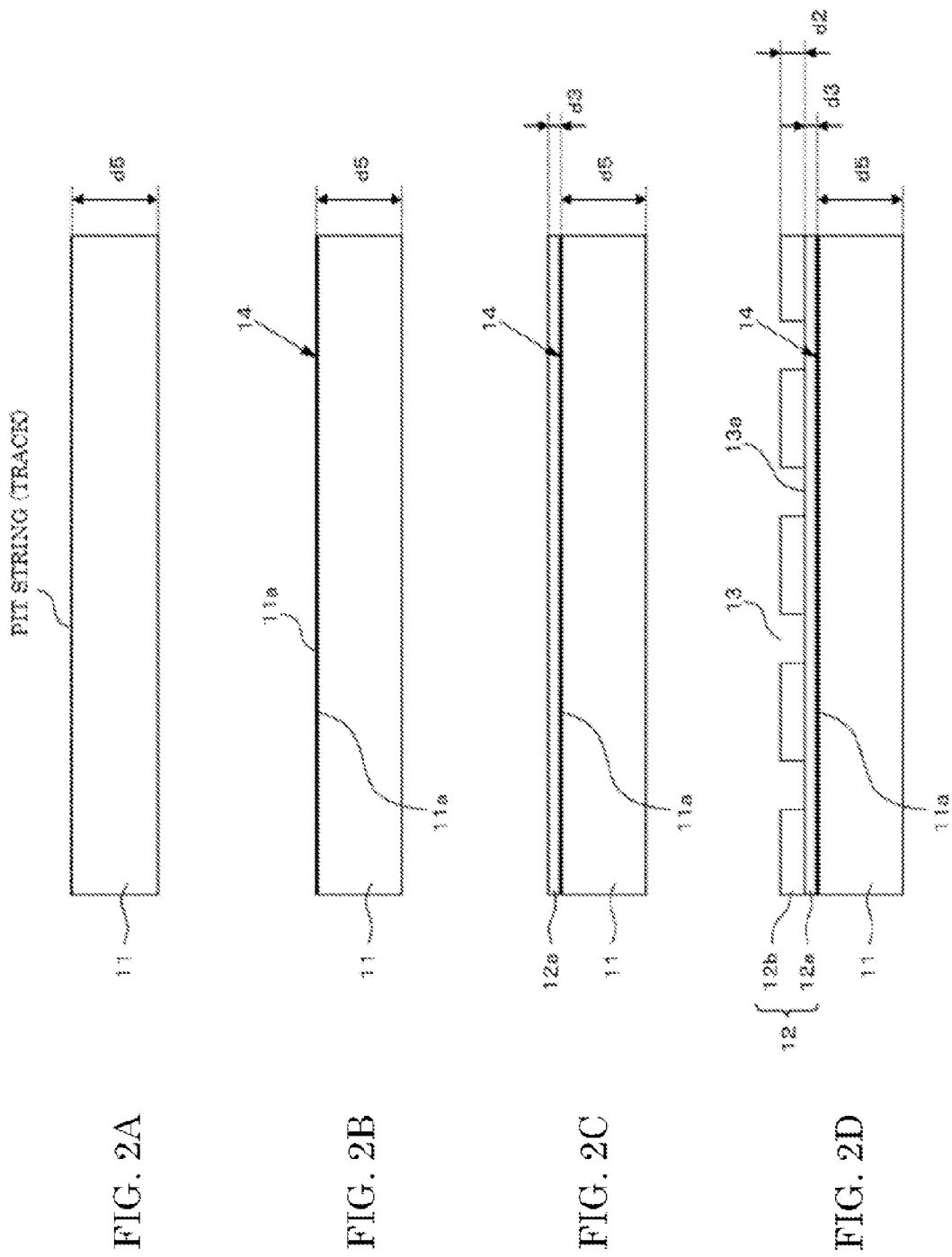

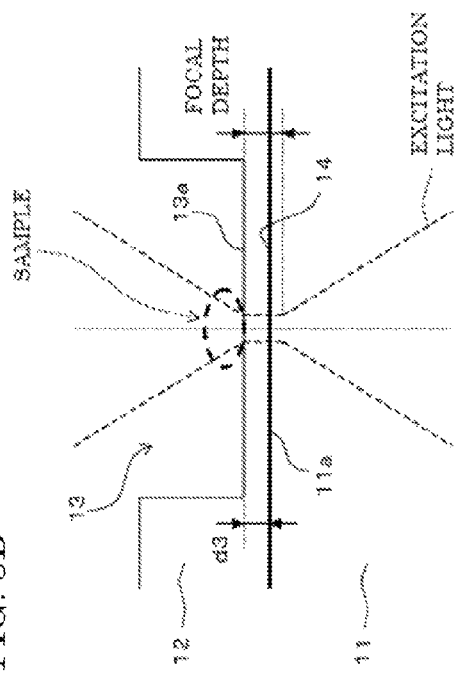
FIG. 5B
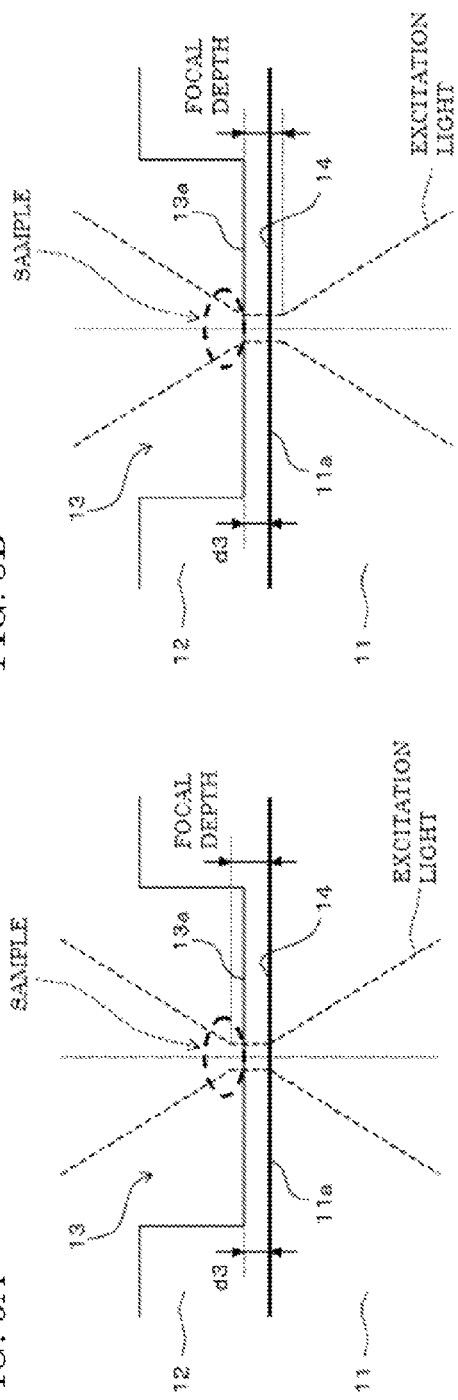
FIG. 5A
FIG. 5C

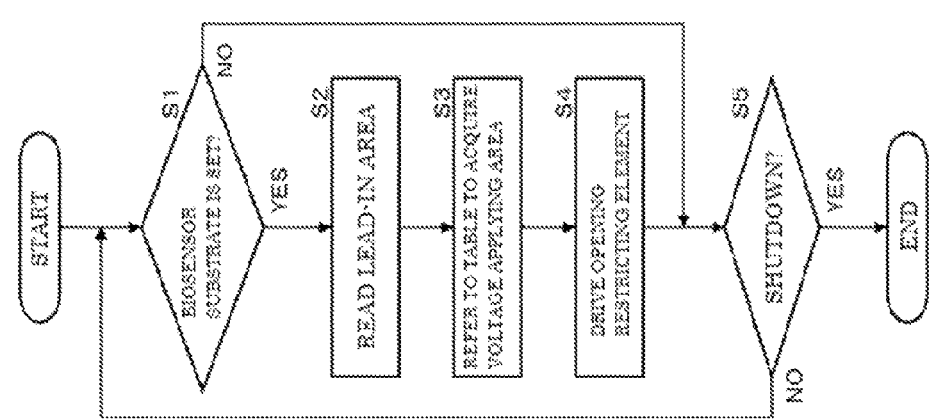

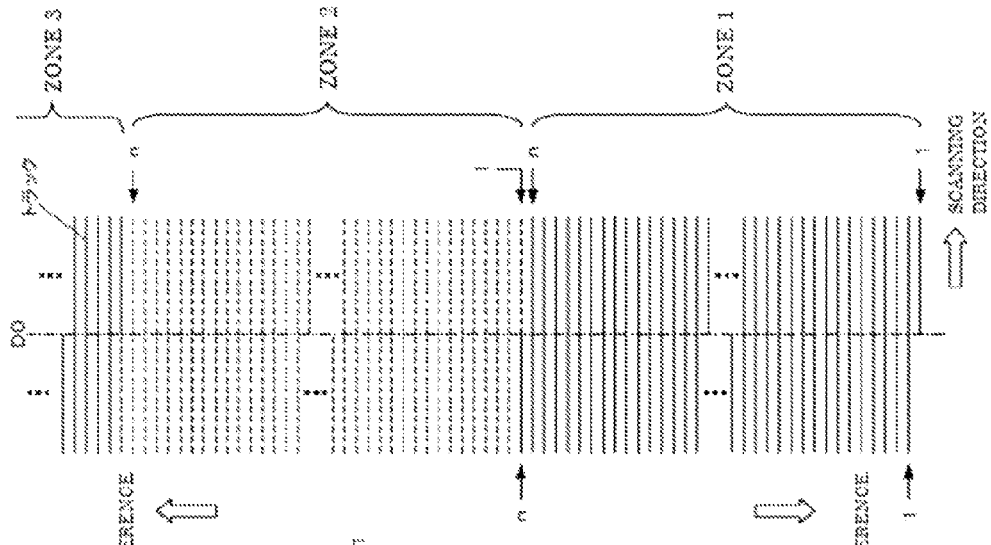
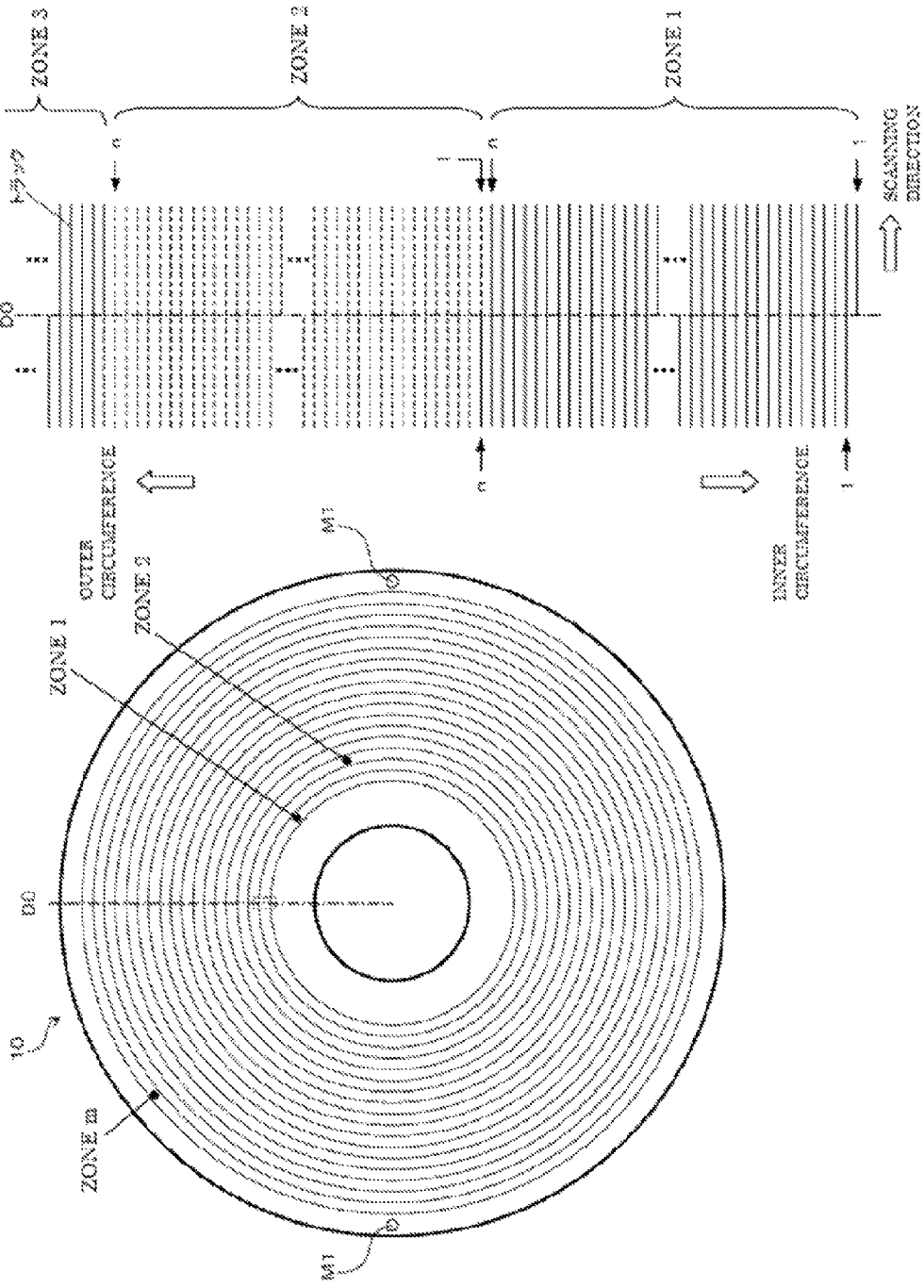

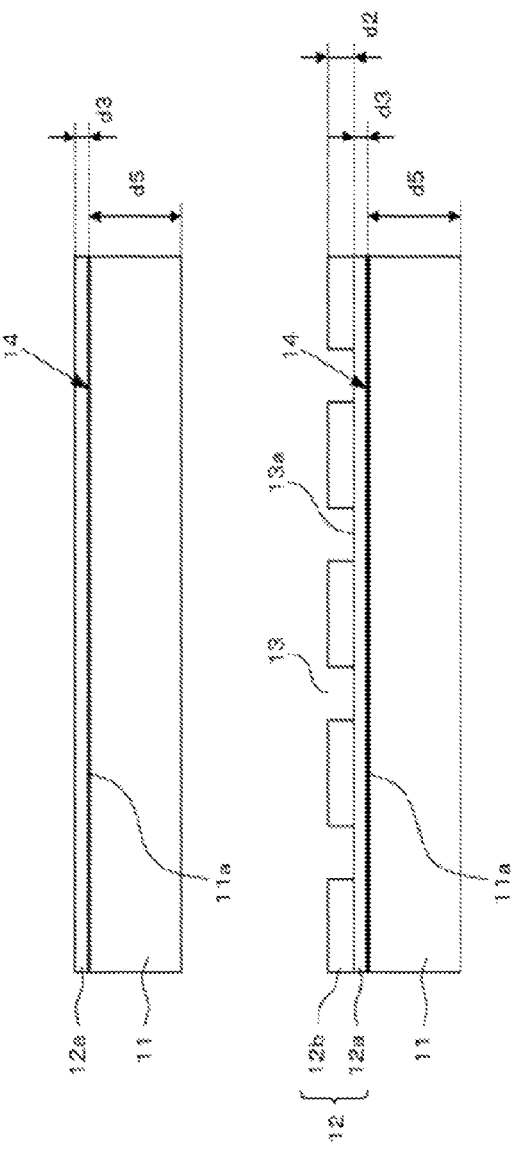
FIG. 15A
FIG. 15B
FIG. 15C
FIG. 15D

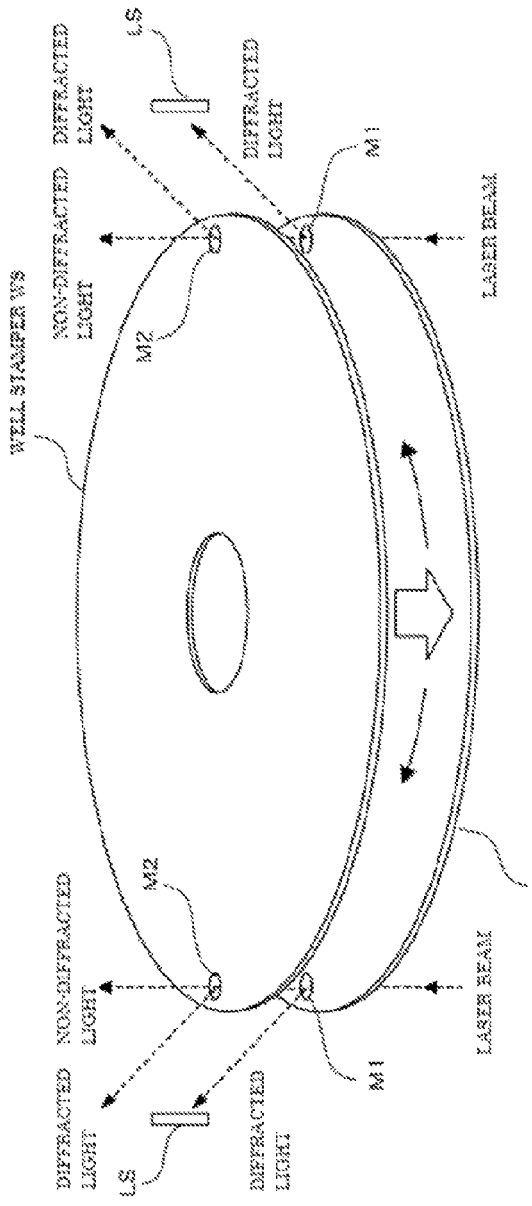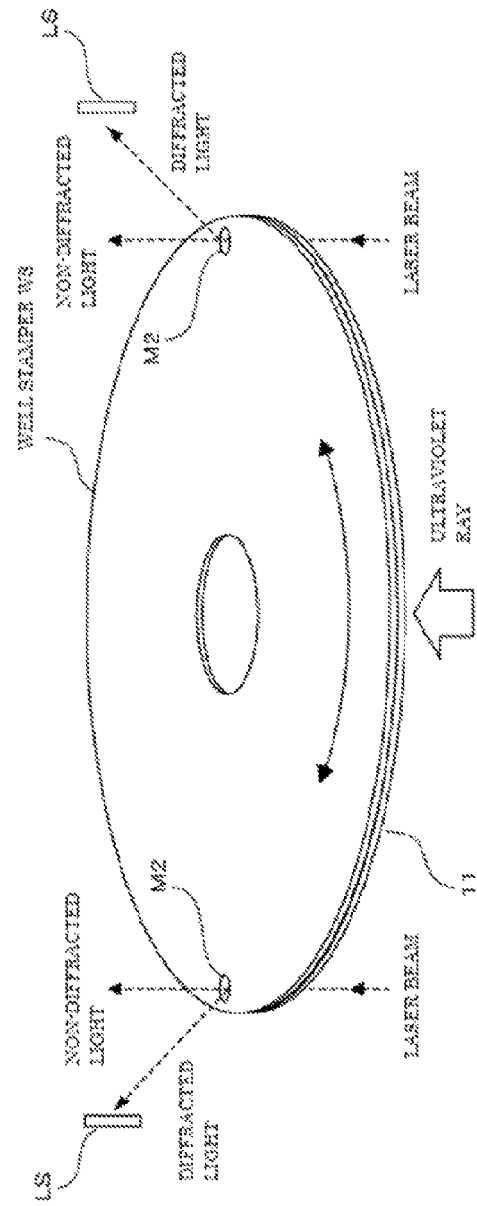
FIG. 16A
FIG. 16B

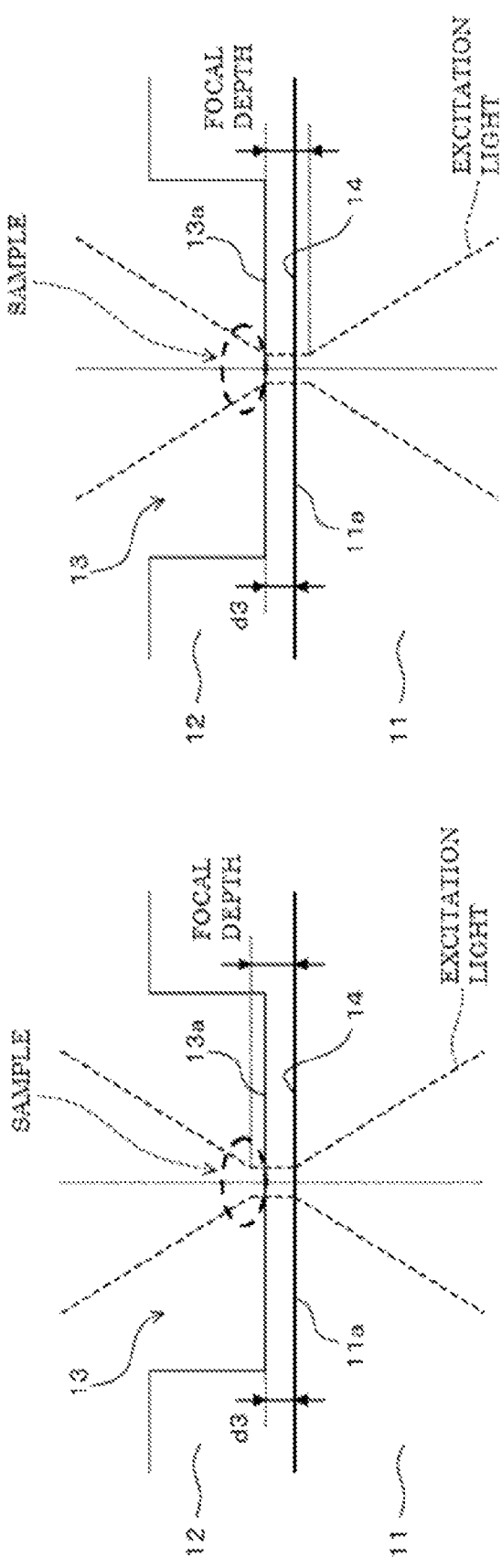

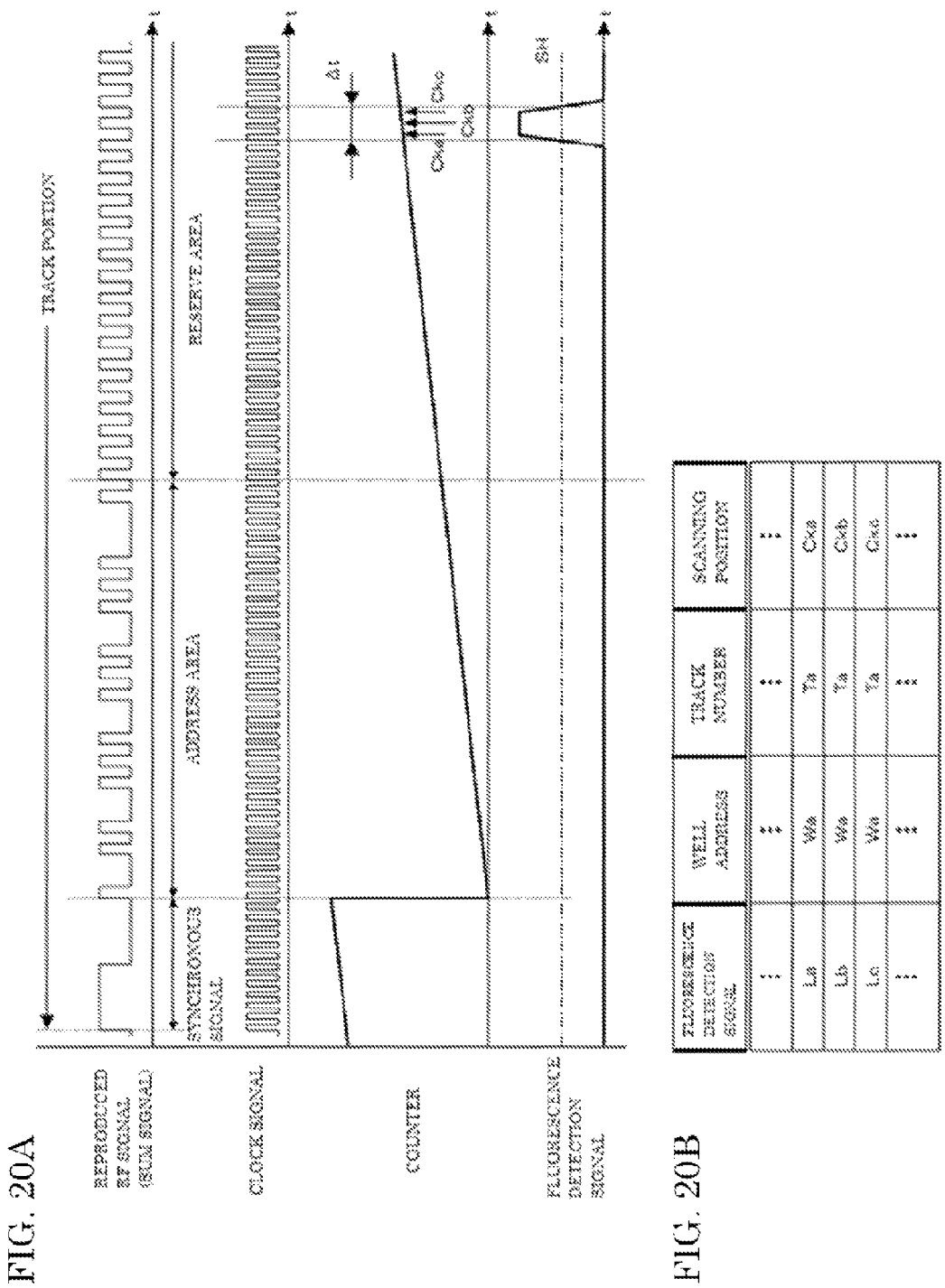

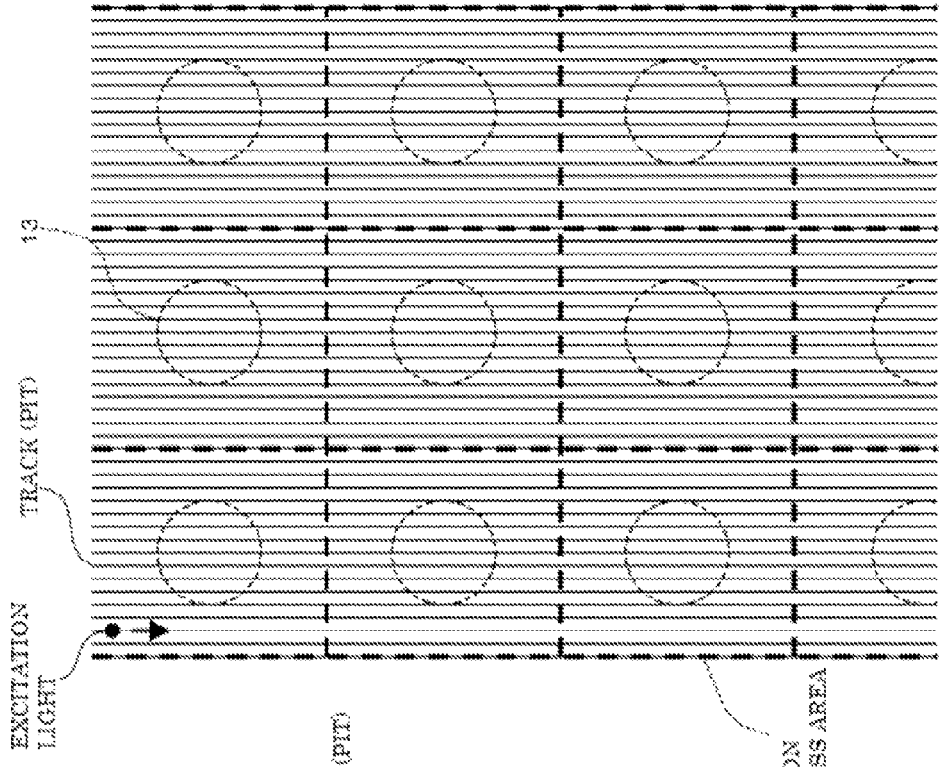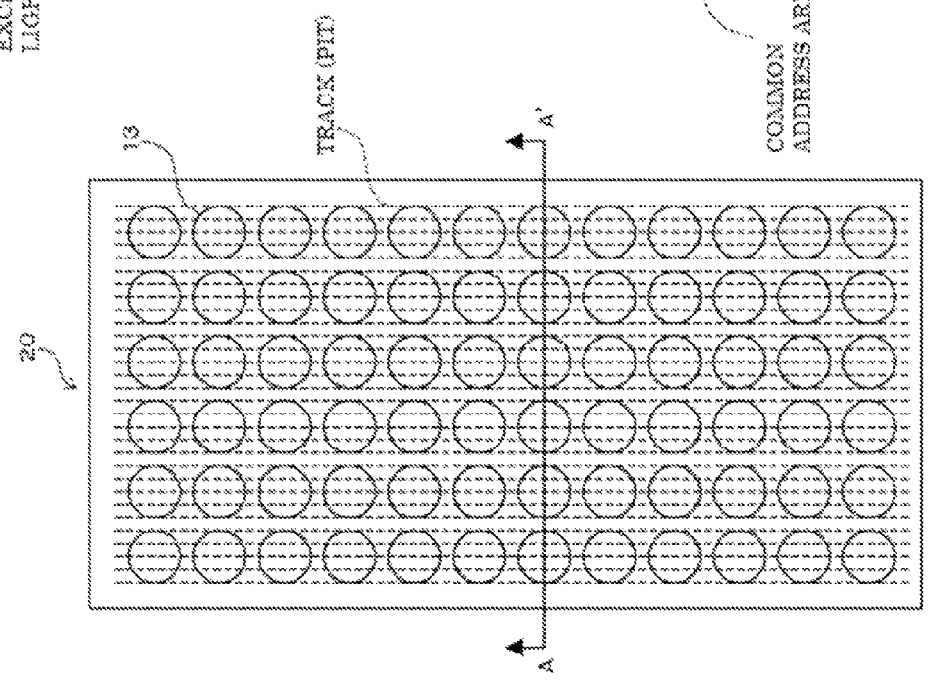

SAMPLE HOLDING CARRIER, AND FLUORESCENCE DETECTION SYSTEM AND FLUORESCENCE DETECTION DEVICE THAT USE SAME

RELATED APPLICATIONS

This application is a Continuation of International Application No. PCT/JP2013/057462, filed on Mar. 15, 2013, which in turn claims the benefit of Japanese Application No. 2012-077896, filed on Mar. 29, 2012 and Japanese Application No. 2012-077902, filed on Mar. 29, 2012, the disclosures of which Applications are incorporated by reference herein.

TECHNICAL FIELD

The present invention relates to a sample holding carrier that holds a sample prepared by fluorescently labeling a subject such as a cell, and a fluorescence detection system and a fluorescence detection device that use the same.

BACKGROUND ART

Particularly, in medical fields such as a clinical site, it is necessary to detect a cell infected with a pathogen or a cell having a predetermined mode from many cells. For example, WO 2010/027003 discloses a technique of rapidly, simply, and accurately detecting the cell. In the technique of WO 2010/027003, plural micro chambers (wells) are formed on a micro chip array, and each well is filled with fluorescently-labeled cells. Each well is observed with a fluorescent microscope while irradiated with a laser beam, and thereby a specific cell that yields fluorescence is detected.

Unexamined Japanese Patent Publication No. 2006-322819 discloses a configuration in which a series of wells filled with the cells is scanned with the laser beam to detect the fluorescence yielded from the cell. In the configuration of Unexamined Japanese Patent Publication No. 2006-322819, the series of wells is formed in a circumferential direction of a disk, and a series of information pits is formed on a layer on a light incident side separated from a layer in which the well is formed, the series of information pits being formed into a track shape so as to be arranged along an array of the wells. Address information is held in the information pit.

In the configuration of Unexamined Japanese Patent Publication No. 2006-322819, a light source that emits excitation light to the well and a light source that emits a laser beam to the information pit are separately prepared in an optical system that detects the fluorescence, and the light emitted from each light source is caused to converge by a common objective lens. The objective lens is controlled such that the laser beam for the information pit is focused on the information pit to follow an information pit string (track). Therefore, the excitation light is focused on the cells filling the well and the series of wells is sequentially scanned with the laser beam. The optical system includes a photodetector that detects the fluorescence yielded from the cell and a photodetector that receives the laser beam modulated by the information pit. A signal used to control the objective lens and a signal used to reproduce information held in the information pit are generated from output of the photodetector that receives the laser beam.

When the fluorescence is yielded from the cell irradiated with the excitation light, the fluorescence is detected by the photodetector that detects the fluorescence. A position of the well in which the cell yielding the fluorescence is accommodated is identified by positional information that is acquired from the information pit in detecting the fluorescence. The existence or non-existence of a detection target cell and the position of the well in which the cell is accommodated are automatically detected from many cells accommodated in the series of wells provided on the disk without the fluorescence microscope observation.

SUMMARY OF THE INVENTION

Technical Problems

However, in Unexamined Japanese Patent Publication No. 2006-322819, because of necessity of the two laser light sources, unfortunately a device configuration becomes complicated. Because focus control of the excitation light is not directly performed, possibly a convergent position of the excitation light is deviated from the cell in the bottom surface of the well, which results in a risk of degrading detection accuracy of the cell.

In Unexamined Japanese Patent Publication No. 2006-322819, plural tracks traverse one well because the size of the well is much larger than the size of the information pit. Therefore, plural pieces of address information acquired from the information pits are associated with the one well, and the identification of the position of the well with the address information becomes significantly troublesome. Sometimes the address information is switched while a predetermined track traverses the well, which results in a problem which one of the pre-switch address information and the post-switch address information is applied to the well.

In view of the above problems, an object of the present invention is to provide a sample holding carrier that can accurately measure the sample with the simple configuration, a fluorescence detection system and a fluorescence detection device that use the same.

Another object of the present invention is to provide a sample holding carrier that can precisely associate the address information with the well (sample accommodation unit) and a fluorescence detection device provided therewith.

Solution to Problems

A first aspect of the present invention relates to a sample holding carrier. A sample holding carrier according to the first aspect includes: a substrate on which irradiation light is incident from a lower surface; a reflecting film that is arranged on an upper surface of the substrate to partially reflect the irradiation light; and plural sample accommodation units that are arranged on an upper surface side of the reflecting film and have bottom surfaces. The irradiation light is converged to be incident on the substrate. A distance from a reflecting surface that is of a boundary between the reflecting film and the substrate to the bottom surface of the sample accommodation unit is less than or equal to a focal depth of the irradiation light.

According to the sample holding carrier of the first aspect, the distance between the reflecting surface and the bottom surface of the sample accommodation unit is less than or equal to the focal depth of the irradiation light. Therefore, the bottom surface of the sample accommodation unit can be included in the range of the focal depth of the irradiation light by performing the control to focus the irradiation light on the reflecting surface on the device side. Therefore, the sample accommodated in the bottom surface of the sample accommodation unit can surely and efficiently be irradiated with the irradiation light, and accurately be measured.

According to the sample holding carrier of the first aspect, the focal depth of the irradiation light overlaps the bottom surface of the sample accommodation unit, so that both adjustment of the focal position and irradiation of the sample can be performed only by the irradiation light. Therefore, necessity to provide a light source for servo is eliminated in addition to a light source for the irradiation light, and the configuration of the optical system can be simplified.

The sample holding carrier of the first aspect may further include a track that is formed in the upper surface of the substrate. At this point, desirably address information identifying a position on the sample holding carrier is held in the track. Therefore, on the device side, the position of the sample accommodation unit in which the fluorescence is detected can be identified on the sample holding carrier based on the address information.

In the sample holding carrier of the first aspect, desirably a parameter value that is used to derive the focal depth applied to the sample holding carrier is stored in the track. Therefore, on the device side, the focal depth suitable for each sample holding carrier can be recognized by referring to the parameter value, and the measure to adjust the focal depth can be taken.

A second aspect of the present invention relates to a fluorescence detection system that irradiates a sample holding carrier holding a fluorescently-labeled sample with irradiation light from a fluorescence detection device and detects fluorescence yielded from the sample irradiated with the irradiation light using the fluorescence detection device. In the fluorescence detection system of the second aspect, the sample holding carrier includes: a substrate on which the irradiation light is incident from a lower surface; a reflecting film that is arranged on an upper surface of the substrate to partially reflect the irradiation light; and plural sample accommodation units that are arranged on an upper surface side of the reflecting film and have bottom surfaces. The fluorescence detection device includes an optical system that causes the irradiation light to converge to be incident on the substrate. A distance from a reflecting surface that is of a boundary between the reflecting film and the substrate to the bottom surface of the sample accommodation unit is less than or equal to a focal depth of the irradiation light.

According to the fluorescence detection system of the second aspect, the distance between the reflecting surface and the bottom surface of the sample accommodation unit is less than or equal to the focal depth of the irradiation light. Therefore, the bottom surface of the sample accommodation unit can be included in the range of the focal depth of the irradiation light by performing the control to focus the irradiation light on the reflecting surface on the fluorescence detection device side. Therefore, the sample accommodated in the bottom surface of the sample accommodation unit can surely and efficiently be irradiated with the irradiation light, and accurately be measured.

In the fluorescence detection system of the second aspect, the sample holding carrier may hold a parameter value that is used to derive the focal depth applied to the sample holding carrier. In this case, the fluorescence detection device includes: a reading unit that reads the parameter value; a focal depth adjusting unit that changes the focal depth of the irradiation light; and a control unit that controls the focal depth adjusting unit so as to obtain the focal depth corresponding to the parameter value read by the reading unit.

According to the configuration, on the fluorescence detection device side, the focal depth suitable for the sample holding carrier can be recognized by referring to the parameter value held in the sample holding carrier. The focal depth adjusting unit is controlled such that the recognized focal depth is obtained, which allows the focal depth of the irradiation light to fit to the sample holding carrier. Therefore, according to the configuration, the focal depth can be properly set to various sample holding carriers, and the sample can more properly be measured.

A third aspect of the present invention relates to a fluorescence detection device that irradiates a sample holding carrier holding a fluorescently-labeled sample with irradiation light and detects fluorescence yielded from the sample irradiated with the irradiation light. In the fluorescence detection device of the third aspect, the sample holding carrier includes: a substrate on which the irradiation light is incident from a lower surface; a track that is formed in an upper surface of the substrate; a reflecting film that is arranged on the upper surface of the substrate to partially reflect the irradiation light; and plural sample accommodation units that are arranged on an upper surface side of the reflecting film and have bottom surfaces. The fluorescence detection device of the third aspect includes: a light source that emits the irradiation light; an objective lens that causes the irradiation light to converge on the sample holding carrier; an objective lens actuator that drives the objective lens in at least a focus direction parallel to an optical axis and a tracking direction perpendicular to the track; a separation element that introduces the irradiation light emitted from the light source to the objective lens and separates the fluorescence from the irradiation light reflected by the sample holding carrier; a photodetector that receives the irradiation light, which is reflected by the sample holding carrier and separated from the fluorescence by the separation element, and outputs a signal in order to generate a focus error signal and a tracking error signal; a control unit that controls the objective lens actuator based on the focus error signal and the tracking error signal; a fluorescence detector that receives the fluorescence separated by the separation element; and a light scanning unit that changes a relative position between the objective lens and the sample holding carrier such that the irradiation light moves on the sample holding carrier along the track. At this point, a distance from a reflecting surface that is of a boundary between the reflecting film and the substrate to the bottom surface of the sample accommodation unit is less than or equal to a focal depth of the irradiation light.

The fluorescence detection device of the third aspect is suitably used to detect the fluorescence in the sample holding carrier of the first aspect. Using the fluorescence detection device of the third aspect, the bottom surface of the sample accommodation unit can be included in the range of the focal depth of the irradiation light, and the sample accommodated in the bottom surface of the sample accommodation unit can surely and efficiently be irradiated with the irradiation light. Therefore, the sample can accurately be measured.

According to the fluorescence detection device of the third aspect, both tracking and the irradiation of the sample can be performed only by one piece of irradiation light emitted from one light source, the necessity to provide the light source for the servo is eliminated in addition to the light source for the irradiation light, and the configuration of the optical system can be simplified.

In the case that the sample holding carrier holds a parameter value that is used to derive the focal depth applied to the sample holding carrier, the fluorescence detection device of the third aspect may further include: a reading unit that reads the parameter value; a focal depth adjusting unit that changes the focal depth of the irradiation light; and a focal depth control unit that controls the focal depth adjusting unit so as to obtain the focal depth corresponding to the parameter value read by the reading unit.

According to the configuration, the focal depth suitable for the sample holding carrier can be recognized by referring to the parameter value held in the sample holding carrier, and the focal depth adjusting unit is controlled such that the recognized focal depth is obtained, whereby the focal depth of the irradiation light can fit to the sample holding carrier. Therefore, according to the configuration, the focal depth can be properly set to various sample holding carriers, and the sample can more properly be measured.

A fourth aspect of the present invention relates to a sample holding carrier. A sample holding carrier of the fourth aspect includes: a substrate; a track that is formed in an upper surface of the substrate to hold predetermined information; and plural sample accommodation units that are arranged on an upper surface side of the substrate to accommodate samples. At this point, the track traverses a portion below the sample accommodation unit, and identical well address information identifying a position of the sample accommodation unit is provided to plural track portions traversing the identical sample accommodation unit.

According to the sample holding carrier of the fourth aspect, the identical well address information identifying the position of the sample accommodation unit is provided to the plural track portions traversing the identical sample accommodation unit, so that the sample accommodation unit can be associated with the position of the sample accommodation unit identified by the well address information on a one-on-one basis. Therefore, the position of the sample accommodation unit can easily and smoothly be identified using the well address information.

In the sample holding carrier of the fourth aspect, a common address area may be set along the track and has a size that includes the sample accommodation unit, the common address area having a width of a predetermined number of tracks in a direction traversing the track and a width of a predetermined track length in a direction along the track. In this case, the sample accommodation unit is arranged such that the one sample accommodation unit is allocated to the one common address area, and the identical well address information is provided to the track portion included in the identical common address area.

According to the configuration, the identical well address information is provided to the common address area wider than the sample accommodation unit, so that the sample accommodation unit can be located in the common address area even if the position of the sample accommodation unit is deviated in arranging the sample accommodation unit in the sample holding carrier. Therefore, the identical well address information can more surely be provided to one sample accommodation unit.

In the sample holding carrier of the fourth aspect, in a group of the track portions to which the identical well address information is provided, track address information distinguishing one track portion from other track portions may be provided to the track portion. According to the configuration, on the fluorescence detection device side, the position in the direction traversing the track on the sample accommodation unit can be recognized by acquiring the track address information. Therefore, the position where the fluorescence is yielded can more finely be recognized.

A fifth aspect of the present invention relates to a fluorescence detection device that irradiates a sample holding carrier holding a fluorescently-labeled sample with irradiation light and detects fluorescence yielded from the sample irradiated with the irradiation light. At this point, the sample holding carrier includes: a substrate; a track that is formed in an upper surface of the substrate to hold predetermined information; and plural sample accommodation units that are arranged on an upper surface side of the substrate to accommodate samples, the track traverses a portion below the sample accommodation unit, and identical well address information identifying a position of the sample accommodation unit is provided to plural track portions traversing the identical sample accommodation unit. The fluorescence detection device of the fifth aspect includes: a light source that emits the irradiation light; an objective lens that causes the irradiation light to converge on the sample holding carrier; a light scanning unit that performs scanning along the track with the irradiation light caused to converge by the objective lens; a photodetector that receives the irradiation light reflected by the sample holding carrier; a reproducing unit that reproduces the well address information from output from the photodetector; and a scanning position detector that detects a scanning position of the irradiation light on the track portion.

According to the fluorescence detection device of the fifth aspect, the identical well address information is provided to the track portion traversing the identical sample accommodation unit, so that the position of the sample accommodation unit can easily be identified based on the well address information reproduced by the reproducing unit. The scanning position of the irradiation light on the track portion is detected by the scanning position detector, so that the scanning position of the irradiation light can be identified on each track portion when the fluorescence is detected. Therefore, the position where the fluorescence is detected in the sample accommodation unit can more finely be recognized.

In the fluorescence detection device of the fifth aspect, in the sample holding carrier, in a group of the track portions to which the identical well address information is provided, track address information distinguishing one track portion from other track portions may be provided to the track portion. In this case, the reproducing unit of the fluorescence detection device of the fifth aspect reproduces the track address information based on the output from the photodetector. The fluorescence detection device of the fifth aspect further includes a fluorescent position identifying unit, the fluorescent position identifying unit identifying a position where fluorescence is yielded on the sample holding carrier by associating the well address information reproduced by the reproducing unit and the track address information with the scanning position detected by the scanning position detector based on the output from the photodetector.

According to the fluorescence detection device of the fifth aspect, the position where the fluorescence is yielded is identified by the position of the sample accommodation unit, and the position where the fluorescence is yielded is also identified by the track in the sample accommodation unit and the scanning position on the track. Therefore, in fluorescence detection device, the position where the fluorescence is yielded can more finely be recognized.

The fluorescence detection device of the fifth aspect may further include an objective lens actuator that drives the objective lens and a control unit that controls the objective lens actuator. In the fluorescence detection device of the fifth aspect, the sample accommodation unit may not be arranged in the sample holding carrier in a belt-like area having a predetermined width in a direction perpendicular to the track. In this case, the control unit may control the objective lens actuator so as to move a position irradiated with the irradiation light in a direction traversing the track, when a scanning position of the irradiation light is included in the belt-like area.

According to the configuration, the area where the sample accommodation unit is not arranged is skipped, so that the sample holding carrier can rapidly and smoothly be scanned with the irradiation light.

Advantageous Effects of Invention

As described above, the present invention can provide the sample holding carrier that can accurately measure the sample with the simple configuration, and the fluorescence detection system and the fluorescence detection device that use the same.

According to the present invention, the sample holding carrier that can precisely associate the address information with the well (sample accommodation unit) and the fluorescence detection device provided therewith can be provided.

The advantageous effects and meanings of the present invention will be more apparent by the following description of the exemplary embodiments. However, the following exemplary embodiments are described only by way of example, but the present invention is not limited to the exemplary embodiments.

BRIEF DESCRIPTION OF DRAWINGS

FIG. 1A is a perspective view schematically illustrating an appearance configuration of a biosensor substrate according to a first exemplary embodiment, FIG. 1B is a sectional view of the biosensor substrate when the biosensor substrate is cut in a plane perpendicular to a surface of the biosensor substrate, and FIG. 1C is a partially enlarged view illustrating the section of the biosensor substrate.

FIGS. 2A to 2D are views illustrating a method for producing the biosensor substrate of the first exemplary embodiment.

FIGS. 5A to 5C are views illustrating a focal depth of excitation light of the first exemplary embodiment.

FIG. 9A is a flowchart illustrating an opening restricting element driving operation performed by a controller of the first modification, and FIG. 9B is a view illustrating a table previously stored in a memory of the controller.

FIGS. 12A and 12B are views illustrating a method for segmenting a track of the second exemplary embodiment.

FIGS. 15A to 15D are views illustrating a method for producing the biosensor substrate of the second exemplary embodiment.

FIGS. 16A and 16B are views illustrating a method for producing the biosensor substrate of the second exemplary embodiment.

FIGS. 19A and 19B are views illustrating a focal depth of excitation light of the second exemplary embodiment.

FIGS. 20A and 20B are views illustrating a method for detecting a scanning position in a track direction of the second exemplary embodiment.

FIGS. 30A and 30B are views schematically illustrating a configuration example of the biosensor substrate of the second exemplary embodiment when the biosensor substrate has the square outline.

DESCRIPTION OF EMBODIMENTS

First Exemplary Embodiment

Figure 3:
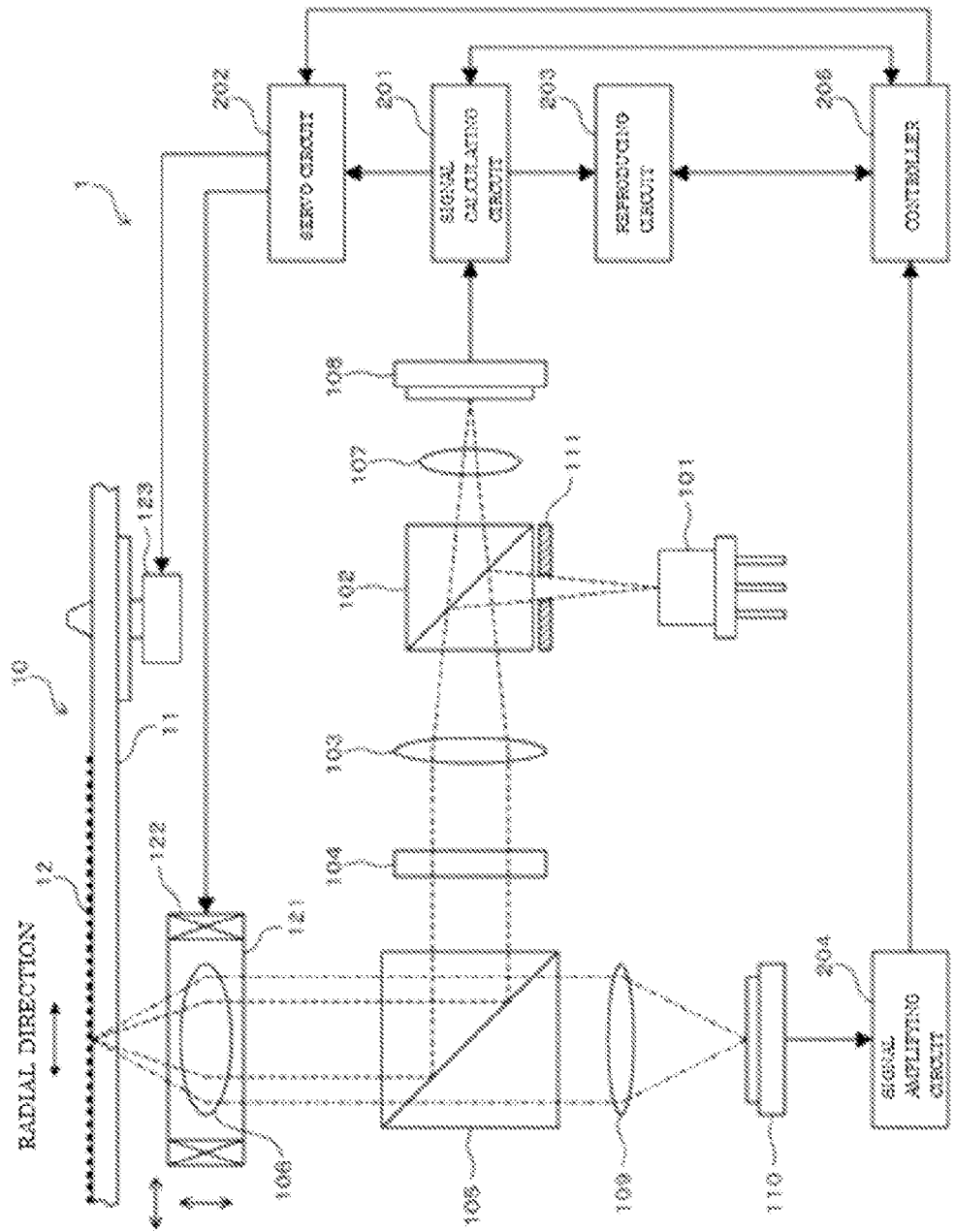
FIG. 3 is a view illustrating a configuration of a fluorescence detection device of the first exemplary embodiment.

Hereinafter, a first exemplary embodiment of the present invention will be described with reference to the drawings.

<Biosensor Substrate>

FIG. 1A is a perspective view schematically illustrating an appearance configuration of biosensor substrate 10 according to the first exemplary embodiment. For example, biosensor substrate 10 is used to detect an erythrocyte infected with a malaria parasite in human blood.

Biosensor substrate 10 has a disc shape similar to an optical disk (such as a CD and a DVD), and circular hole 10a is made in the center of biosensor substrate 10. Biosensor substrate 10 has a structure in which well layer 12 is stacked on an upper surface of base substrate 11. As illustrated in an enlarged view at the right end of FIG. 1A, plural micro wells 13 constructed with columnar voids are formed in well layer 12. Wells 13 are concentrically or spirally arrayed from an inner circumference toward an outer circumference of biosensor substrate 10. Well 13 includes bottom surface portion 13a lower than a upper surface of well layer 12, and a diameter and a height of well 13 are set such that a sample is accommodated in well 13 when dropped into well 13.

FIG. 1B is a sectional view of biosensor substrate 10 when biosensor substrate 10 is cut in a plane perpendicular to a surface of biosensor substrate 10, and FIG. 1C is an enlarged view of a broken-line portion in FIG. 1B.

Similar to the optical disk, a spiral track (pit strings) is formed on an upper side (the side of well layer 12) of base substrate 11. The pit holds address information in order to identify a position on the surface of biosensor substrate 10. Similar to the CD and the DVD, the track is scanned with excitation light (to be described) at a constant linear velocity to reproduce the address information. Reflecting film 14 is provided between base substrate 11 and well layer 12. Reflecting surface 11a that is of an interface between reflecting film 14 and base substrate 11 is formed on the upper surface of base substrate 11 by stacking reflecting film 14 on the upper surface of base substrate 11. Wells 13 are formed at predetermined intervals on the upper surface side of well layer 12. Bottom surface portion 13a of well 13 is located slightly higher than reflecting film 14, and bottom surface portion 13a of well 13 separates from the upper surface of reflecting film 14.

At this point, it is assumed that d1 and d2 are the diameter and the height of well 13, that d3 is a distance between bottom surface portion 13a and reflecting surface 11a, that d4 is the interval between wells 13, that d5 is a thickness of base substrate 11, and that d6 is a track pitch of reflecting surface 11a. In the first exemplary embodiment, diameter d1 is set to 100 μm, height d2 is set to 50 μm, distance d3 is set to 2 μm, interval d4 is set to 300 μm, thickness d5 is set to 0.6 mm, and track pitch d6 is set to 1 μm. Reflecting film 14 has a reflectance of 3% to 4% for the excitation light (to be described).

In the first exemplary embodiment, base substrate 11 is made of polycarbonate, well layer 12 is made of an ultraviolet curing resin, and reflecting film 14 is made of metal such as aluminum and a silver alloy, niobium oxide, or a wavelength selection film. Instead of polycarbonate, base substrate 11 may be made of polymethylmethacrylate or amorphous polyolefin. Well layer 12 may be made of silicone, polycarbonate, polymethylmethacrylate, and amorphous polyolefin. For example, the thickness of reflecting film 14 is set to 5 nm to 20 nm such that the desired reflectance is obtained.

FIGS. 2A to 2D are views illustrating a method for producing biosensor substrate 10. As described below, the method in FIGS. 2A to 2D is substantially identical to a method for producing the optical disk.

As illustrated in FIG. 2A, base substrate 11 is formed by injection molding. Therefore, base substrate 11 has thickness d5, and a string of pits is formed on the upper surface of base substrate 11. As illustrated in FIG. 2B, reflecting film 14 is evaporated on the upper surface of base substrate 11, thereby forming reflecting surface 11a on the upper surface of base substrate 11. As illustrated in FIG. 2C, bottom layer 12a is stacked on the upper surface of reflecting film 14 by spin coating. As illustrated in FIG. 2D, top layer 12b having thickness d2 is formed on the upper surface of bottom layer 12a by photo-polymer molding. Therefore, plural wells 13 as shown in FIG. 1B are formed. Well layer 12 is formed by combining bottom layer 12a and top layer 12b.

<Fluorescence Detection Device>

FIG. 3 is a view illustrating a configuration of fluorescence detection device 1 of the first exemplary embodiment. For example, fluorescence detection device 1 is used to determine whether the erythrocyte accommodated in well 13 of biosensor substrate 10 is infected with the malaria parasite.

In the use of fluorescence detection device 1, the sample produced by fluorescently labeling the subject is previously accommodated in well 13 of biosensor substrate 10. In the first exemplary embodiment, in the case that the erythrocyte that is of the subject having a diameter of about 10 μm and a thickness of about 2 μm is infected with the malaria parasite, an inside of the erythrocyte is fluorescently labeled, the plural infected erythrocytes and the plural non-infected erythrocytes are arrayed in parallel in bottom surface portion 13a of well 13 having a diameter of 100 μm. Hole 10a (see FIG. 1A) of biosensor substrate 10 in which the sample is accommodated is set in rotating device 123 (turntable) of fluorescence detection device 1 to start the measurement.

An optical system of fluorescence detection device 1 includes semiconductor laser 101, Polarization Beam Splitter (PBS) 102, collimator lens 103, quarter-wave plate 104, dichroic prism 105, objective lens 106, anamorphic lens 107, photodetector 108, collective lens 109, fluorescence detector 110, and aperture 111. In addition to the optical system, fluorescence detection device 1 includes holder 121, objective lens actuator 122, rotating device 123, signal calculating circuit 201, servo circuit 202, reproducing circuit 203, signal amplifying circuit 204, and controller 205.

Semiconductor laser 101 emits a laser beam (hereinafter referred to as "excitation light") having a wavelength of about 405 nm. The excitation light of the first exemplary embodiment is an example of the irradiation light of claims of the present invention. In the excitation light emitted from semiconductor laser 101, the excitation light introduced to biosensor substrate 10, namely, the excitation light passing through aperture 111 is indicated by a broken line in FIG. 3. A circular opening having a predetermined diameter is formed in aperture 111, and a diameter of the excitation light is restricted by aperture 111. The position of semiconductor laser 101 is adjusted such that the excitation light emitted from semiconductor laser 101 becomes S-polarized light with respect to PBS 102. Therefore, after the diameter of the excitation light emitted from semiconductor laser 101 is restricted by aperture 111, the excitation light is reflected by PBS 102, and is incident on collimator lens 103.

Collimator lens 103 converts the excitation light incident from the side of PBS 102 into parallel light. Therefore, the excitation light passing through collimator lens 103 becomes the parallel light having a predetermined diameter. Quarter-wave plate 104 converts the excitation light incident from the side of collimator lens 103 into circularly-polarized light, and converts the excitation light incident from the side of dichroic prism 105 into linearly-polarized light that is orthogonal to a polarization direction of the excitation light incident from the side of collimator lens 103. Therefore, the excitation light incident from the side of collimator lens 103 on PBS 102 is transmitted through PBS 102.

Dichroic prism 105 reflects the laser beam having a wavelength of about 405 nm, and transmits the laser beams having a wavelength of about 450 nm to about 540 nm. Therefore, the excitation light incident from the side of quarter-wave plate 104 is reflected by dichroic prism 105, and is incident on objective lens 106.

Objective lens 106 causes the excitation light to converge properly with respect to biosensor substrate 10. Specifically, objective lens 106 has a predetermined NA (Numerical Aperture, in this case, 0.34) such that the excitation light incident from the side of dichroic prism 105 converges. An incident diameter of the excitation light to objective lens 106 is decided by the diameter of aperture 111. A focal depth of the excitation light that is caused to converge by objective lens 106 changes depending on the NA of the excitation light. The focal depth of the excitation light is described later with reference to FIGS. 5A to 5C.

While held by holder 121, objective lens 106 is driven in a focus direction (a direction perpendicular to biosensor substrate 10) and a tracking direction (a radial direction of biosensor substrate 10) by objective lens actuator 122. That is, objective lens 106 is driven such that the excitation light follows the track including the pit strings while focusing on reflecting surface 11a of biosensor substrate 10. The excitation light focusing on reflecting surface 11a is partially reflected by reflecting surface 11a, and largely transmitted through reflecting surface 11a.

The excitation light (hereinafter referred to as "reflected excitation light") reflected by reflecting surface 11a is reflected by dichroic prism 105, converted into the linearly-polarized light by quarter-wave plate 104, and converted into convergent light by collimator lens 103. The reflected excitation light incident from the side of collimator lens 103 on PBS 102 is transmitted through PBS 102 as described above.

Anamorphic lens 107 introduces astigmatism to the reflected excitation light incident from the side of PBS 102. The reflected excitation light transmitted through the anamorphic lens 107 is incident on photodetector 108. Photodetector 108 includes a quadrant sensor that receives the reflected excitation light on a light receiving surface. A detection signal of photodetector 108 is input to signal calculating circuit 201.

In the excitation light with which biosensor substrate 10 is irradiated, the excitation light transmitted through reflecting surface 11a reaches bottom surface portion 13a of well 13. The malaria parasite yields fluorescence when the fluorescent-labeled erythrocytes, which are arrayed in parallel in bottom surface portion 13a while infected with the malaria parasites, are irradiated with the excitation light. The NA (Numerical Aperture) of the fluorescence is larger than the NA of the excitation light as indicated by an alternate long and short dash line in FIG. 3. For this reason, between objective lens 106 and dichroic prism 105, the beam diameter of the fluorescence is larger than the beam diameter of the excitation light. For example, the NA of the fluorescence is 0.65. The wavelength of the fluorescence differs from the wavelength of the excitation light. In the first exemplary embodiment, the fluorescence has a wavelength of 450 nm to 540 nm. On the other hand, the erythrocyte that is not infected with the malaria parasite does not yield the fluorescence because the erythrocyte is not fluorescently labeled. Thus, the erythrocyte infected with the malaria parasite and the erythrocyte not infected with the malaria parasite can be distinguished from each other.

The fluorescence incident from the side of objective lens 106 on dichroic prism 105 is transmitted through dichroic prism 105. Collective lens 109 collects the fluorescence incident from the side of dichroic prism 105, and introduces the fluorescence to fluorescence detector 110. Fluorescence detector 110 includes a sensor that receives the fluorescence on the light receiving surface. A detection signal of fluorescence detector 110 is input to signal amplifying circuit 204.

Signal calculating circuit 201 generates focus error signal FE and tracking error signal TE from the detection signal of photodetector 108, and generates a reproduced RF signal (to be described) from the detection signal of photodetector 108. Servo circuit 202 controls drive of objective lens actuator 122 using focus error signal FE and tracking error signal TE that are output from signal calculating circuit 201. Using the reproduced RF signal output from signal calculating circuit 201, servo circuit 202 controls rotating device 123 such that biosensor substrate 10 is rotated at a constant linear velocity. Reproducing circuit 203 generates reproduced data by demodulating the reproduced RF signal output from signal calculating circuit 201. Signal amplifying circuit 204 amplifies the detection signal of fluorescence detector 110.

Controller 205 controls each unit of fluorescence detection device 1 in addition to signal calculating circuit 201, servo circuit 202, and reproducing circuit 203. Controller 205 determines the position of well 13 in which the fluorescence is detected in biosensor substrate 10 using the reproduced data (address information) output from reproducing circuit 203 and the signal output from signal amplifying circuit 204, and stores the address information corresponding to well 13 in which the fluorescence is detected in an internal memory.

Figure 4:
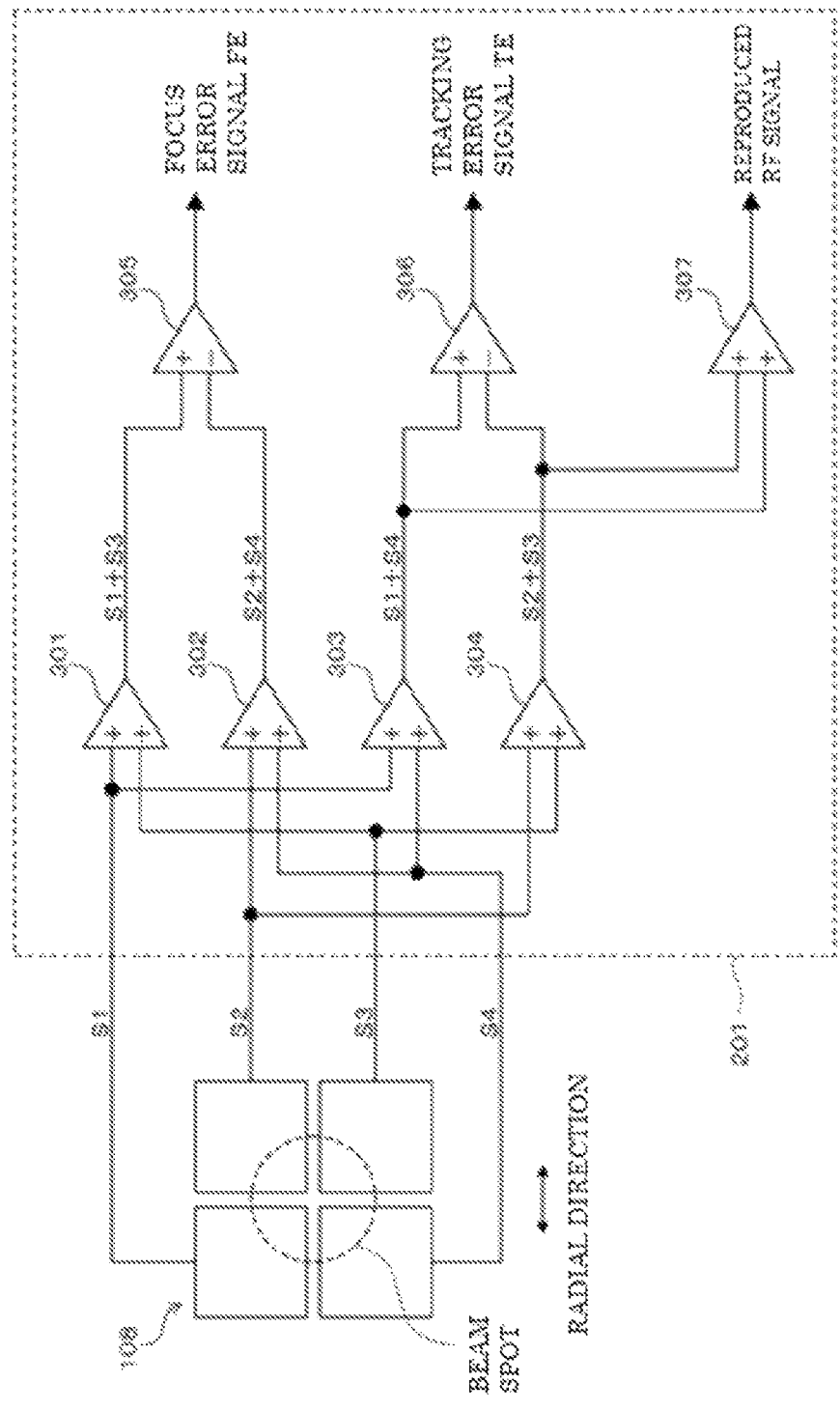
FIG. 4 is a view illustrating a circuit configuration of a signal calculating circuit of the first exemplary embodiment.

FIG. 4 is a view illustrating a circuit configuration of signal calculating circuit 201.

As described above, photodetector 108 includes the quadrant sensor that receives the reflected excitation light on the light receiving surface. Upper left, upper right, lower right, and lower left sensors of the quadrant sensor output detection signals S1 to S4 based on a beam spot of the received reflected excitation light. On the light receiving surface of photodetector 108 in FIG. 4, a right and left direction corresponds to the radial direction of the disk. Focus error signal FE and tracking error signal TE are generated according to an astigmatism method and a one-beam push-pull method that are used in existing optical disk devices.

Signal calculating circuit 201 includes adders 301 to 304 and 307 and subtractors 305 and 306. Adder 301 outputs a signal to which detection signals S1 and S3 are added to subtractor 305, and adder 302 outputs a signal to which detection signals S2 and S4 are added to subtractor 305. Adder 303 outputs a signal to which detection signals S1 and S4 are added to subtractor 306 and adder 307, and adder 304 outputs a signal to which detection signals S2 and S3 are added to subtractor 306 and adder 307.

Subtractor 305 subtracts the output signals of adders 301 and 302, and outputs focus error signal FE. Subtractor 306 subtracts the output signals of adders 303 and 304, and outputs tracking error signal TE. Adder 307 adds the output signals of adders 303 and 304, and outputs reproduced RF signal. That is, focus error signal FE, tracking error signal TE, and the reproduced RF signal can be obtained by calculations of the following equations (1) to (3), respectively.

$$FE = (S1+S3)-(S2+S4) \quad (1)$$

$$TE = (S1+S4)-(S2+S3) \quad (2)$$

$$RF = (S1+S2+S3+S4) \quad (3)$$

At this point, when a focal position of objective lens 106 is located on reflecting surface 11a, the beam spot on the quadrant sensor of photodetector 108 becomes a least circle of confusion, and focus error signal FE of the equation (1) becomes a value of 0. When the focal position of objective lens 106 is located immediately above the track (pit) of reflecting surface 11a, the beam spot on the quadrant sensor of photodetector 108 equally overlaps the two left sensors and the two right sensors, and tracking error signal TE of the equation (2) becomes a value of 0.

FIGS. 5A and 5B are views illustrating a focal depth of the excitation light.

As described above, the excitation light has a wavelength of 405 nm, and the excitation light has a NA (Numerical Aperture) of 0.34. Generally, the focal depth can be calculated from the wavelength/(NA×NA). Therefore, in the first exemplary embodiment, the focal depth of the excitation light becomes about 3.5 μm. Distance d3 between bottom surface portion 13a and reflecting surface 11a in FIGS. 1B and 1C is set so as to be smaller than the focal depth of the excitation light. In this case, distance d3 is set to 2.0 μm.

As described above, when the NA of the excitation light is set, the spot diameter becomes about 1 μm at the focal position. Distance d6 of the track pitch in FIG. 1C is set to 1 μm so as to be substantially equal to the spot diameter.

FIG. 5A illustrates a state in which a lowest point in a range of the focal depth of the excitation light agrees with reflecting surface 11a, and FIG. 5B illustrates a state in which a highest point in the range of the focal depth of the excitation light agrees with bottom surface portion 13a. By adjusting an offset voltage output from servo circuit 202 to objective lens actuator 122, the range of the focal depth of the excitation light can be set to either state in FIGS. 5A and 5B, or a state between the states in FIGS. 5A and 5B.

In the states of FIGS. 5A and 5B, distance d3 between bottom surface portion 13a of well 13 and reflecting surface 11a is 2 μm, and the focal depth of the excitation light is 3.5 μm. Therefore, both bottom surface portion 13a and reflecting surface 11a are included in the range corresponding to the focal depth of the excitation light. Accordingly, the focal position of the excitation light is located on reflecting surface 11a by focus servo, the excitation light is also focused on the sample provided in bottom surface portion 13a.

FIG. 5C illustrates a state in which the lowest point in the range of the focal depth of the excitation light is located between bottom surface portion 13a and reflecting surface 11a. In a usual focus servo operation, when objective lens 106 is driven such that focus error signal FE becomes a value of 0, the focal position of the excitation light is not located as illustrated in FIG. 5C. However, a focus servo signal is supplied to objective lens actuator 122 while a predetermined offset voltage is superimposed thereon, which allows the focal position of the excitation light to be slightly deviated upward to be located as illustrated in FIG. 5C. In this case, similar to FIGS. 5A and 5B, the excitation light is focused on the sample provided in bottom surface portion 13a.

When the range of the focal depth is located as illustrated in FIG. 5A, because the range of the focal depth easily overlaps the erythrocyte, the sample can more accurately be measured compared with the case in FIG. 5B. Even if the focus servo is performed such that the states in FIGS. 5A to 5C are obtained, the focal position of the excitation light is slightly deviated in a vertical direction due to a following characteristic of the focus servo and flatness of biosensor substrate 10. However, because the vertical deviation of the focal position is usually constrained within several hundred nanometers, measurement accuracy of the sample does not become troublesome.

Thus, in the first exemplary embodiment, the sample can be irradiated with the excitation light while the excitation light is focused on the sample without spreading, and irradiation efficiency of the sample with the laser beam can be enhanced.

According to the first exemplary embodiment, as illustrated in FIGS. 5A to 5C, bottom surface portion 13a of well 13 is located within the range of the focal depth defined by the excitation light and objective lens 106. Therefore, the focal position of objective lens 106 is located with respect to the sample provided in bottom surface portion 13a, so that the irradiation efficiency of the sample with the excitation light can be enhanced to accurately measure the sample.

According to the first exemplary embodiment, one semiconductor laser 101 is used as the light source for the laser beam that excites the sample and the laser beam that is used to follow the track, so that the optical system can be simplified to achieve the decreased number of components and cost reduction. The compact optical system can be formed.

According to the first exemplary embodiment, the excitation light is focused on the sample when focused on reflecting surface 11a. That is, because the excitation light is directly focused on the sample, the excitation light can more securely be focused on the sample compared with the case that the sample exciting laser beam is indirectly focused on the sample by controlling the objective lens using the servo laser beam like PTL 2.

According to the first exemplary embodiment, the spot diameter of the excitation light is set to 1 μm at the focal position of objective lens 106, and the track pitch formed on reflecting surface 11a is set to 1 μm. On the other hand, a nucleus of the malaria parasite yields a fluorescent bright spot having a size of about 1 μm with the excitation light. Accordingly, the sample is scanned with the spot of the excitation light without any gap while the spot of the excitation light is caused to converge to the size of the nucleus of the malaria parasite, so that the nucleus of the malaria parasite can surely be detected. The position where the malaria parasite is detected is understood from the address information based on the detection signal of photodetector 108, so that well 13 in which the detected malaria parasite is accommodated can easily be recognized.

<First Modification>

Figure 6:
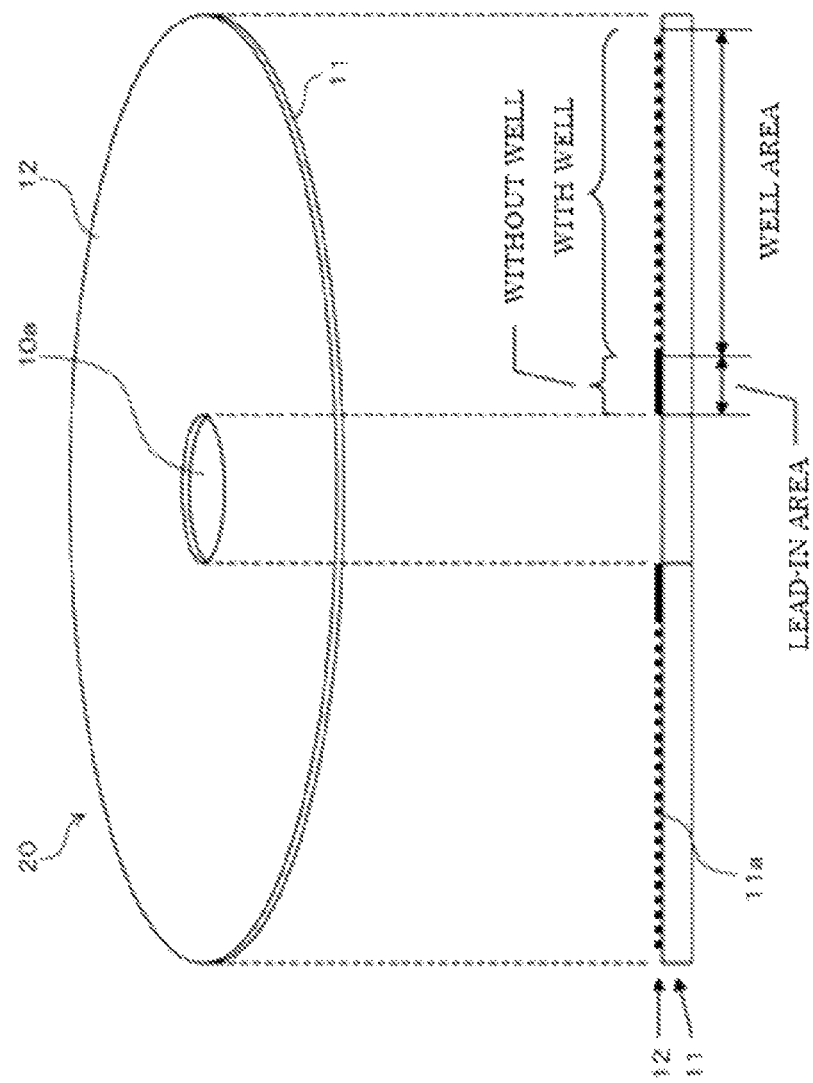
FIG. 6 is a view schematically illustrating a configuration of a biosensor substrate according to a first modification.

FIG. 6 is a view schematically illustrating a configuration of biosensor substrate 20 according to a first modification of the first exemplary embodiment. Unlike biosensor substrate 10 in FIGS. 1A to 1C, biosensor substrate 20 is radially divided into a lead-in area and a well area. Well 13 is formed not in well layer 12 of the lead-in area on the inner circumferential side, but only in the well area on the outer circumferential side. Similar to the first exemplary embodiment, the pits are formed in a whole area from the lead-in area to the well area. That is, the track constructed with the pit strings extends spirally from the innermost circumference of the lead-in area to the outermost circumference of the well area.

In the first modification, similar to the first exemplary embodiment, the address information is held by the pit strings. In addition to the address information, information on biosensor substrate 20 is also held by the pit strings in the lead-in area. Specifically, information including distance d3 between bottom surface portion 13a of well 13 and reflecting surface 11a of biosensor substrate 20 is stored in the lead-in area. Other configurations of biosensor substrate 20 are substantially identical to those of biosensor substrate 10.

The reason why well 13 is not formed in the lead-in area is as follows. The first reason is that the information formed in the lead-in area on reflecting surface 11a can be reproduced (obtained) well compared with the case that well 13 exists.

The second reason is that, compared with the case that well 13 exists, the sample flows uniformly into well 13 for the flat upper surface of well layer 12 corresponding to the lead-in area, when the sample is dropped inside biosensor substrate 20 to flow into well 13 while biosensor substrate 20 is slowly rotated.

Figure 7:
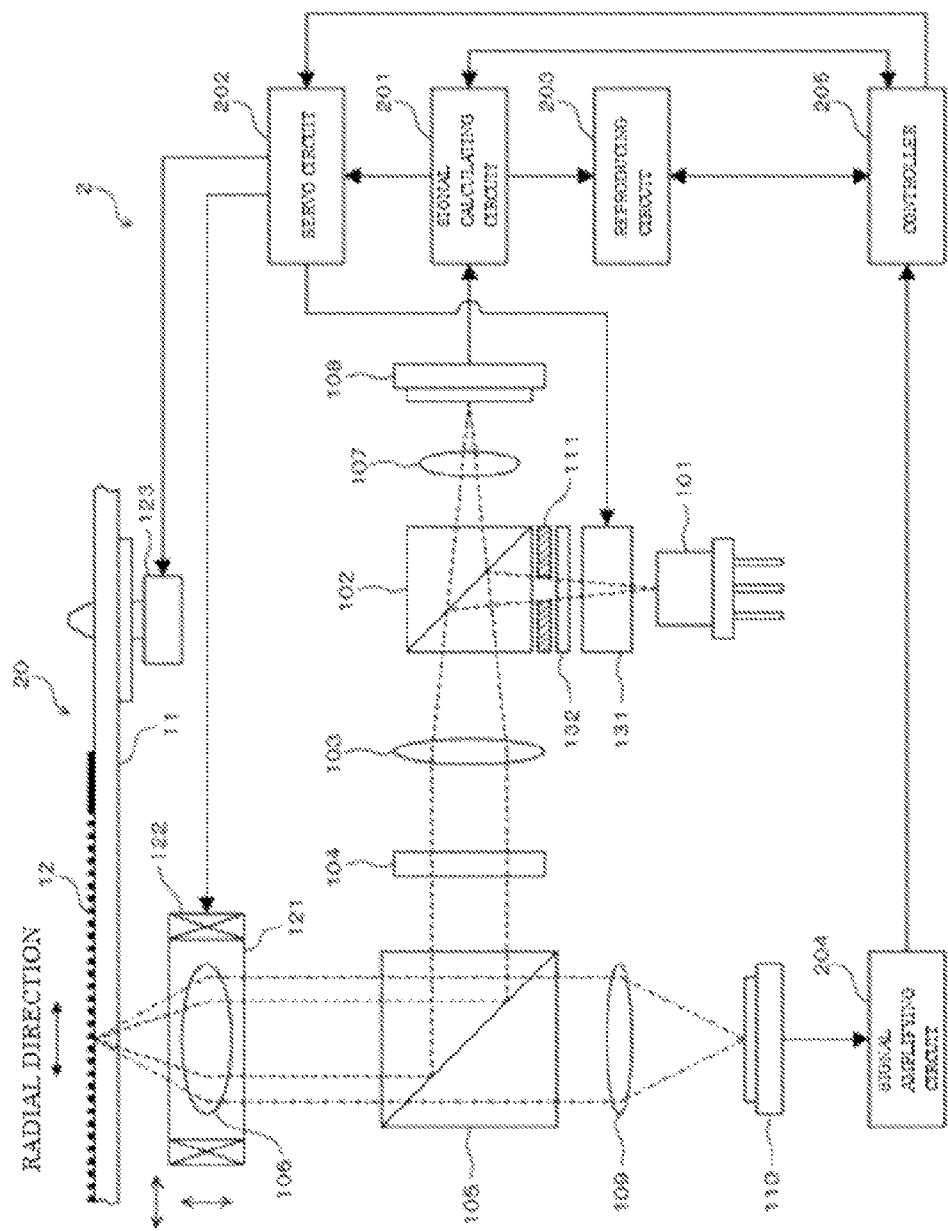
FIG. 7 is a view illustrating a configuration of a fluorescence detection device of the first modification.

FIG. 7 is a view illustrating a configuration of fluorescence detection device 2 of the first modification.

Fluorescence detection device 2 differs from fluorescence detection device 1 in FIG. 3 in that opening restricting element 131 and polarizing filter 132 are arranged between semiconductor laser 101 and aperture 111. Opening restricting element 131 is controlled by servo circuit 202.

Figure 8B:
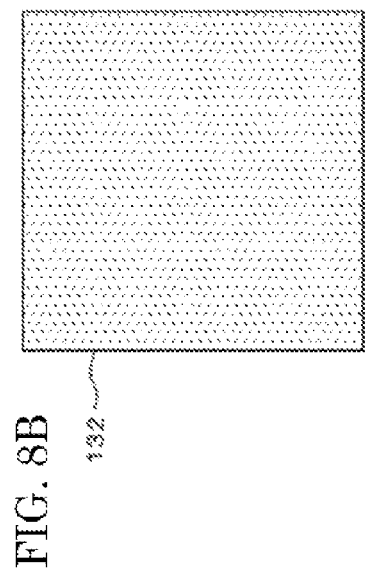
FIGS. 8A and 8B are views illustrating an opening restricting element and a polarizing filter when the opening restricting element and the polarizing filter are viewed in an optical axis of the excitation light.
Figure 8A:
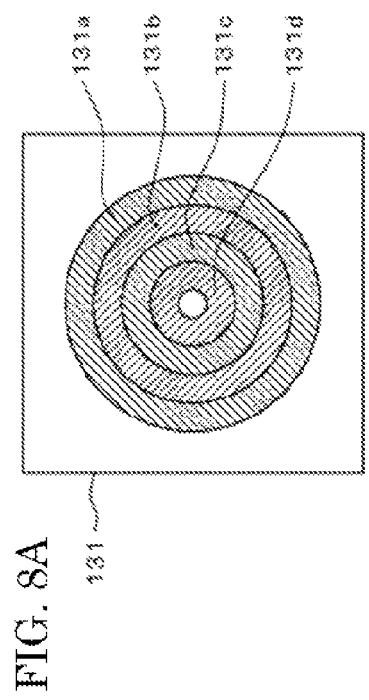

FIGS. 8A and 8B are views illustrating opening restricting element 131 and polarizing filter 132 when opening restricting element 131 and polarizing filter 132 are viewed in an optical axis direction of the excitation light emitted from semiconductor laser 101.

Opening restricting element 131 is made of TN-type liquid crystal, and transparent electrodes are provided at positions corresponding to four areas 131a to 131d having concentric boundaries such that voltages can separately be applied to areas 131a to 131d. When the voltages are applied to areas 131a to 131d, polarization direction of the excitation light incident on the area to which the voltage is applied rotates by 90 degrees. Opening restricting element 131 is arranged such that centers of areas 131a to 131d are aligned with outgoing optical axis of semiconductor laser 101. The excitation light passing through area 131a is not blocked by aperture 111, but the excitation light passing through the outside of area 131a is blocked by aperture 111.

Polarizing filter 132 blocks the excitation light in which the polarization direction rotates by 90 degrees by applying the voltage to areas 131a to 131d, and polarizing filter 132 transmits the excitation light in which the polarization direction does not rotate by not applying the voltage to areas 131a to 131d.

Figure 8D:
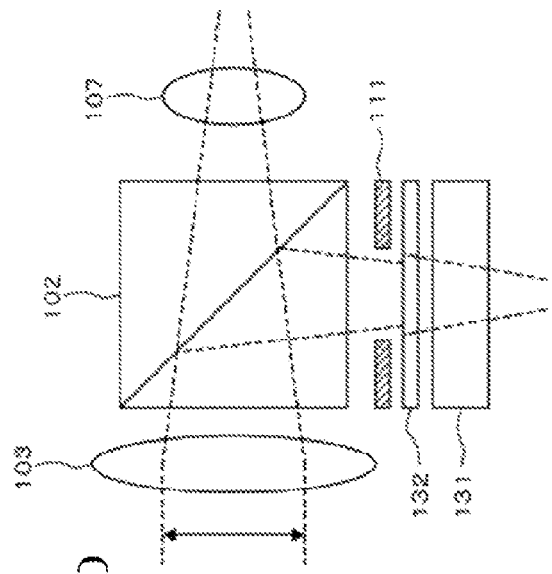
FIGS. 8C and 8D are schematic diagrams illustrating the excitation light according to a state of the opening restricting element.
Figure 8C:
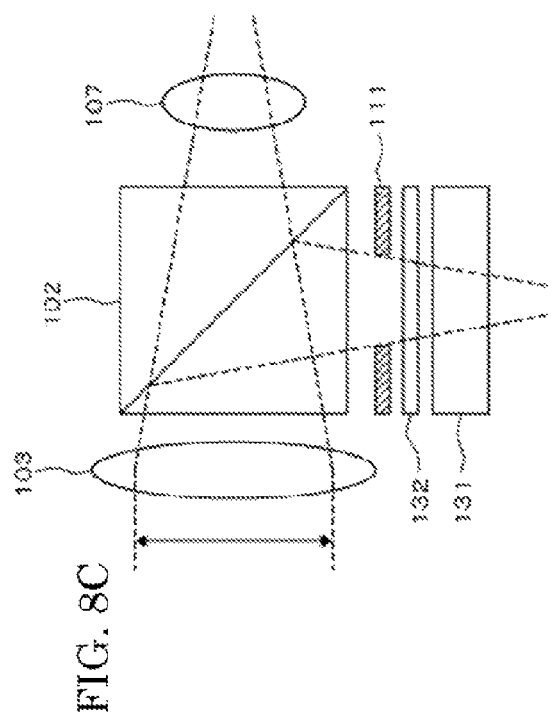

FIG. 8C is a schematic diagram illustrating the excitation light when the voltages are not applied to all areas 131a to 131d of opening restricting element 131. In this case, the beam diameter of the excitation light is equal to that of the first exemplary embodiment (see FIG. 3). Therefore, the NA (Numerical Aperture) of the excitation light caused to converge by objective lens 106 becomes 0.34 similar to the first exemplary embodiment.

FIG. 8D is a schematic diagram illustrating the excitation light when the voltages are applied to an outside of opening restricting element 131, for example, areas 131a and 131b. The polarization direction of the excitation light, which is emitted from semiconductor laser 101 and is incident on areas 131a and 131b, rotates by 90 degrees, and is blocked by polarizing filter 132. In this case, the beam diameter of the excitation light passing through collimator lens 103 is smaller than that in FIG. 8C. Therefore, the beam diameter of the excitation light incident from the side of dichroic prism 105 on objective lens 106 decreases, and the NA (Numerical Aperture) of the excitation light caused to converge by objective lens 106 becomes smaller than the NA of 0.34 in FIG. 8C.

The NA (Numerical Aperture) of the excitation light caused to converge by objective lens 106 can be decreased by decreasing the beam diameter of the excitation light. As described above, the focal depth can be calculated from wavelength/(NA×NA). Therefore, by decreasing the beam diameter of the excitation light, the focal depth of the excitation light can be decreased compared with the first exemplary embodiment.

In the first modification, polarizing filter 132 can be eliminated. In this case, because the excitation light in which the polarization direction is rotated by 90 degrees by opening restricting element 131 becomes the P-polarized light with respect to PBS 102, the excitation light is transmitted through PBS 102, but not introduced to collimator lens 103. That is, PBS 102 exerts the action identical to that of polarizing filter 132. Therefore, for example, when the voltages are applied to areas 131a and 131b of opening restricting element 131, the beam diameter of the excitation light reflected onto the side of collimator lens 103 decreases, and the focal depth of the excitation light can be changed similar to the case that polarizing filter 132 is provided. In this configuration, desirably polarizing filter 132 is provided as described above in the case that the excitation light transmitted through PBS 102 becomes noise light in fluorescence detection device 2 to generate a problem in the fluorescence detection.

FIG. 9A is a flowchart illustrating an operation to drive opening restricting element 131 by controller 205.

When biosensor substrate 20 is set (YES in S1), controller 205 moves objective lens 106, and irradiates the lead-in area with the excitation light to read the lead-in area (S2). At this point, based on the excitation light reflected from the lead-in area, controller 205 acquires distance d3 between bottom surface portion 13a of well 13 and reflecting surface 11a of biosensor substrate 20 from the reproduced data output from reproducing circuit 203.

Then, controller 205 refers to a table previously stored in the memory of controller 205, and acquires the voltage applying area from the table (S3). As illustrated in FIG. 9B, the area of opening restricting element 131 to which the voltage should be applied according to the distance between bottom surface portion 13a and reflecting surface 11a is stored in the table. Five ranges are set as the distance between bottom surface portion 13a and reflecting surface 11a, and five driving patterns indicating the area to which the voltage should be applied are correlated with the five ranges. In the case that the distance between bottom surface portion 13a and reflecting surface 11a is D0 to D1, the voltages are not applied to the areas.

Then, controller 205 controls opening restricting element 131 according to the voltage applying area acquired in S3, and applies the voltage to the corresponding area (S4). Therefore, the beam diameter of the excitation light incident from the side of dichroic prism 105 on objective lens 106 changes to set the NA suitable for biosensor substrate 20. The focal depth of the excitation light is set to one that covers the distance d3 of biosensor substrate 20. The processing returns to S1 unless fluorescence detection device 2 is shut down (S5).

According to the first modification, distance d3 between bottom surface portion 13a and reflecting surface 11a is written in the lead-in area of biosensor substrate 20. When biosensor substrate 20 is changed, distance d3 can be changed. In the first modification, distance d3 applied to biosensor substrate 20 is held in the lead-in area of biosensor substrate 20. Controller 205 reads distance d3 from the lead-in area, and drives opening restricting element 131 based on read distance d3 and the table in FIG. 9B. Therefore, the NA of the excitation light is properly set in biosensor substrate 20, and the range of the focal depth of the excitation light is adjusted so as to be larger than distance d3 between bottom surface portion 13a and reflecting surface 11a of biosensor substrate 20. Therefore, similar to the case in FIGS. 5A to 5C, bottom surface portion 13a is located within the range of the focal depth defined by the excitation light and objective lens 106, so that the sample can accurately be measured.

The driving pattern (for example, the driving pattern for distance D0 to D1) of a default setting in the five driving patterns is used, in the case that distance d3 read from the lead-in area is not included in the range of the distance in FIG. 9B, or in the case that distance d3 cannot be read from the lead-in area. In areas 131a to 131d, because an amount of blocked excitation light increases with increasing number of driving areas, the amount of excitation light with which the sample is irradiated decreases. Therefore, for example, the driving pattern at the top stage in FIG. 9B, namely, the driving pattern in which the voltages are not applied to the areas is used as the driving pattern of the default setting such that the amount of excitation light with which the sample is irradiated increases as much as possible.

In the first modification, distance d3 between bottom surface portion 13a and reflecting surface 11a is held in the lead-in area of biosensor substrate 20. Alternatively, the NA (Numerical Aperture) of the excitation light, a kind (size) of the cell, or another parameter value that can define the focal depth suitable for distance d3 may be held in the lead-in area of biosensor substrate 20. In this case, the left field of the table in FIG. 9B is corrected so as to correspond to another parameter value.

Figure 10:
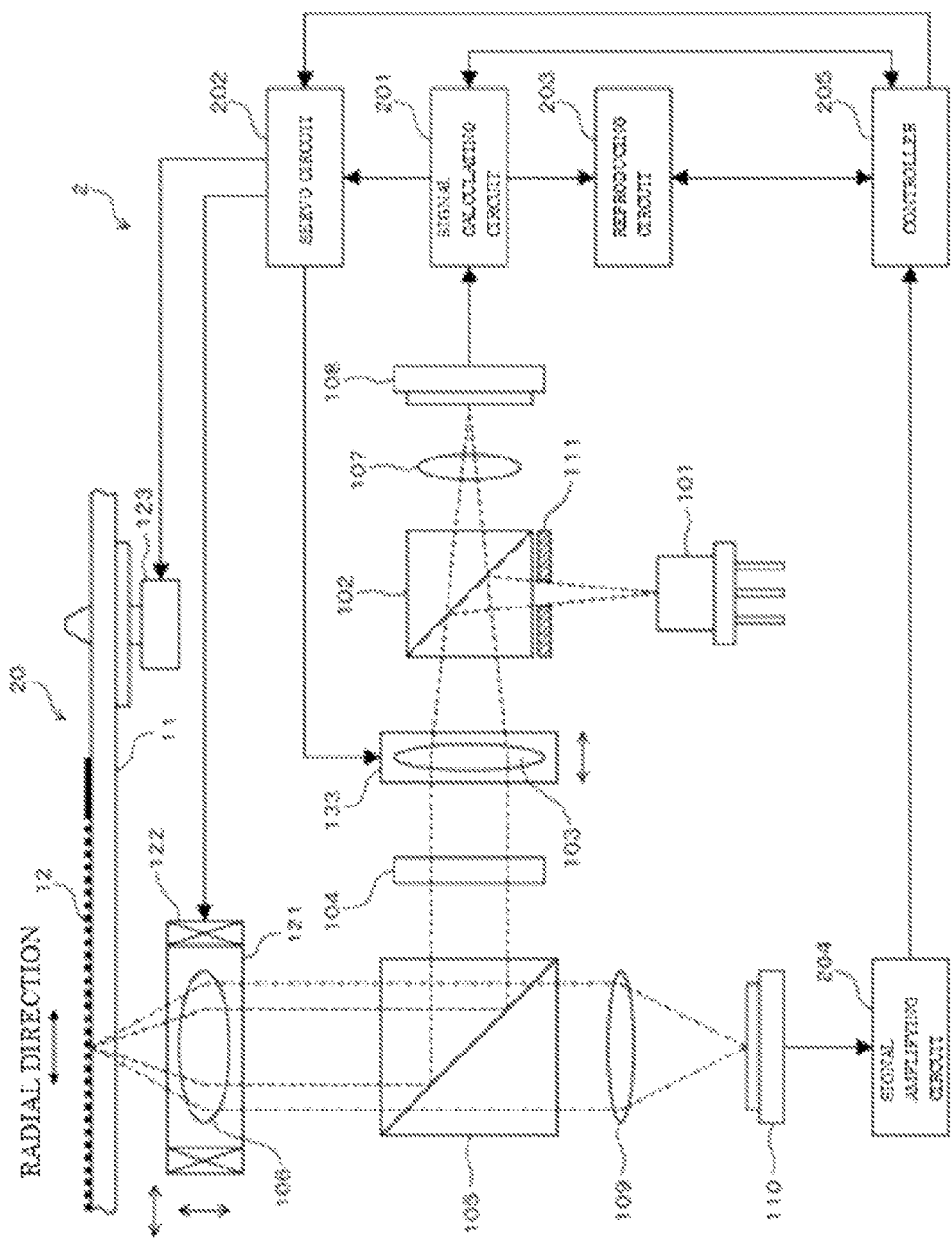
FIG. 10 is a view illustrating a fluorescence detection device according to a second modification.

In the first modification, opening restricting element 131 and polarizing filter 132 are used to adjust the beam diameter of the excitation light incident on objective lens 106. In a second modification, lens actuator 133 may be used as illustrated in FIG. 10. Lens actuator 133 moves collimator lens 103 in the optical axis direction of the excitation light using servo circuit 202.

In this case, when collimator lens 103 is driven, a spread angle of the excitation light incident from the side of dichroic prism 105 on objective lens 106 changes, and therefore the numerical aperture of the excitation light caused to converge by objective lens 106 changes. Therefore, the focal depth of the excitation light is adjusted. In the second modification, the focal depth of the excitation light is linearly changed according to the movement of collimator lens 103, so that the focal depth can more finely be adjusted compared with the first exemplary embodiment. In the second modification, the right field of the table in FIG. 9B is changed to a driving voltage supplied to lens actuator 133. Additionally, the focal depth is linearly adjusted, the left field of the table is finely segmented in a stepwise manner, and the range of distance d3 in one segment is more finely set. Therefore, compared with the first modification in FIG. 7, the focal depth suitable for distance d3 of biosensor substrate 20 can be set to more accurately measure the sample.

Second Exemplary Embodiment

A second exemplary embodiment of the present invention will be described below with reference to the drawings.

<Biosensor Substrate>

Figure 11A:
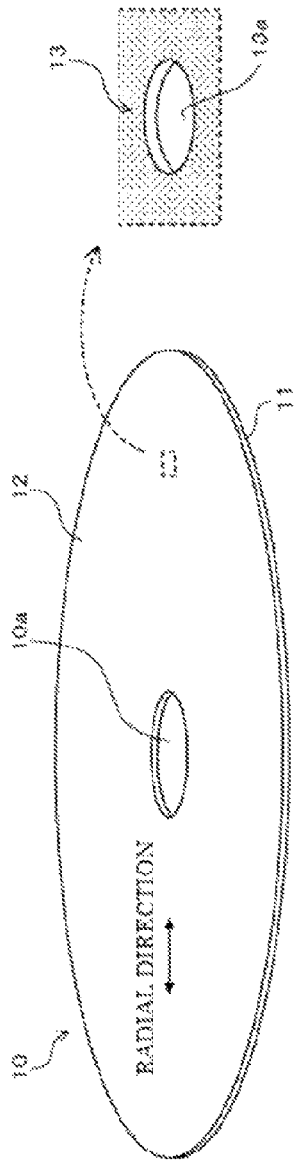
FIG. 11A is a perspective view schematically illustrating an appearance configuration of a biosensor substrate according to a second exemplary embodiment.

FIG. 11A is a perspective view schematically illustrating an appearance configuration of biosensor substrate 10 according to the second exemplary embodiment. For example, biosensor substrate 10 is used to detect an erythrocyte infected with a malaria parasite in human blood.

Biosensor substrate 10 has a disc shape similar to an optical disk (such as a CD and a DVD), and circular hole 10a is made in the center of biosensor substrate 10. Biosensor substrate 10 has a structure in which well layer 12 is stacked on an upper surface of base substrate 11. As illustrated in an enlarged view at the right end of FIG. 11A, plural micro wells 13 constructed with columnar voids are formed in well layer 12. Wells 13 are substantially concentrically arrayed from the inner circumference toward the outer circumference of biosensor substrate 10. Well 13 includes bottom surface portion 13a lower than a upper surface of well layer 12, and a diameter and a height of well 13 are set such that a sample is accommodated in well 13 when dropped into well 13.

Figure 11B:
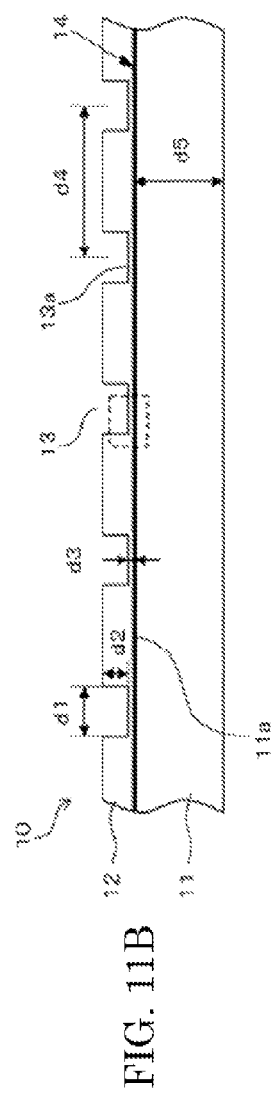
FIG. 11B is a sectional view of the biosensor substrate when the biosensor substrate is cut in a plane perpendicular to a surface of the biosensor substrate.
Figure 11C:
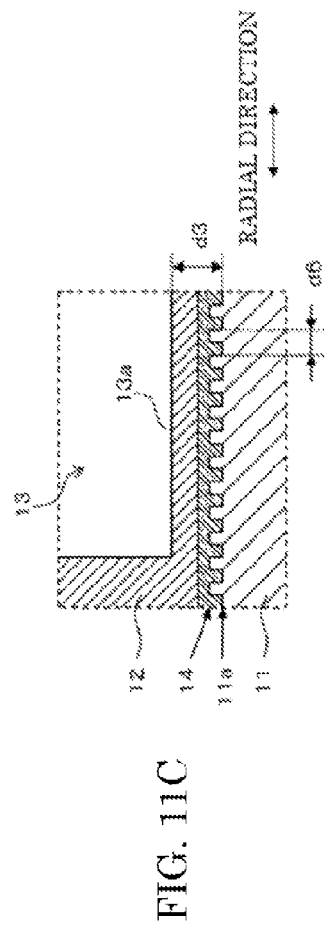
FIG. 11C is a partially enlarged view illustrating the section of the biosensor substrate.

FIG. 11B is a sectional view of biosensor substrate 10 when biosensor substrate 10 is cut in the plane perpendicular to the surface of biosensor substrate 10, and FIG. 11C is an enlarged view of a broken-line portion in FIG. 11B.

Similar to the optical disk, a spiral track (pit strings) is formed on an upper side (the side of well layer 12) of base substrate 11. The pit holds address information in order to identify a position on the surface of biosensor substrate 10. Similar to the CD and the DVD, the track is scanned with excitation light (to be described) at a constant linear velocity to reproduce the address information. Reflecting film 14 is provided between base substrate 11 and well layer 12. Reflecting surface 11a that is of an interface between reflecting film 14 and base substrate 11 is formed on the upper surface of base substrate 11 by stacking reflecting film 14 on the upper surface of base substrate 11. Wells 13 are formed at predetermined intervals on the upper surface side of well layer 12. Bottom surface portion 13a of well 13 is located slightly higher than reflecting film 14, and bottom surface portion 13a of well 13 separates from the upper surface of reflecting film 14.

At this point, it is assumed that d1 and d2 are the diameter and the height of well 13, that d3 is a distance between bottom surface portion 13a and reflecting surface 11a, that d4 is the interval between wells 13, that d5 is a thickness of base substrate 11, and that d6 is a track pitch of reflecting surface 11a. In the second exemplary embodiment, diameter d1 is set to 100 μm, height d2 is set to 50 μm, distance d3 is set to 2 μm, interval d4 is set to 300 μm, thickness d5 is set to 0.6 mm, and track pitch d6 is set to 1 μm. Reflecting film 14 has a reflectance of 3% to 4% for the excitation light (to be described).

Track pitch d6 may be adjusted according to the size of the subject that is of the fluorescence detection target. In the second exemplary embodiment, because the erythrocyte that is of the subject has a diameter of about 10 μm, track pitch d6 is set to 1 μm such that the track surely traverses the subject when the sample is accommodated in well 13. That is, it is necessary that the track pitch be set smaller than a width of the subject that is of the fluorescence detection target. However, time necessary to scan the whole area of biosensor substrate 10 is lengthened with decreasing track pitch. Accordingly, in the case that track pitch d6 is smaller than the size of the subject, track pitch d6 may be set to an extent that the track traverses each subject at least one time even if the size of the subject varies.

In the second exemplary embodiment, base substrate 11 is made of polycarbonate, well layer 12 is made of an ultraviolet curing resin, and reflecting film 14 is made of metal such as aluminum and a silver alloy, niobium oxide, or a wavelength selection film. Instead of polycarbonate, base substrate 11 may be made of polymethylmethacrylate or amorphous polyolefin. Well layer 12 may be made of silicone, polycarbonate, polymethylmethacrylate, and amorphous polyolefin. For example, the thickness of reflecting film 14 is set to 5 nm to 20 nm such that the desired reflectance is obtained.

FIGS. 12A and 12B are views illustrating a method for segmenting a track of the second exemplary embodiment.

As illustrated in FIG. 12A, the area on biosensor substrate 10 is radially segmented into m zones from the inner circumference toward the outer circumference. Each zone is set into a substantially concentric shape. The radial widths of the zones are equal to one another. That is, the radial width of each zone becomes the width corresponding to n track pitches (n ×track pitch).

FIG. 12B is an enlarged view of a broken-line area in FIG. 12A. For the sake of convenience, the tracks of zones 1 and 3 are indicated by solid lines, and the tracks of zone 2 are indicated by broken lines. The track is constructed with the pit strings.

At this point, as illustrated in FIG. 12A, one diameter of biosensor substrate 10 is set to reference diameter D0. In this case, as illustrated in FIG. 12B, assuming that one track piece is the track that makes one revolution from the position of reference diameter D0, each zone includes n track pieces when a number of track pieces is counted in each zone. A starting end of the track piece (track 1) in the innermost circumference of zone 2 is connected to a terminal end of the inside track piece (track n) of zone 1 at the position of reference diameter D0. For other zones, similarly the starting end of the track piece (track 1) in the innermost circumference is connected to the terminal end of the inside track piece (track n) of zone 1 at the position of reference diameter D0. As described above, the n track pieces are included in each zone. For example, the radial width of each zone is set to 300 μm.

Figure 13:
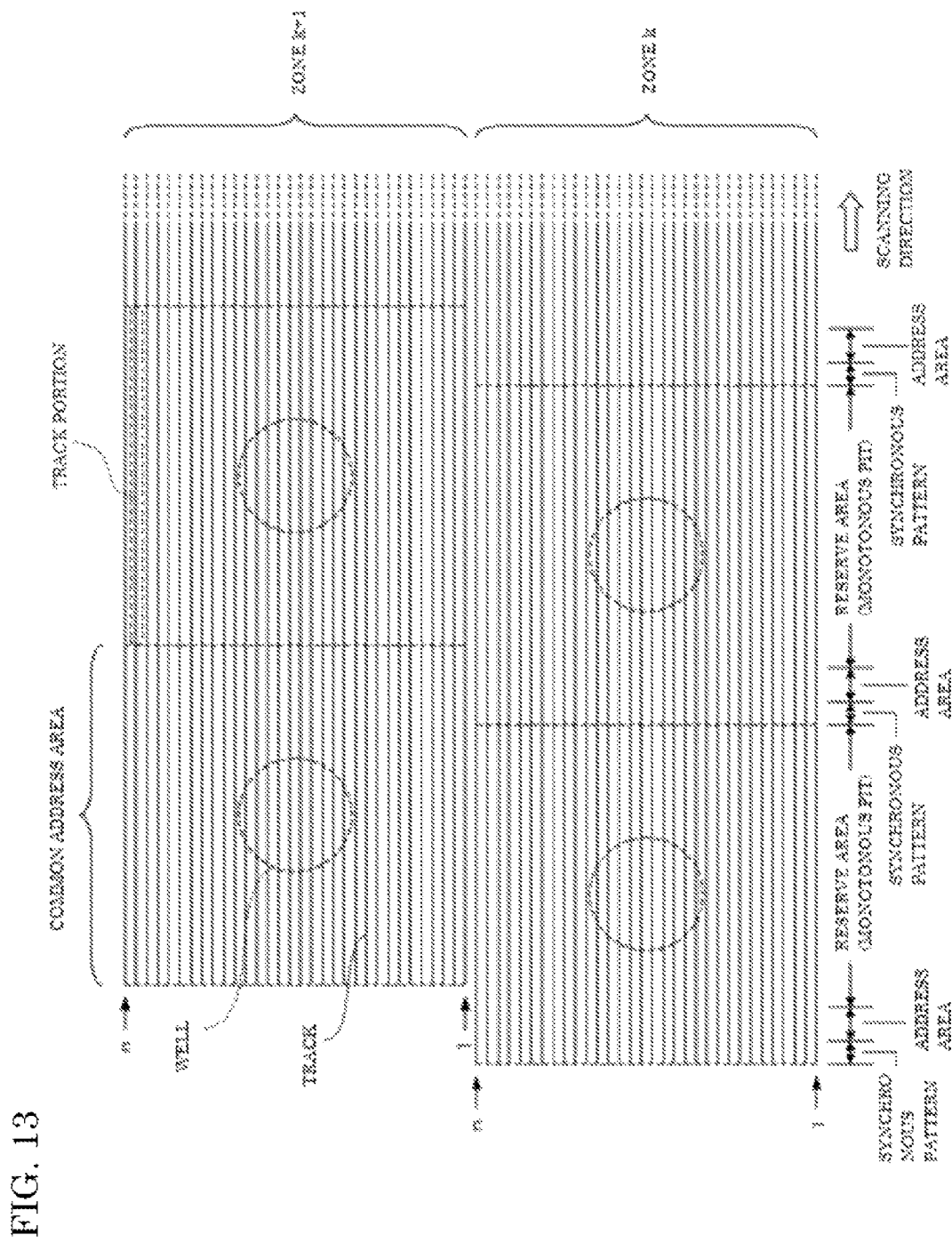
FIG. 13 is a view illustrating a method for setting a common address area of the second exemplary embodiment.

FIG. 13 is a view illustrating a method for setting a common address area of the second exemplary embodiment.

Each zone set in the above manner is equally segmented into a predetermined number of pieces in the circumferential direction such that a circumferential width becomes a predetermined length (for example, 300 μm). The area formed by segmenting the zone becomes the common address area.

The square common address area is illustrated in FIG. 13. However, strictly the common address area has a pseudo-trapezoidal shape in which the disk inner circumferential side is shorter than the disk outer circumferential side. That is, because the common address area is formed by equally segmenting the ring-like zone in the circumferential direction, the common address area has the shape in which the ring is cut at each predetermined angles. Accordingly, the n track portions included in the one common address area is lengthened toward the disk outer circumference.

Because the common address area is set by equally segmenting the zone in the circumferential direction, the shapes of the common address areas included in the identical zone are identical to one another. However, the circumferential width of the common address area can vary depending on the zone. For example, assuming that L is a length of one revolution of the outermost track of the zone, the circumferential width of the outermost track portion of the common address area is a value in which a quotient of L/j (j is a natural number other than 0) comes closest to 300 μm. In this case, the zone is circumferentially segmented into j pieces. Because the circumferential width of the common address area is decided by segmenting the zone into the j pieces, the circumferential width of the common address area can vary depending on the zone. A number of segmented pieces j of the zone depends on the zone, and the number of segmented pieces j increases toward the outside zone. A boundary between the common address areas circumferentially adjacent to each other agrees with a predetermined diameter of the disk.

The radial width of the common address area, namely, the radial width of the zone depends on a number of track pieces n included in the zone. In the second exemplary embodiment, because of the track pitch of 1 μm, one common address area includes 300 track portions in the case that the common address area has a radial width of 300 μm.

Figure 14:
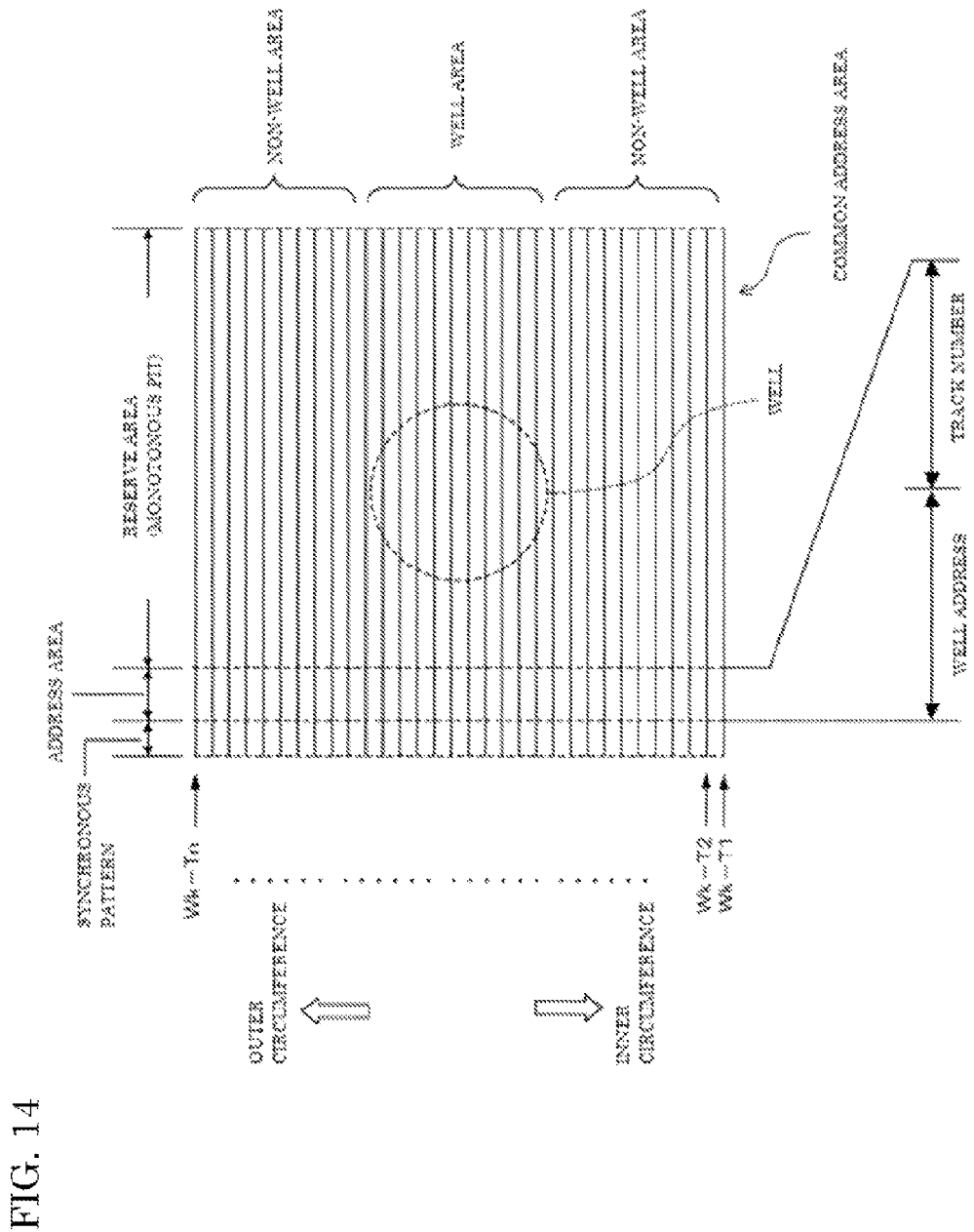
FIG. 14 is a view illustrating a method for setting a synchronous area, an address area, a reserve area, a well area, and a non-well area with respect to the common address area of the second exemplary embodiment and a structure of data held in the address area.

FIG. 14 is a view illustrating a method for setting a synchronous area, an address area, a reserve area, a well area, and a non-well area with respect to the common address area and a structure of data held in the address area.

As illustrated in FIG. 14, in a physical format of each track portion included in the common address area, a unique synchronous pattern is provided at a head, and the address area and the reserve area follow the synchronous pattern. The address information is held in the address area. The address information includes a well address and a track number. The well address is positional information identifying the position of the well on biosensor substrate 10, and the track number is information distinguishing one track portion from other track portions in a group of track portions included in the common address area.

The well addresses held in the track portions included in one common address area are identical to one another. In FIG. 14, all the well addresses held in the track portions included in one common address area are unified to Wk (a kth well from a starting position). For the track number, the track number of the track portion on the innermost circumferential side in the track portions included in the common address area is set to 1, and the track number of the track portion is incremented by 1 toward the outer circumferential side. In FIG. 14, the innermost circumferential track portion has track number T1 of 1, and the outermost circumferential track portion has track number Tn of 300. A pit and a space are formed with a monotonous width in the reserve area in order to generate a clock. Because the length of the track portion included in one common address area is lengthened toward the outer circumference, the length (a number of pits included in the reserve area) of the reserve area is also lengthened toward the outer circumference. Alternatively, the reserve area is not constructed with the monotonous pit strings, but predetermined information may be held in the reserve area.

One well is arranged in the center of the common address area. In the second exemplary embodiment, because the well has a diameter of 100 μm, the common address area is sufficiently wider than the well. Therefore, even if the arrangement position of the well is slightly deviated with respect to the common address area during the formation of the well, the well is accommodated in the common address area.

Because the common address area is sufficiently wider than the well, the non-well area in which the well does not exist is generated in the common address area. Even if the track included in the radially-generated non-well area is scanned with the excitation light (to be described), the excitation light does not overlap the well, the scanning becomes wasted. In the second exemplary embodiment, as described later, a measure is taken on the fluorescence detection device side in order to avoid the wasted scan.

In the second exemplary embodiment, the zone is equally segmented in the circumferential direction to set the common address area. Alternatively, the circumferential width of the common address area may previously be fixed to continuously allocate the common address areas included in each zone in the circumferential direction of the zone. In this case, possibly an excess area in which the circumferential width is not enough to allocate the common address area is generated in the zone. The excess area can be filled with the monotonous pit string.

FIGS. 15A to 15D are views illustrating a method for producing biosensor substrate 10. As described below, the method in FIGS. 15A to 15D is substantially identical to the method for producing the optical disk.

As illustrated in FIG. 15A, base substrate 11 is formed by injection molding. Therefore, base substrate 11 has thickness d5, and a string of pits is formed on the upper surface of base substrate 11. As illustrated in FIG. 15B, reflecting film 14 is evaporated on the upper surface of base substrate 11, thereby forming reflecting surface 11a on the upper surface of base substrate 11. As illustrated in FIG. 15C, bottom layer 12a is stacked on the upper surface of reflecting film 14 by spin coating. As illustrated in FIG. 15D, top layer 12b having thickness d2 is formed on the upper surface of bottom layer 12a by photo-polymer molding. Therefore, plural wells 13 as shown in FIG. 11B are formed. Well layer 12 is formed by combining bottom layer 12a and top layer 12b.

In the case that top layer 12b is formed on the upper surface of bottom layer 12a by the photo-polymer molding, as described above, it is necessary to properly arrange the stamper (well stamper) used in the photo-polymer molding with respect to base substrate 11 such that well 13 is arranged in the center portion of the common address area.

FIGS. 16A and 16B are views illustrating a method adjusting the position of well stamper WS with respect to base substrate 11.

In the position adjusting method, two micro diffraction areas M1 constituting markers during the position adjustment are formed in base substrate 11 at symmetrical positions with respect to the center of base substrate 11. During the injection molding, a diffraction pattern is formed in the outer circumferential area where the pit is not formed on the upper surface of base substrate 11, thereby providing diffraction areas M1. In well stamper WS, two micro diffraction areas M2 constituting markers are formed at positions corresponding to diffraction areas M1. When base substrate 11 is properly located, two laser light sources are arranged at positions where the laser beams are incident on two diffraction areas M1, and the laser light sources emit the laser beams upward. Light sensors LS are arranged at positions where the laser beams (diffracted light) diffracted by diffraction areas M1 and M2 are received.

During the photo-polymer molding, as illustrated in FIG. 16A, the circumferential position of base substrate 11 is adjusted such that the pieces of diffracted light generated by two diffraction areas M1 are received by light sensors LS. At this point, part (0-order diffracted light: non-diffracted light) of the laser beam is not diffracted by diffraction area M1, but is directly transmitted through diffraction area M1. Then, well stamper WS is brought close to the upper surface of base substrate 11, and the circumferential position of well stamper WS is adjusted such that the pieces of non-diffracted light transmitted through diffraction areas M1 are incident on diffraction areas M2. That is, the circumferential position of well stamper WS is adjusted such that the pieces of diffracted light generated by the incidence of the pieces of non-diffracted light on two diffraction areas M2 are received by light sensors LS. Well stamper WS is pressed against the upper surface of base substrate 11 while the positions of base substrate 11 and well stamper WS are adjusted. At this point, well stamper WS is irradiated with an ultraviolet ray, and the ultraviolet curing resin is cured to form top layer 12b.

The positioning between base substrate 11 and well stamper WS may be performed by another method. For example, a projection and a recess may be provided in well stamper WS and base substrate 11, and the positioning between base substrate 11 and well stamper WS may be performed by fitting the projection into the recess.

<Fluorescence Detection Device>

Figure 17:
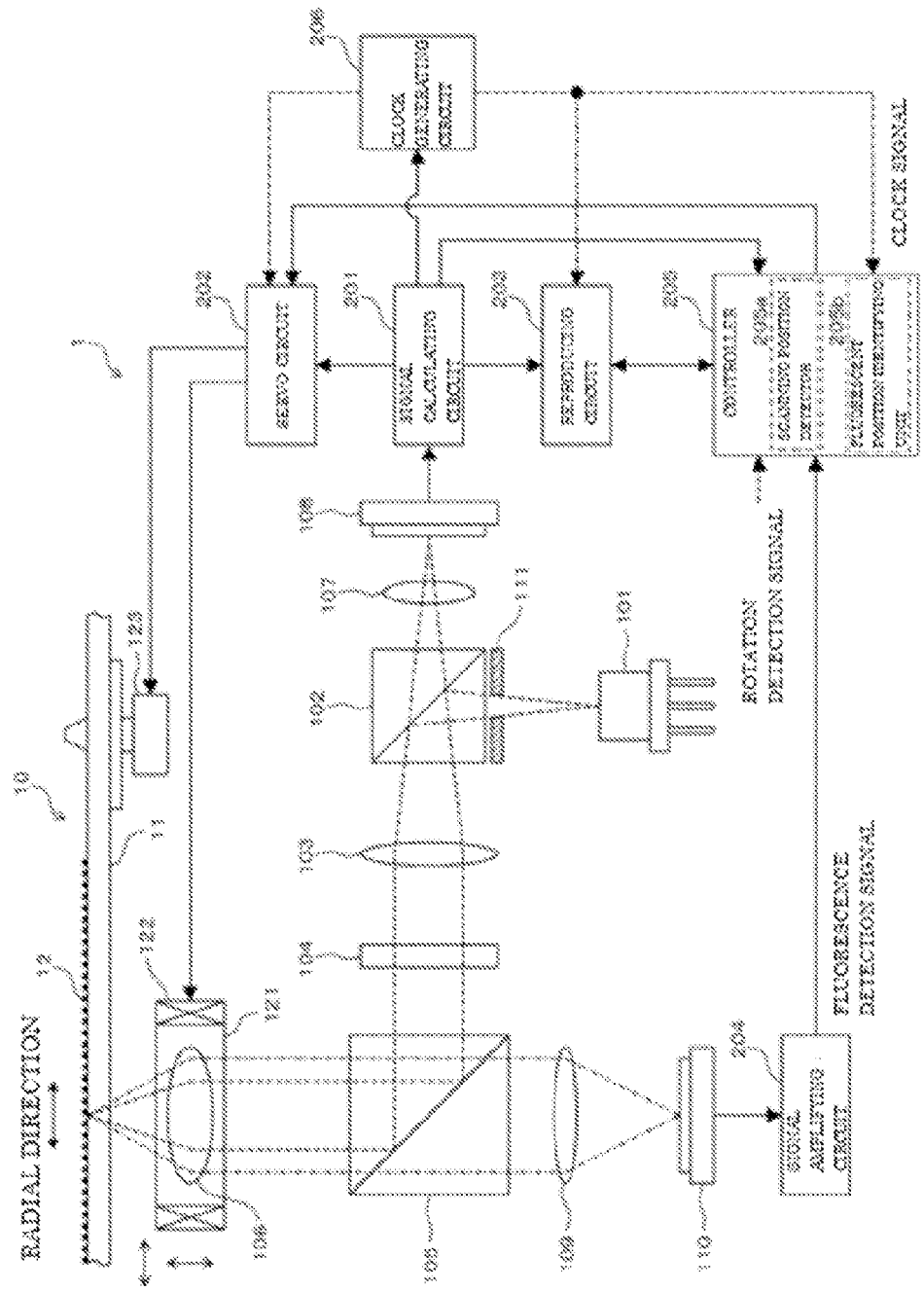
FIG. 17 is a view illustrating a configuration of a fluorescence detection device of the second exemplary embodiment.

FIG. 17 is a view illustrating a configuration of fluorescence detection device 1 of the second exemplary embodiment. For example, fluorescence detection device 1 is used to determine whether the erythrocyte accommodated in well 13 of biosensor substrate 10 is infected with the malaria parasite.

In the use of fluorescence detection device 1, the sample produced by fluorescently labeling the subject is previously accommodated in well 13 of biosensor substrate 10. In the second exemplary embodiment, in the case that the erythrocyte that is of the subject having a diameter of about 10 μm and a thickness of about 2 μm is infected with the malaria parasite, the inside of the erythrocyte is fluorescently labeled, the plural infected erythrocyte and the plural non-infected erythrocyte are arrayed in parallel in bottom surface portion 13a of well 13 having a diameter of 100 μm. Hole 10a (see FIG. 11A) of biosensor substrate 10 in which the sample is accommodated is set on rotating device 123 (turntable) of fluorescence detection device 1 to start the measurement.

An optical system of fluorescence detection device 1 includes semiconductor laser 101, Polarization Beam Splitter (PBS) 102, collimator lens 103, quarter-wave plate 104, dichroic prism 105, objective lens 106, anamorphic lens 107, photodetector 108, collective lens 109, fluorescence detector 110, and aperture 111. In addition to the optical system, fluorescence detection device 1 also includes holder 121, objective lens actuator 122, rotating device 123, signal calculating circuit 201, servo circuit 202, reproducing circuit 203, signal amplifying circuit 204, controller 205, and clock generating circuit 206.

Semiconductor laser 101 emits a laser beam (hereinafter referred to as "excitation light") having a wavelength of about 405 nm. The excitation light of the second exemplary embodiment is an example of the irradiation light of claims of the present invention. In the excitation light emitted from semiconductor laser 101, the excitation light introduced to biosensor substrate 10, namely, the excitation light passing through aperture 111 is indicated by a broken line in FIG. 17. A circular opening having a predetermined diameter is formed in aperture 111, and the diameter of the excitation light is restricted by aperture 111. The position of semiconductor laser 101 is adjusted such that the excitation light emitted from semiconductor laser 101 becomes S-polarized light with respect to PBS 102. Therefore, after the diameter of the excitation light emitted from semiconductor laser 101 is restricted by aperture 111, the excitation light is reflected by PBS 102, and is incident on collimator lens 103.

Collimator lens 103 converts the excitation light incident from the side of PBS 102 into parallel light. Therefore, the excitation light passing through collimator lens 103 becomes the parallel light having a predetermined diameter. Quarter-wave plate 104 converts the excitation light incident from the side of collimator lens 103 into circularly-polarized light, and converts the excitation light incident from the side of dichroic prism 105 into linearly-polarized light that is orthogonal to a polarization direction of the excitation light incident from the side of collimator lens 103. Therefore, the excitation light incident from the side of collimator lens 103 on PBS 102 is transmitted through PBS 102.

Dichroic prism 105 reflects the laser beam having a wavelength of about 405 nm, and transmits the laser beams having a wavelength of about 450 nm to about 540 nm. Therefore, the excitation light incident from the side of quarter-wave plate 104 is reflected by dichroic prism 105, and is incident on objective lens 106.

Objective lens 106 causes the excitation light to converge properly with respect to biosensor substrate 10. Specifically, objective lens 106 has a predetermined NA (Numerical Aperture, in this case, 0.34) such that the excitation light incident from the side of dichroic prism 105 converges. An incident diameter of the excitation light to objective lens 106 is decided by the diameter of aperture 111. The focal depth of the excitation light caused to converge by objective lens 106 depends on the NA of the excitation light. The focal depth of the excitation light is described later with reference to FIGS. 19A and 19B.

While held by holder 121, objective lens 106 is driven in a focus direction (a direction perpendicular to biosensor substrate 10) and a tracking direction (a radial direction of biosensor substrate 10) by objective lens actuator 122. That is, objective lens 106 is driven such that the excitation light follows the track including the pit strings while focusing on reflecting surface 11a of biosensor substrate 10. The excitation light focusing on reflecting surface 11a is partially reflected by reflecting surface 11a, and largely transmitted through reflecting surface 11a.

The excitation light (hereinafter referred to as "reflected excitation light") reflected by reflecting surface 11a is reflected by dichroic prism 105, converted into the linearly-polarized light by quarter-wave plate 104, and converted into the convergent light by collimator lens 103. The reflected excitation light incident from the side of collimator lens 103 on PBS 102 is transmitted through PBS 102 as described above.

Anamorphic lens 107 introduces astigmatism to the reflected excitation light incident from the side of PBS 102. The reflected excitation light transmitted through anamorphic lens 107 is incident on photodetector 108. Photodetector 108 includes a quadrant sensor that receives the reflected excitation light on a light receiving surface. A detection signal of photodetector 108 is input to signal calculating circuit 201.

In the excitation light with which biosensor substrate 10 is irradiated, the excitation light transmitted through reflecting surface 11a reaches bottom surface portion 13a of well 13. The malaria parasite yields fluorescence when the fluorescent-labeled erythrocytes, which are arrayed in parallel in bottom surface portion 13a while infected with the malaria parasites, are irradiated with the excitation light. The NA (Numerical Aperture) of the fluorescence is larger than the NA of the excitation light as indicated by an alternate long and short dash line in FIG. 17. For this reason, between objective lens 106 and dichroic prism 105, the beam diameter of the fluorescence is larger than the beam diameter of the excitation light. For example, the NA of the fluorescence is 0.65. The wavelength of the fluorescence differs from the wavelength of the excitation light. In the second exemplary embodiment, the fluorescence has a wavelength of 450 nm to 540 nm. On the other hand, the erythrocyte that is not infected with the malaria parasite does not yield the fluorescence because the erythrocyte is not fluorescently labeled. Thus, the erythrocyte infected with the malaria parasite and the erythrocyte not infected with the malaria parasite can be distinguished from each other.

The fluorescence incident from the side of objective lens 106 on dichroic prism 105 is transmitted through dichroic prism 105. Collective lens 109 collects the fluorescence incident from the side of dichroic prism 105, and introduces the fluorescence to fluorescence detector 110. Fluorescence detector 110 includes a sensor that receives the fluorescence on the light receiving surface. A detection signal of fluorescence detector 110 is input to signal amplifying circuit 204.

Signal calculating circuit 201 generates focus error signal FE and tracking error signal TE from the detection signal of photodetector 108, and generates a reproduced RF signal (to be described) from the detection signal of photodetector 108. Servo circuit 202 controls drive of objective lens actuator 122 using focus error signal FE and tracking error signal TE that are output from signal calculating circuit 201. Using the clock signal input from clock generating circuit 206, servo circuit 202 controls rotating device 123 such that biosensor substrate 10 is rotated at a constant linear velocity. Rotating device 123 outputs a rotation detection signal to controller 205 in each rotation. Reproducing circuit 203 generates reproduced data by demodulating the reproduced RF signal output from signal calculating circuit 201. Signal amplifying circuit 204 amplifies the detection signal of fluorescence detector 110.

Controller 205 controls each unit of fluorescence detection device 1 in addition to signal calculating circuit 201, servo circuit 202, and reproducing circuit 203. Controller 205 includes a CPU and a memory, and controls each unit according to a program stored in the memory. Controller 205 also acts as scanning position detector 205a and fluorescent position identifying unit 205b according to a program stored in the memory.

Scanning position detector 205a detects the scanning position of the excitation light in each track portion included in the common address area based on the signal (reproduced RF signal) input from signal calculating circuit 201 and the signal (clock signal) input from clock generating circuit 206. Based on the reproduced data (address information: well address) input from reproducing circuit 203 and the signal (fluorescence detection signal) input from signal amplifying circuit 204, fluorescent position identifying unit 205b determines the position of well 13 in which the fluorescence is detected in biosensor substrate 10, and stores the address information (well address) corresponding to well 13 in which the fluorescence is detected in the internal memory. Based on the reproduced data (address information: track number) input from reproducing circuit 203, the signal (fluorescence detection signal) input from signal amplifying circuit 204, and the scanning position detected by scanning position detector 205a, fluorescent position identifying unit 205b identifies the position where the fluorescence is yielded in the well and the track number, and stores the position and the track number in the internal memory.

The functions of scanning position detector 205a and fluorescent position identifying unit 205b are described later with reference to FIGS. 20A and 20B.

Figure 18:
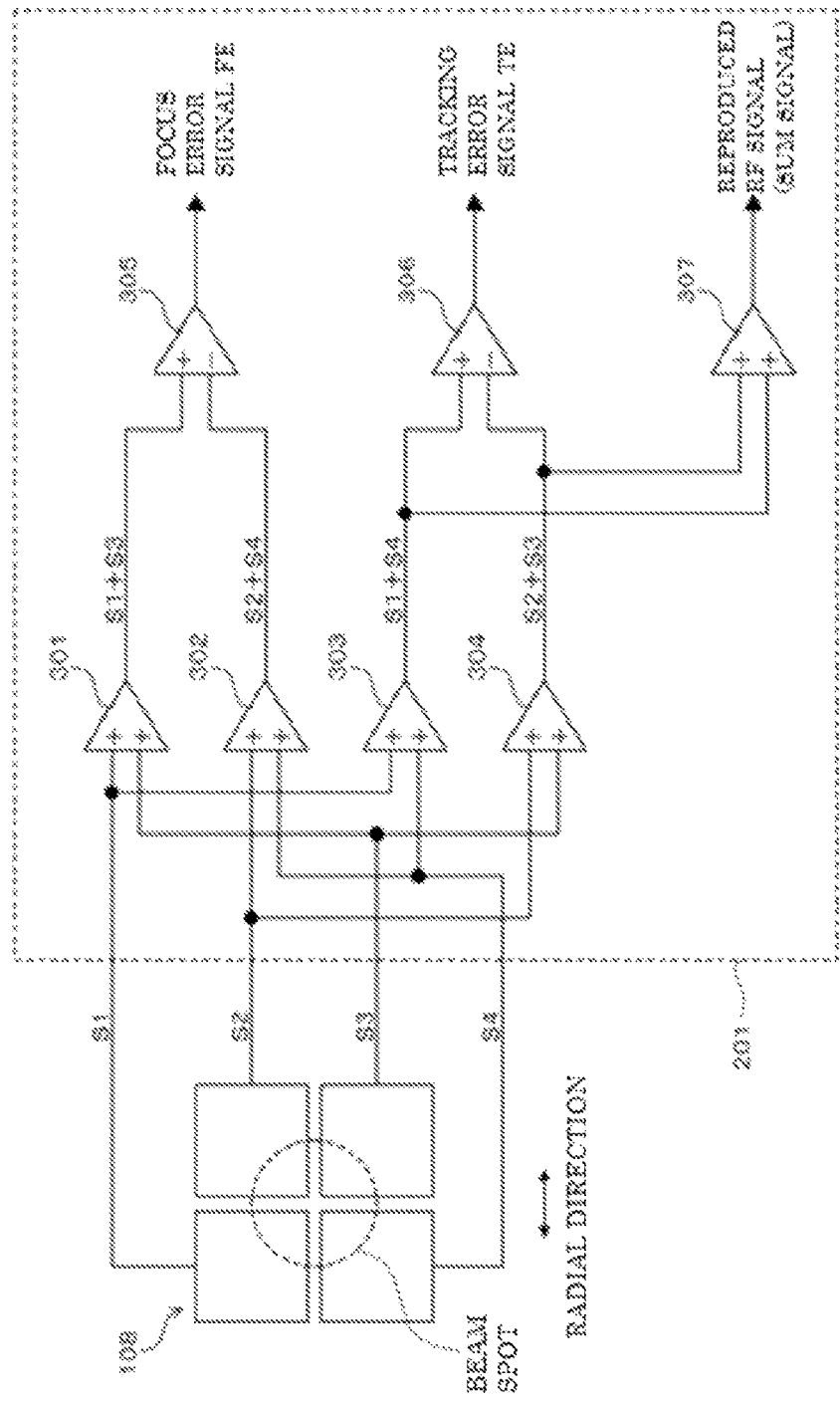
FIG. 18 is a view illustrating a circuit configuration of a signal calculating circuit of the second exemplary embodiment.

FIG. 18 is a view illustrating a circuit configuration of signal calculating circuit 201.

As described above, photodetector 108 includes the quadrant sensor that receives the reflected excitation light on the light receiving surface. Upper left, upper right, lower right, and lower left sensors of the quadrant sensor output detection signals S1 to S4 based on a beam spot of the received reflected excitation light. On the light receiving surface of photodetector 108 in FIG. 17, the right and left direction corresponds to the radial direction of the disk. Focus error signal FE and tracking error signal TE are produced according to the astigmatism method and the one-beam push-pull method that are used in the existing optical disk devices.

Signal calculating circuit 201 includes adders 301 to 304 and 307 and subtractors 305 and 306. Adder 301 outputs a signal to which detection signals S1 and S3 are added to subtractor 305, and adder 302 outputs a signal to which detection signals S2 and S4 are added to subtractor 305. Adder 303 outputs a signal to which detection signals S1 and S4 are added to subtractor 306 and adder 307, and adder 304 outputs a signal to which detection signals S2 and S3 are added to subtractor 306 and adder 307.

Subtractor 305 subtracts the output signals of adders 301 and 302, and outputs focus error signal FE. Subtractor 306 subtracts the output signals of adders 303 and 304, and outputs tracking error signal TE. Adder 307 adds the output signals of adders 303 and 304, and outputs the reproduced RF signal (SUM signal). That is, focus error signal FE, tracking error signal TE, and the reproduced RF signal can be obtained by calculations of the following equations (1) to (3), respectively.

$$FE=(S1+S3)-(S2+S4) \quad (1)$$

$$TE=(S1+S4)-(S2+S3) \quad (2)$$

$$RF=(S1+S2+S3+S4) \quad (3)$$

At this point, when a focal position of objective lens 106 is located on reflecting surface 11a, the beam spot on the quadrant sensor of photodetector 108 becomes a least circle of confusion, and focus error signal FE of the equation (1) becomes a value of 0. When the focal position of objective lens 106 is located immediately above the track (pit) of reflecting surface 11a, the beam spot on the quadrant sensor of photodetector 108 equally overlaps the two left sensors and the two right sensors, and tracking error signal TE of the equation (2) becomes a value of 0.

FIGS. 19A and 19B are views illustrating the focal depth of the excitation light.

As described above, the excitation light has a wavelength of 405 nm, and the excitation light has a NA (Numerical Aperture) of 0.34. Generally, the focal depth can be calculated from the wavelength/(NA×NA). Therefore, in the second exemplary embodiment, the focal depth of the excitation light becomes about 3.5 µm. Distance d3 between bottom surface portion 13a and reflecting surface 11a is set so as to be smaller than the focal depth of the excitation light. In this case, distance d3 is set to 2.0 µm.

As described above, when the NA of the excitation light is set, the spot diameter becomes about 1 µm at the focal position. Distance d6 of the track pitch in FIG. 11C is set to 1 µm so as to be substantially equal to the spot diameter.

FIG. 19A illustrates the state in which the lowest point in the range of the focal depth of the excitation light agrees with reflecting film 14, and FIG. 19B illustrates the state in which the highest point in the range of the focal depth of the excitation light agrees with bottom surface portion 13a. By adjusting the offset voltage output from servo circuit 202 to objective lens actuator 122, the focal depth of the excitation light can be shifted in a deeper direction (upward direction) compared with the focal depth in FIG. 19A.

In the states of FIGS. 19A and 19B, distance d3 between bottom surface portion 13a of well 13 and reflecting surface 11a is 2 µm, and the focal depth of the excitation light is 3.5 µm. Therefore, both bottom surface portion 13a and reflecting surface 11a are included in the range corresponding to the focal depth of the excitation light. Accordingly, the focal position of the excitation light is located on reflecting surface 11a by focus servo, the excitation light is also focused on the sample provided in bottom surface portion 13a.

FIGS. 20A and 20B are views illustrating the functions of scanning position detector 205a and fluorescent position identifying unit 205b of controller 205 in FIG. 17.

The function of scanning position detector 205a will be described with reference to FIG. 20A. FIG. 20A is a timing chart illustrating a change of an output signal when one track portion included in the common address area (see FIG. 14) is scanned with the excitation light.

In FIG. 20A, a waveform at the top stage indicates the reproduced RF signal output from signal calculating circuit 201, a waveform at the second top stage indicates the clock signal output from clock generating circuit 206, a waveform at the third top stage indicates a count value of a counter incorporated in controller 205, and a waveform at the lowest stage indicates the fluorescence detection signal output from signal amplifying circuit 204. The starting position of the synchronous signal becomes the circumferential boundary between the common address areas (see FIG. 14), and the track portion included in the common address area starts from the circumferential boundary.

Clock generating circuit 206 generates and outputs the clock signal in which a phase is matched with that of the reproduced RF signal. The clock signal has a frequency at which the track of biosensor substrate 10 is scanned with the excitation light at a predetermined linear velocity (constant linear velocity). In other words, servo circuit 202 controls rotating device 123 such that the frequency of the clock signal becomes a target frequency and such that the phases of the reproduced RF signal and the clock signal are matched with each other.

Scanning position detector 205a resets the counter at the time the synchronous signal of the unique pattern is detected from the reproduced RF signal, and causes the counter to start the counting of a number of pulses of the clock signal. Therefore, the count value of the counter increases as time advances, namely, as the scanning of the track portion with the excitation light advances. Scanning position detector 205a acquires the count value of the counter as the scanning position of the excitation light with respect to the track portion.

The function of fluorescent position identifying unit 205b will be described below. Fluorescent position identifying unit 205b compares the fluorescence detection signal indicated at the lowest stage in FIG. 20A to predetermined threshold SH. Specifically, the value of the fluorescence detection signal is acquired in each pulse of the clock signal, and the acquired value of the fluorescence detection signal is compared to threshold SH. When the value of the fluorescence detection signal exceeds threshold SH, fluorescent position identifying unit 205b acquires the count value of the counter as the scanning position of the track portion in which the fluorescence is yielded.

In the case of FIG. 20A, the value of the fluorescence detection signal exceeds threshold SH in time period Δt. Time period Δt includes the three pulses of the clock signal, and the value of the counter changes to Cka, Ckb, and Ckc in time period Δt. Fluorescent position identifying unit 205b stores three counter values Cka, Ckb, and Ckc in the internal memory of controller 205 while associating counter values Cka, Ckb, and Ckc with values La, Lb, and Lc of the fluorescence detection signals acquired at the clock times corresponding to the counter values Cka, Ckb, and Ckc. At the same time, fluorescent position identifying unit 205b stores well address Wa and track number Ta, which is acquired by reproducing circuit 203 by scanning the address area of the track portion, in the internal memory of controller 205 while associating well address Wa and track number Ta with counter values Cka, Ckb, and Ckc and fluorescence detection signal values La, Lb, and Lc. Therefore, fluorescence identifying information is formed in order to identify the position where the fluorescence is yielded.

FIG. 20B is a view illustrating a data structure of the fluorescence identifying information stored in the internal memory of controller 205 by fluorescent position identifying unit 205b.

As illustrated in FIG. 20B, the fluorescence identifying information has a configuration in which the fluorescence detection signal value exceeding threshold SH is associated with the scanning position (counter value) of the excitation light at that time. Additionally, the well address of well 13 scanned with the excitation light at the time the fluorescence is yielded and the track number of the scanned track portion are associated with the fluorescence detection signal value. In the example of FIG. 20B, scanning positions (counter values)

Cka, Ckb, and Ckc are associated with fluorescence detection signal values La, Lb, and Lc, and the track numbers and the well addresses, which identify the track portions and wells 13 scanned at that time, are also associated with fluorescence detection signal values La, Lb, and Lc. The position where the fluorescence is yielded on biosensor substrate 10 and an intensity of the fluorescence can be recognized by referring to the fluorescence identifying information having the above configuration.

Desirably the fluorescence identifying information further includes identification information identifying biosensor substrate 10. For example, the identification information on biosensor substrate 10 may be stored in a predetermined reserve area. Alternatively, a management area where well 13 does not exist may be provided in biosensor substrate 10, and the identification information on biosensor substrate 10 may be held by the track (pit string) of the management area.

Figure 21A:
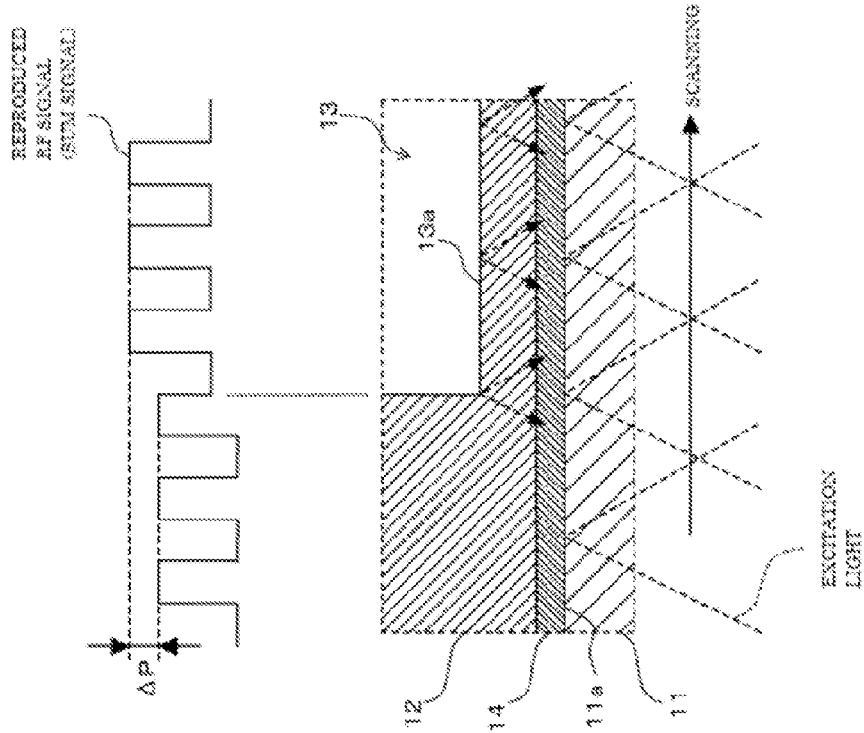
FIG. 21A is a flowchart illustrating excitation light scanning control processing of the second exemplary embodiment.
Figure 21B:
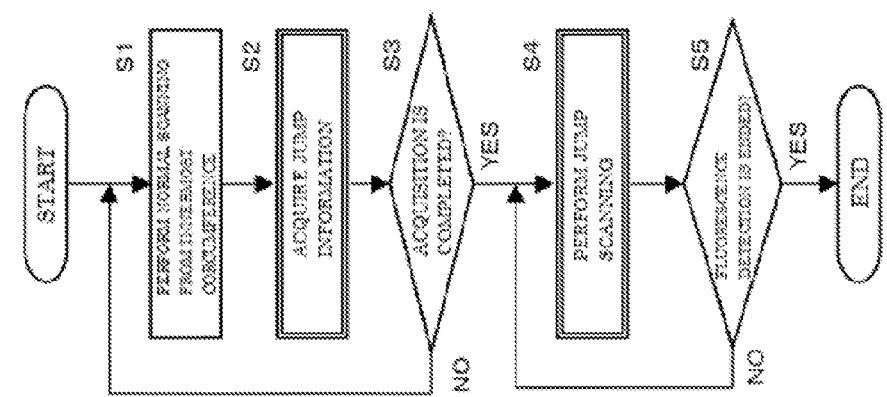
FIG. 21B is a view illustrating a non-well area detecting method.

FIG. 21A is a flowchart illustrating excitation light scanning control performed by controller 205 during a fluorescence detection operation. FIG. 21B illustrates a method for detecting the well.

The method for detecting well 13 will be described with reference to FIG. 21B. When reflecting surface 11*a* is scanned with the excitation light as illustrated at the lower stage in FIG. 21B, part of the excitation light is reflected by reflecting surface 11*a*, and remaining excitation light is transmitted through reflecting surface 11*a*. When the portion in which well 13 does not exist is scanned with the excitation light, the excitation light transmitted through reflecting surface 11*a* enters well layer 12, and reaches the upper surface of well layer 12. The excitation light is partially reflected by the upper surface of well layer 12, and is incident on objective lens 106 through reflecting film 14 and base substrate 11. Then the excitation light is incident on photodetector 108 by adversely traveling the optical path in FIG. 17. Therefore, a signal component of the excitation light (hereinafter referred to as "first reflective stray light") is superimposed on the output signal of photodetector 108.

On the other hand, when the portion in which well 13 exists is scanned with the excitation light, the excitation light transmitted through reflecting surface 11*a* enters well layer 12, and reaches bottom surface portion 13*a* of well 13. The excitation light is partially reflected by bottom surface portion 13*a* of well 13, and is incident on objective lens 106 through reflecting film 14 and base substrate 11. Then, similar to the first reflective stray light, the excitation light is incident on photodetector 108 by adversely traveling the optical path in FIG. 17. Therefore, a signal component of the excitation light (hereinafter referred to as "second reflective stray light") is superimposed on the output signal of photodetector 108.

Thus, the first reflective stray light is incident on photodetector 108 when the portion in which well 13 does not exist is scanned with the excitation light, and the second reflective stray light is incident on photodetector 108 when the portion in which well 13 exists is scanned with the excitation light. However, the first reflective stray light differs largely from the second reflective stray light in optical environment, such as the optical path until the corresponding excitation light exits to the outside from the lower surface of base substrate 11 after being transmitted through reflecting surface 11*a* from the side of base substrate 11, the surface from which the excitation light is reflected, a medium (refractive index) located at the back of the reflecting surface, and the convergent state of the excitation light on the reflecting surface. Therefore, the first reflective stray light differs largely from the second reflective stray light in the intensity of the light incident on photodetector 108. The signal component of the first reflective stray light superimposed on the output signal of photodetector 108 also differs from the signal component of the second reflective stray light superimposed on the output signal of photodetector 108. As a result, a difference is generated in a level of the signal output from photodetector 108 according to whether the portion in which well 13 exists or the portion in which well 13 does not exist is scanned with the excitation light. Accordingly, for example, whether well 13 exists at the scanning position of the excitation light can be determined by detecting the difference using the reproduced RF signal (SUM signal).

For example, when the amount of second reflective stray light is larger than the amount of first reflective stray light, the case that the portion in which well 13 exists is scanned with the excitation light is higher than the case that the portion in which well 13 does not exist is scanned with the excitation light in the level of the reproduced RF signal as illustrated at the upper stage in FIG. 21B. Therefore, a determination that the scanning position of the excitation light passes through the boundary between the portion in which well 13 exists and the portion in which well 13 does not exist is made when a difference ΔP between peak values of the waveforms of the reproduced RF signals exceeds a predetermined threshold.

The excitation light scanning control performed by controller 205 during the fluorescence detection operation will be described below with reference to FIG. 21A. In the excitation light scanning control, the radial non-well area is jumped to shorten a scanning time in scanning the track during the fluorescence detection operation.

At this point, it is assumed that the management information on biosensor substrate 10 is held in the reserve area of a predetermined track provided in biosensor substrate 10, and that information on a number of wells arranged in biosensor substrate 10 and information on the well address of the common address area where the tail-end well 13 is set are acquired by reproducing the management information on biosensor substrate 10. For example, the management information is held in the innermost circumferential track. At a beginning of the fluorescence detection operation, fluorescence detection device 1 reads the management information, and stores the management information in the internal memory of controller 205.

In the scanning control during the fluorescence detection operation, controller 205 starts the scanning with the excitation light from the innermost circumferential track of biosensor substrate 10 (S1). Controller 205 acquires jump information for a track jump while the innermost circumferential zone is scanned with the excitation light (S2). The specific processing in Step S2 is described later with reference to FIGS. 22A, 23A, and 24A. When the jump information is obtained (YES in S3), controller 205 performs jump scanning control (S4). In the jump scanning control, the track is scanned while the radially-generated non-well area (see FIG. 14) is skipped. The specific processing in Step S4 is described later with reference to FIGS. 22B, 23B, and 24B. Controller 205 performs the jump scanning control until the fluorescence detection operation is ended. When the fluorescence detection operation is ended by completion of the scanning of the tail-end well 13 (YES in S5), controller 205 ends the scanning control.

As described above with reference to FIGS. 16A and 16B, well 13 is formed by pressing well stamper WS against base substrate 11. Therefore, the positions of wells 13 are uniformly located in the center of the common address area, or uniformly deviated to one direction from the center of the common address area.

In the case that wells 13 are properly arranged, wells 13 are arranged in the centers of the right and left common address areas. In the second exemplary embodiment, the radial width of the common address area is set to about 300 µm and the diameter of well 13 is set to about 100 µm. Therefore, in the case that well 13 is arranged in the center of the common address area, the width of the non-well area becomes about 200 µm and the non-well area includes about 200 tracks.

On the other hand, when well 13 is arranged while deviated to the left from the center of the common address area, well 13 is deviated in the outer circumferential direction in the left common address area with respect to the center of the disk, and well 13 is deviated in the inner circumferential direction in the right common address area. In this case, the non-well area covers the range between an end (assumed as diameter Da) on the outer circumferential side of well 13 provided in the left common address area and an end (assumed as diameter Db) on the inner circumferential side of well 13 provided in the right common address area. That is, well 13 is not detected while the tracks between diameter Da and diameter Db are scanned with the excitation light. Accordingly, non-well area is narrowed compared with the case that well 13 is properly arranged.

At this point, the position of well 13 is deviated to the left from the center of the common address area. In the case that the position of well 13 is deviated to other directions from the center of the common address area, similarly the width of the non-well area is narrowed compared with the case that well 13 is properly arranged. The width of the non-well area changes according to a deviation amount of well 13 with respect to the central position of the common address area.

In the processing of FIG. 21A, in order to avoid the scanning of the non-well area where the well does not exist, it is necessary to detect the width (the number of tracks) of the non-well area or the positions (track numbers) of diameters Da and Db. In S2 (jump information acquisition processing) of FIG. 21A, the width of the non-well area or the positions of boundaries Da and Db are acquired while the innermost circumferential zone is scanned with the excitation light.

Figure 22B:
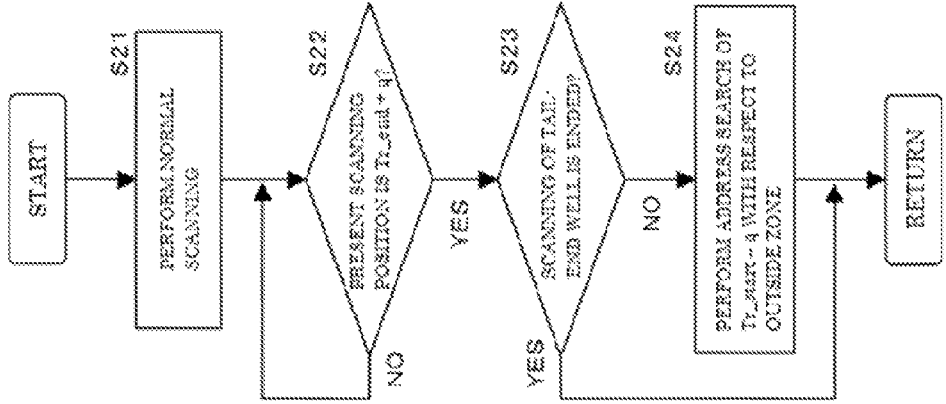
FIGS. 22A and 22B are flowcharts illustrating jump information acquisition processing and jump scanning processing of the second exemplary embodiment.
Figure 22A:
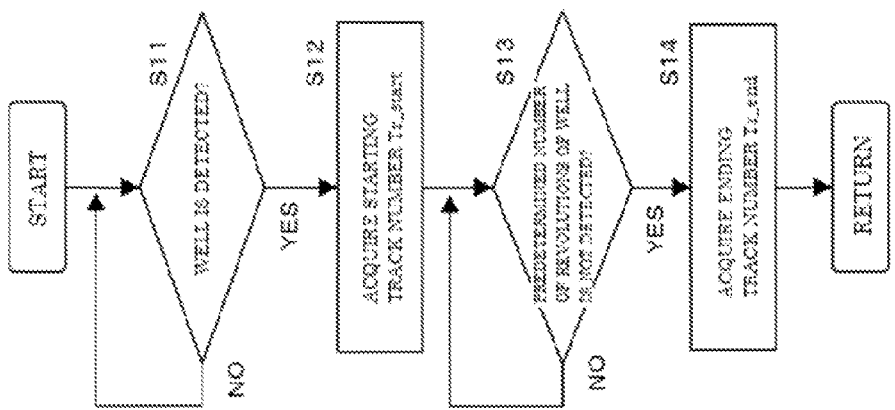

FIG. 22A is a view illustrating a content of the jump information acquisition processing.

When well 13 is detected by the technique in FIG. 21B while the innermost circumferential zone is scanned with the excitation light in Step S1 of FIG. 21A (YES in S11), controller 205 acquires the track number, which is reproduced from the track in the common address area scanned at that time, as starting track number Tr_start of well 13 in the zone (S12). Because the track number added to each common address area is identical while biosensor substrate 10 rotates once from reference diameter D0, no problem is generated even if the track number reproduced from one common address area is acquired as starting track number Tr_start.

Controller 205 determines whether well 13 is not scanned with the excitation light while biosensor substrate 10 rotates a predetermined number of times (S13). As described above, whether well 13 is not scanned with the excitation light is determined by monitoring the output of the reproduced RF signal (SUM signal). Whether biosensor substrate 10 rotates the predetermined number of times is determined by a rotation detection signal output from rotating device 123 to controller 205.

When well 13 is not scanned with the excitation light while biosensor substrate 10 rotates the predetermined number of times (YES in S13), controller 205 acquires the track number, which is reproduced from the track in the common address area scanned at that time, as ending track number Tr_end of well 13 in the zone (S14). Therefore, the jump information acquisition processing is ended.

Because all wells 13 are substantially uniformly deviated with respect to the common address area, starting track number Tr_start acquired in the innermost circumferential zone agrees substantially with the number of track in which well 13 is initially scanned in another zone, and ending track number Tr_end agrees substantially with the number of track slightly outside the track in which well 13 is finally scanned in another zone. Accordingly, starting track number Tr_start and ending track number Tr_end that are acquired in the innermost circumferential zone can also be used as the information for jumping the non-well area in another zone. Starting track number Tr_start and ending track number Tr_end can be acquired in the shortest time by acquiring starting track number Tr_start and ending track number Tr_end in the innermost circumference.

When the acquisition of the jump information (starting track number Tr_start and ending track number Tr_end) is completed, an affirmative determination is made in S3 of FIG. 21A, and the processing is advanced to S4 (jump scanning processing).

FIG. 22B is a view illustrating the jump scanning processing.

After acquiring starting track number Tr_start and ending track number Tr_end, controller 205 continues the scanning of the track (S21). When the scanning position of the excitation light enters the track having the track number that is larger than ending track number Tr_end by q (for example, q=10), controller 205 determines whether the scanning of tail-end well 13 provided in biosensor substrate 10 is ended (S23). For example, the determination in S23 is made based on whether the well address of the common address area where tail-end well 13 is set is reproduced while biosensor substrate 10 rotates once from the present scanning position.

When the scanning of tail-end well 13 is ended (YES in S23), controller 205 ends the jump scanning processing, and advances the processing to Step S5 in FIG. 21A. In this case, because the scanning of tail-end well 13 is ended, the fluorescence detection operation is ended (YES in S5), and the scanning control is ended.

When the scanning of tail-end well 13 is not ended (NO in S23), controller 205 controls servo circuit 202, and performs an address search operation to jump the scanning position of the excitation light to the track position having the track number that is smaller than starting track number Tr_start in the outside zone by q (for example, q=10). Technologies in existing CD players or DVD players can be adopted in the address search operation. When the address search operation is ended, controller 205 ends the jump scanning processing, and advances the processing to Step S5 in FIG. 21A. When a negative determination is made in Step S5, controller 205 advances the processing to Step S4, and performs the jump scanning processing again.

Figure 23B:
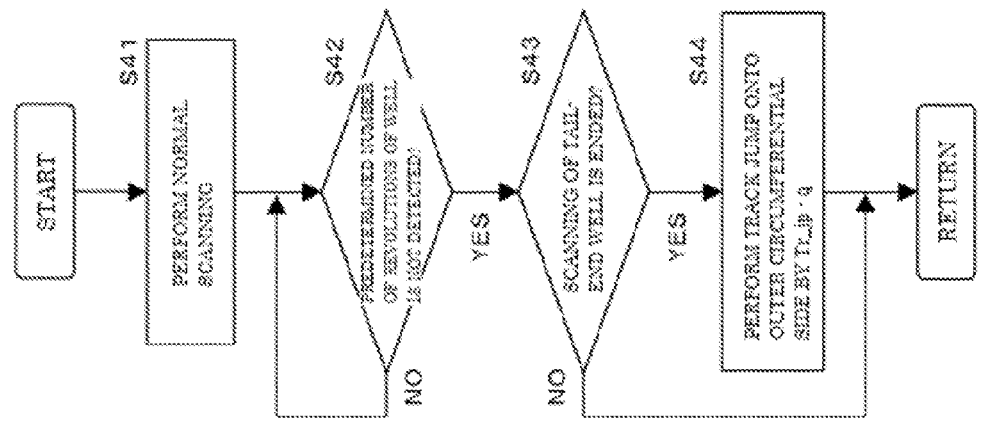
FIGS. 23A and 23B are flowcharts illustrating another piece of jump information acquisition processing and another piece of jump scanning processing of the second exemplary embodiment.
Figure 23A:
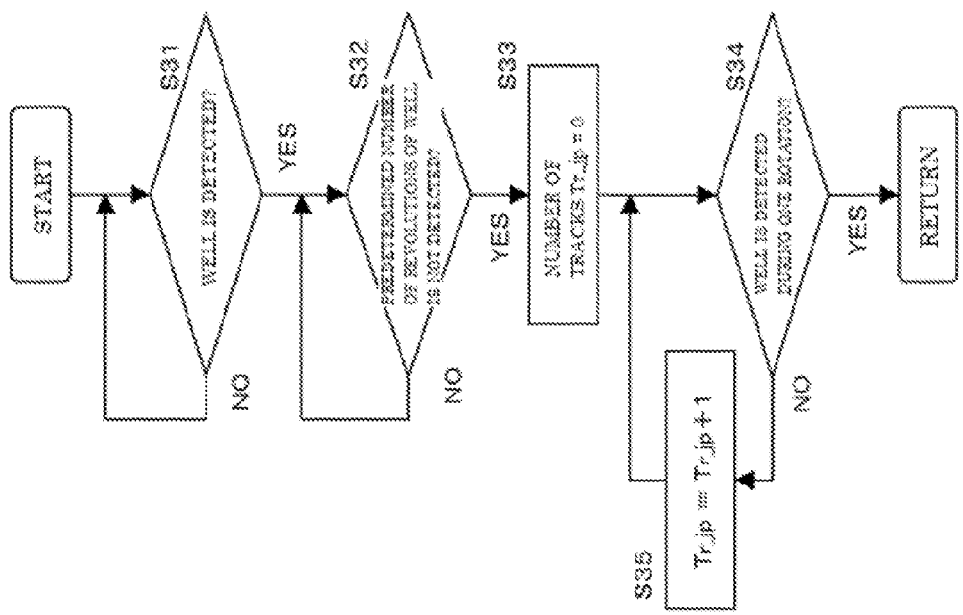

FIG. 23A is a view illustrating another content of the jump information acquisition processing.

When well 13 is detected by the technique in FIG. 21B while the innermost circumferential zone is scanned with the excitation light in Step S1 of FIG. 21A (YES in S31), controller 205 waits for run-off of the scanning position from well 13 (S32). When well 13 is not scanned with the excitation light while biosensor substrate 10 rotates the predetermined number of times since the scanning position runs off from well 13 (YES in S32), controller 205 resets the counter that counts a number of tracks Tr_jp to zero (S33), and starts the counting of the number of tracks included in the radial non-track area. Controller 205 determines whether well 13 is detected while biosensor substrate 10 rotates once (S34). When well 13 is not detected (NO in S34), a counter value is incremented by 1 (S35). The number of tracks Tr_jp is incremented until the time well 13 is detected (YES in S34). Thus, the number of radial tracks Tr_jp included in the non-well area is counted.

Because all wells 13 are substantially uniformly deviated with respect to the common address area as described above, the number of tracks Tr_jp (the radial width of the non-well area) acquired in the non-well area between the innermost circumferential zone and the outside zone is substantially equal to the number of tracks Tr_jp acquired in the non-well area between other zones adjacent to each other. Accordingly, the number of tracks Tr_jp acquired in the above manner can be used as the information for jumping the non-well area in other zones.

When the acquisition of the jump information (the number of tracks Tr_jp) is completed, the affirmative determination is made in S3 of FIG. 21A, and the processing is advanced to S4 (jump scanning processing).

FIG. 23B is a view illustrating another content of the jump scanning processing.

After acquiring the number of tracks Tr_jp as described above, controller 205 continues the scanning of the track (S41). When well 13 is not scanned with the excitation light while biosensor substrate 10 rotates the predetermined number of times (YES in S42), controller 205 determines whether the scanning of tail-end well 13 provided in biosensor substrate 10 is ended (S43). When the scanning of tail-end well 13 is ended (YES in S43), controller 205 ends the jump scanning processing, and advances the processing to Step S5 in FIG. 21A. In this case, the fluorescence detection operation is ended (YES in S5), and the scanning control is ended.

When the scanning of tail-end well 13 is not ended (NO in S43), controller 205 controls servo circuit 202 to jump the scanning position of the excitation light onto the outer circumferential side by the number of tracks that is smaller than the number of tracks Tr_jp by q (for example, q=10) (S44). At this point, servo circuit 202 performs the track jump by the designated number of tracks (Tr_jp−q) while turning off tracking servo. After the predetermined track jump is performed, the tracking servo is turned on, and the excitation light is located on the post-jump track. Therefore, the scanning of the post-jump track with the excitation light is started. Technologies in existing CD players or DVD players can be adopted in the track jump operation.

When the track jump operation is ended, controller 205 ends the jump scanning processing, and advances the processing to Step S5 in FIG. 21A. When a negative determination is made in Step S5, controller 205 advances the processing to Step S4, and performs the jump scanning processing again.

The scanning of the non-well area is skipped through the pieces of processing in FIGS. 22A, 22B, 23A, and 23B in scanning biosensor substrate 10, so that whole biosensor substrate 10 can rapidly and efficiently be scanned. Therefore, the fluorescence detection operation can rapidly and efficiently be performed to biosensor substrate 10.

In Step S24 of FIG. 22, the address search is used to skip the non-well area. Alternatively, the track jump can also be used. In this case, the number of jumps Tr_jp that the track jump should be performed can be obtained by the following equation.

$$Tr\_jp = (N - Tr\_end) + Tr\_start - 2q \quad (4)$$

Where N is a number of track portions included in the common address area. In the second exemplary embodiment, N is 300. For example, similarly q is 10. Through the processing in which the track jump is used, the scanning position of the excitation light can be jumped to a neighborhood of the position of the track number that is smaller than the starting track number Tr_start in the outside zone by q (for example, q=10).

Figure 24:
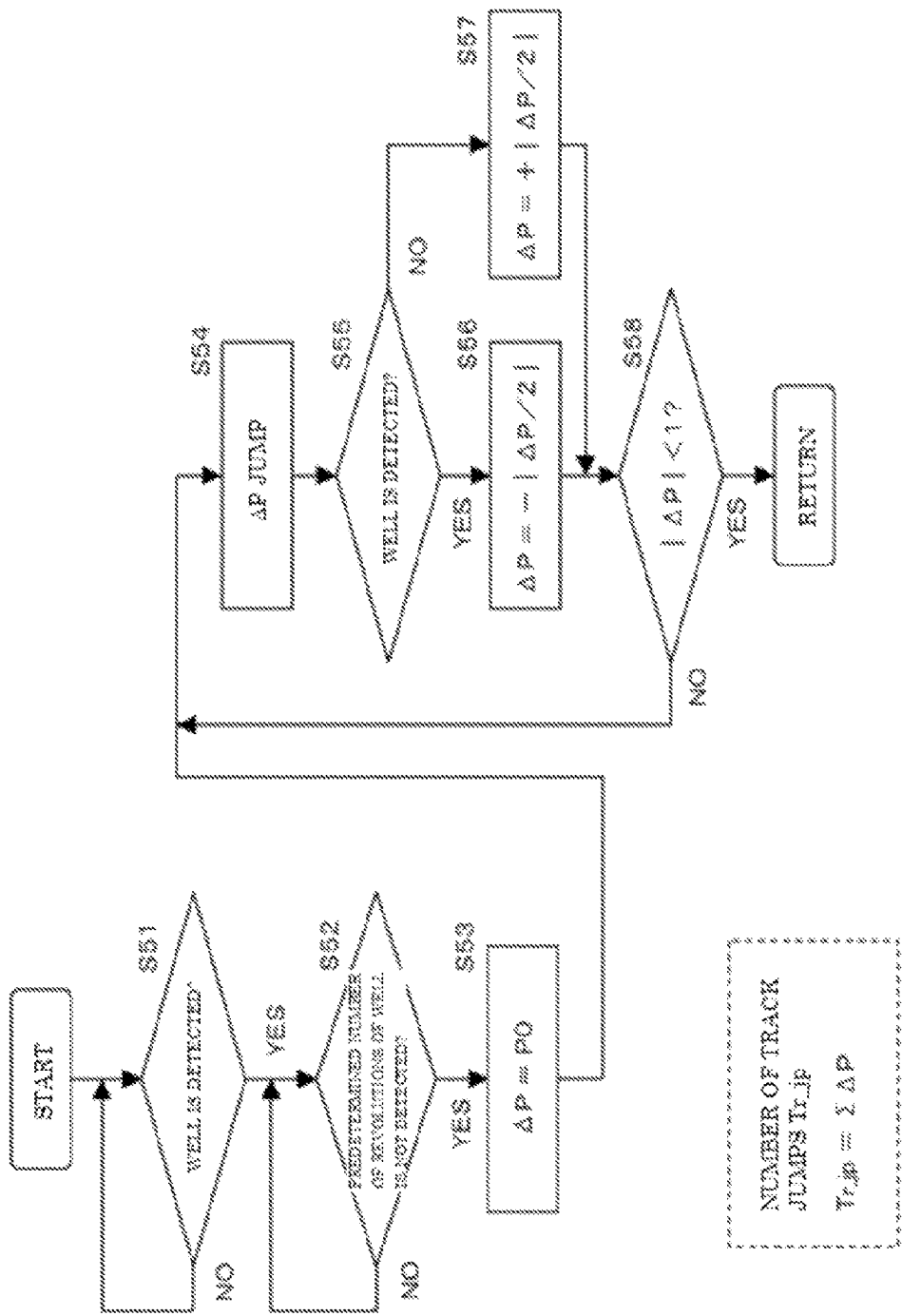
FIG. 24 is a flowchart illustrating still another piece of jump information acquisition processing of the second exemplary embodiment.

The jump information acquisition processing in FIG. 23A can be changed as illustrated in FIG. 24. In FIG. 24, Steps S51 and S52 are identical to Step S31 and S32 in FIG. 23. When well 13 is not scanned with the excitation light while biosensor substrate 10 rotates the predetermined number of times (YES in S32), controller 205 sets P0 (for example, 128) to variable ΔP (S53), and jumps the scanning position of the excitation light onto the outer circumferential side by variable ΔP (S54). Controller 205 determines whether well 13 is detected at the post-jump position (S55). When well 13 is detected (YES in S55), variable ΔP is set to ΔP=−|ΔP/2| (S56). When well 13 is not detected (NO in S55), variable ΔP is set to ΔP=+|ΔP/2|. At this point, a sign of the variable indicates the direction of the track jump, + (positive) indicates the outer circumferential side, and − (negative) indicates the inner circumferential side.

Controller 205 determines whether absolute value |ΔP| is smaller than 1. Controller 205 ends the processing when absolute value |ΔP| is smaller than 1. When absolute value |ΔP| is not smaller than 1, controller 205 returns the processing to Step S54, and performs the similar processing. When the pieces of processing in Steps S54 to S58 are repeated, the scanning position of the excitation light comes close to the track near the boundary on the inner circumferential side of the well area in the outside zone. When absolute value |ΔP| of variable ΔP is determined to be less than 1 (that is, ½) in Step S58, the scanning position of the excitation light is located on the track near the boundary on the inner circumferential side of the well area (see FIG. 14) in the outside zone.

Controller 205 cumulatively adds variable ΔP to update the number of track jumps Tr_jp every time variable ΔP changes until variable ΔP becomes 1 since Step S53 in FIG. 24. In the case that the sign of variable ΔP is − (negative), negative value ΔP is added to the number of track jumps Tr_jp, and the number of track jumps Tr_jp is decreased by |ΔP|. When variable ΔP becomes 1, the number of track jumps Tr_jp is substantially equal to the number of radial tracks included in the non-well area. Therefore, the number of track jumps Tr_jp can be used instead of the number of track jumps Tr_jp acquired through the processing in FIG. 23A.

Because the scanning position of the excitation light can be located on the track near the boundary on the inner circumferential side of the well area in the outside zone through the processing in FIG. 24, the processing in FIG. 24 may be used in not counting of the number of tracks but the operation to skip the non-well area.

Figure 25:
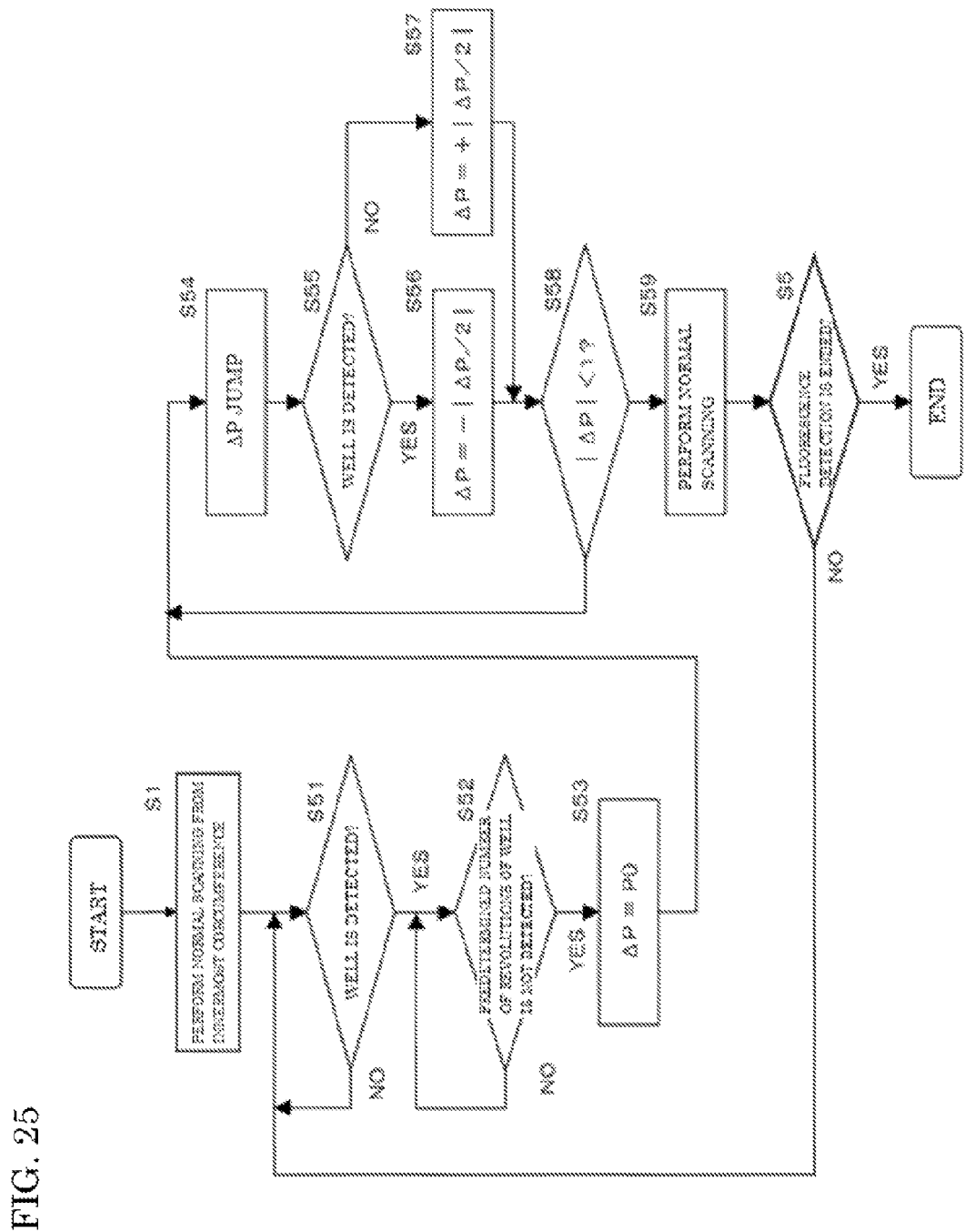
FIG. 25 is a flowchart illustrating another piece of excitation light scanning control processing of the second exemplary embodiment.

FIG. 25 is a view illustrating the processing in this case.

In the flowchart of FIG. 25, Steps S1 and S5 are identical to Steps S1 and S5 in FIG. 21A. Steps S51 to S58 in FIG. 25 are identical to those in FIG. 24.

In the processing of FIG. 25, when well 13 is detected after the scanning with the excitation light is started from the innermost circumference of biosensor substrate 10 (S1), controller 205 determines whether the scanning position of the excitation light runs off from the well area (S52). When the scanning position of the excitation light runs off from the well area (YES in S52), controller 205 performs the pieces of processing in Steps S53 to S58, and jumps the scanning position of the excitation light to the track near the boundary on the inner circumferential side of the well area in the outside zone. When the jump is ended (YES in S58), controller 205 determines resumes the normal scanning (S59), and determines whether the fluorescence detection operation is ended (S5). When the fluorescence detection operation is not ended (NO in S5), controller 205 returns the processing to Step S51, and repeats the similar processing. Thus, biosensor substrate 10 is scanned with the excitation light from the innermost circumference to the outermost circumference while the non-well area between the zones adjacent to each other is skipped.

As described above, according to the second exemplary embodiment, the identical well address identifying the position of well 13 is provided to the track portion traversing identical well 13, so that well 13 can be associated with the position of well 13 identified by the well address information on a one-on-one basis. Therefore, in fluorescence detection device 1, the position of well 13 can easily and smoothly be identified by the well address, and a processing load can be reduced.

According to the second exemplary embodiment, the identical well address is provided to the common address area wider than well 13, so that well 13 can be located in the common address area even if the position of well 13 is deviated in arranging well 13 in biosensor substrate 10. Therefore, the identical well address can more surely be provided to one well 13.

According to the second exemplary embodiment, the track number is acquired on the side of fluorescence detection device 1, so that the radial position on well 13 can be recognized by the track number. Therefore, in fluorescence detection device 1, the position where the fluorescence is yielded can more finely be recognized.

According to the second exemplary embodiment, because the scanning position of the excitation light on the track portion included in one common address area is detected by scanning position detector 205a, the scanning position of the excitation light can be identified when the fluorescence is detected, and the position where the fluorescence is detected in the common address area can more finely be recognized in fluorescence detection device 1.

According to the second exemplary embodiment, the position where the fluorescence is yielded is identified by the position of well 13 using the fluorescence identifying information in FIG. 20B, and the position where the fluorescence is yielded is also identified by the track in well 13 and the scanning position on the track. Therefore, in fluorescence detection device 1, the position where the fluorescence is yielded can more finely be recognized.

According to the second exemplary embodiment, the non-well area where well 13 is not arranged is skipped by the control in FIG. 21A, so that biosensor substrate 10 can rapidly and smoothly be scanned with the excitation light.

Although the exemplary embodiments of the present invention are described above, the present invention is not limited to the exemplary embodiments, but various changes can be made in addition to the exemplary embodiments of the present invention.

For example, in the first and second exemplary embodiments, the erythrocyte is accommodated in well 13 to determine whether the erythrocyte is infected with the malaria parasite. However, there is no limitation to the sample accommodated in well 13 and the event of the determination target.

For example, a cell expressing a specific gene or a cell in which there is an excess or lack of biological materials such as a nucleic acid, a protein, a lipid, and a sugar may be detected from various cell groups as a specific cell. Alternatively, a normally functioning cell may adversely be detected from the cell group as the specific cell. For example, this is used to detect the normally-differentiated cell when an iPS cell or an ES cell is induced from an undifferentiated state to a differentiated state. The specific cell may be a cell existing in nature or a cell to which a human-induced treatment is performed.

There is no particular limitation to the cell existing in nature. Examples of the cell existing in nature include a pathogenic cell, a pathological change cell, a cell infected with a pathogen or a pathogenic organism, a mutated cell, and an unknown cell having a specific property. There is no particular limitation to the human-induced treatment. Examples of the human-induced treatment include a physical treatment (for example, electromagnetic wave irradiation), a chemical treatment (for example, medical agent treatment), and a genetic engineering treatment (for example, genetic recombination treatment).

The human-induced treatment in which an influence on the cell is well known is performed to the cell group, and the cell in which the influence does not appear or the cell in which the influence appears strongly can be detected as the specific cell. For example, the cell having a tolerance to the medical agent treatment or the cell exerting high sensitivity to the medical agent treatment can be detected as the specific cell.

There is no particular limitation to a kind of the cell group. The cell group may be a cell group derived from a multicellular organism in addition to a single-celled organism. Examples of the multicellular organism include cells obtained from a normal tissue and a pathological tissue of the organism and a cultured cell derived from the cells. There is no particular limitation to the organism from which the cells are obtained. For example, a cell harvested from an animal or a plant may be used. More specifically, a cell harvested from a vertebrate animal (particularly, a mammal and an ayes), a cell harvested from an insect, and a plant cultured cell can be cited as an example of the cell of the detection target. However, the cell of the detection target is not limited to the cited cells. The group of identical cells or the group of different kinds of cells may be used.

In the first and second exemplary embodiments, reflecting film 14 is made of metal. Alternatively, reflecting film 14 may be made of a dielectric material having translucency. In this case, base substrate 11 differs from the dielectric material in the refractive index, which allows the reflection to be generated. Specifically, for example, polycarbonate (refractive index of 1.59) can be used as the material for base substrate 11, and $TiO_2$ (refractive index of 2.65) can be used as the material for reflecting film 14. When niobium dioxide ($Nb_2O_5$) is used as the material for reflecting film 14, the reflectance is enhanced near a wavelength of 400 nm while the reflectance is decreased near a wavelength of 500 nm, the reflectance is enhanced to the excitation light, and the reflection is constrained to the fluorescence. A stacked film of a dielectric film and a metallic film may be used as reflecting film 14.

In the first and second exemplary embodiments, well 13 has the columnar shape as illustrated in FIGS. 1A and 11A. However, well 13 may have any shape as long as the sample can be accommodated. Diameter d1 and height d2 of well 13, distance d3 between bottom surface portion 13a and reflecting surface 11a, interval d4 between wells 13, thickness d5 of base substrate 11, and track pitch d6 of reflecting surface 11a are not limited to the above values, but may be set to proper values. The address length of reflecting surface 11a may be set by various methods as long as the position of well 13 can be identified.

In the first and second exemplary embodiments, the wavelength of the excitation light emitted from semiconductor laser 101 is set to 405 nm. Alternatively, the wavelength may properly be set according to the kind of the fluorescent label used in the sample of the measurement target. Various parameters such as a transmission wavelength band of dichroic prism 105 are properly changed in the optical system according to the change in wavelength of the excitation light. In the first and second exemplary embodiments, the NA of the excitation light is set to 0.34. Alternatively, the NA may properly be set according to the size of the sample of the measurement target. For example, when the NA of the excitation light is set to 0.1 while the wavelength of the excitation light is set to 635 nm, the focal depth of the excitation light becomes 63.5 µm. When the focal depth of the excitation light is larger than the focal depth (about 3.5 µm) of the excitation light of the embodiments, distance d3 between bottom surface portion 13a of well 13 and reflecting surface 11a can be set larger than distance (2 µm) of the first and second exemplary embodiments.

In the first and second exemplary embodiments, as illustrated in FIGS. 2A to 2D and 15A to 15D, base substrate 11 is formed by injection molding, reflecting film 14 is evaporated on the upper surface of reflecting surface 11a, bottom layer 12a is stacked by spin coating, and top layer 12b is formed by photo-polymer molding, whereby producing biosensor substrate 10. However, the method for producing biosensor substrate 10 is not limited to the method of the first and second exemplary embodiments, but biosensor substrate 10 may properly be produced by another method.

In the first modification, as illustrated in FIG. 6, well 13 is not formed in well layer 12 corresponding to the lead-in area. Alternatively, well 13 may be formed in well layer 12 corresponding to the lead-in area. However, as described above, desirably well 13 is not formed in well layer 12 corresponding to the lead-in area, when the sample is dropped inside biosensor substrate 20 to flow into well 13 while biosensor substrate 20 is slowly rotated.

In the first and second exemplary embodiments, a cover may be provided on the top of well 13 when biosensor substrates 10 and 20 are rotated by rotating device 123. Therefore, undesirable outflow (unintended outflow), vaporization, or movement of the sample from well 13 can be prevented.

Figure 26A:
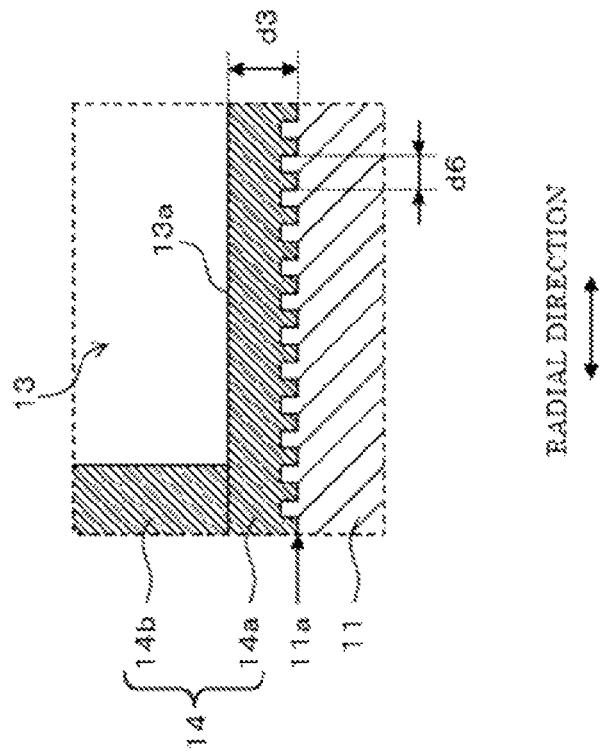
FIGS. 26A and 26B are views illustrating other configuration examples of the well of the first exemplary embodiment.
Figure 26B:
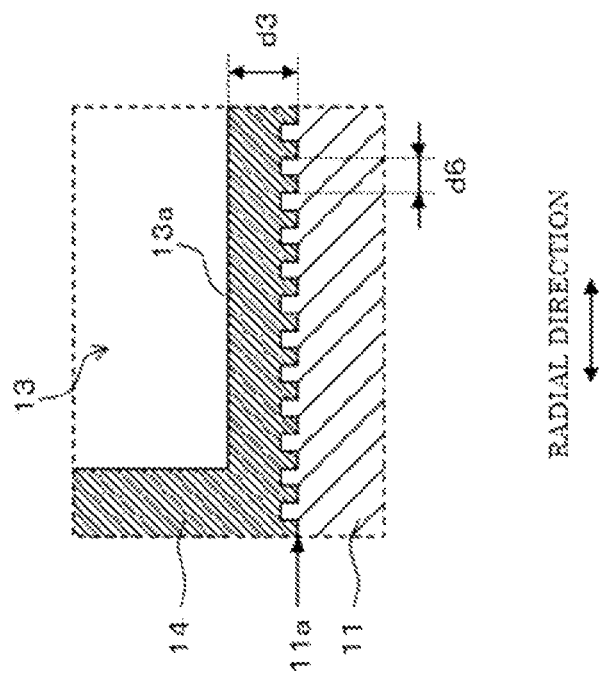

In the first exemplary embodiment 1, well layer 12 is arranged on reflecting film 14. Alternatively, reflecting film 14 may be used as well layer 12. As illustrated in FIG. 26A, plural micro wells 13 may be formed in reflecting film 14 formed on the upper surface of base substrate 11. In this case, a material having a refractive index different from that of base substrate 11 may be used as reflecting film 14, and a resin material having a different refractive index can be used as reflecting film 14. Reflecting film 14 in FIG. 26A may be constructed with bottom layer 14a and top layer 14b as illustrated in FIG. 26B. In this case, bottom layer 14a may differ from top layer 14b in a material.

In the first exemplary embodiment, biosensor substrates 10 and 20 have the disc shape. Alternatively, biosensor substrates 10 and 20 may have a square outline.

Figure 27A:
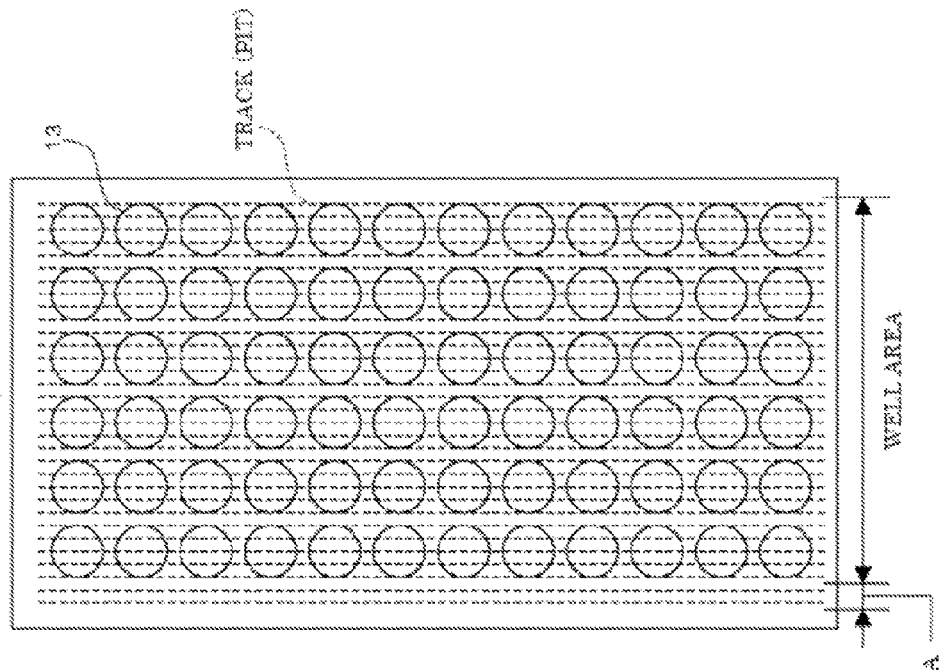
FIGS. 27A and 27B are views schematically illustrating configuration examples of the biosensor substrate of the first exemplary embodiment when the biosensor substrate has a square outline.

FIG. 27A is a view schematically illustrating a configuration example of biosensor substrate 30 having the square outline. FIG. 27A is a view of biosensor substrate 30 when viewed from the upper surface side. In the configuration example, as illustrated in FIG. 27A, plural linear tracks (pit strings) are formed at equal intervals in biosensor substrate 30. Wells 13 are arranged so as to be arrayed in parallel with the track. Other configurations of biosensor substrate 30 are identical to those of the first exemplary embodiment. When biosensor substrate 30 is cut on line A-A', a sectional structure of biosensor substrate 30 is identical to that in FIG. 1C. Similar to the first exemplary embodiment, the address information is held in the pit string.

In the configuration example, biosensor substrate 30 and objective lens 106 are relatively moved in the direction parallel to the track. At this point, for example, biosensor substrate 30 is fixed, and the optical system including semiconductor laser 101 to aperture 111 and a housing holding holder 121 and objective lens actuator 122 are moved in the direction parallel to the track along the guide shaft. At that time, the focus control and the tracking control are similarly performed to objective lens 106, and the beam spot of the excitation light is moved along one track. When the beam spot moves to the terminal end of the one track, objective lens 106 is moved by a track pitch in the direction perpendicular to the track, and the track jump is performed to the adjacent track. Then, the housing is moved in the direction parallel to the track to scan the adjacent track. When the scanning is performed to the predetermined number of tracks, biosensor substrate 30 is moved in the direction perpendicular to the track such that objective lens 106 returns to a neutral position at the scanning position. Then, the similar operation is repeated to scan all the tracks.

In the configuration example, similar to the first exemplary embodiment, because bottom surface portion 13a of well 13 is located within the focal depth of the excitation light, efficiency of irradiation of the sample with the excitation light can be enhanced, and the sample can accurately be measured.

Figure 27B:
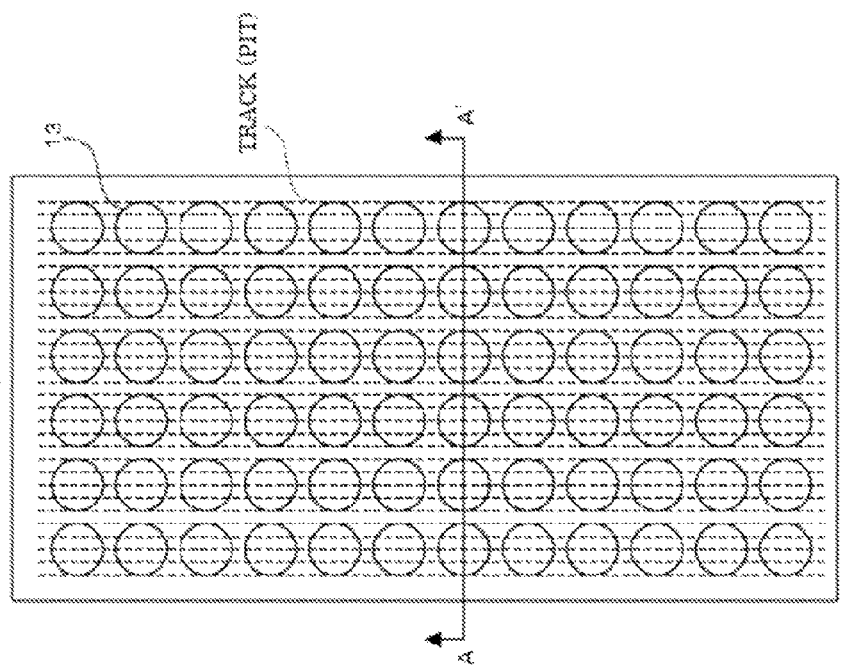

As illustrated in FIG. 27B, the lead-in area may be provided, and the information including distance d3 between bottom surface portion 13a and reflecting surface 11a may be held in the lead-in area similar to the modification. The focal depth of the excitation light may be adjusted using the information.

In the first exemplary embodiment and the first modification, the track is formed by the pit string. Alternatively, the track may be formed by a continuous groove, or the track may be formed by a combination of the pit string and the groove. In the case that the track is formed by the groove, for example, the address information is held by meandering of the groove. That is, a meandering shape of the groove is modulated according to the address information.

Figure 28:
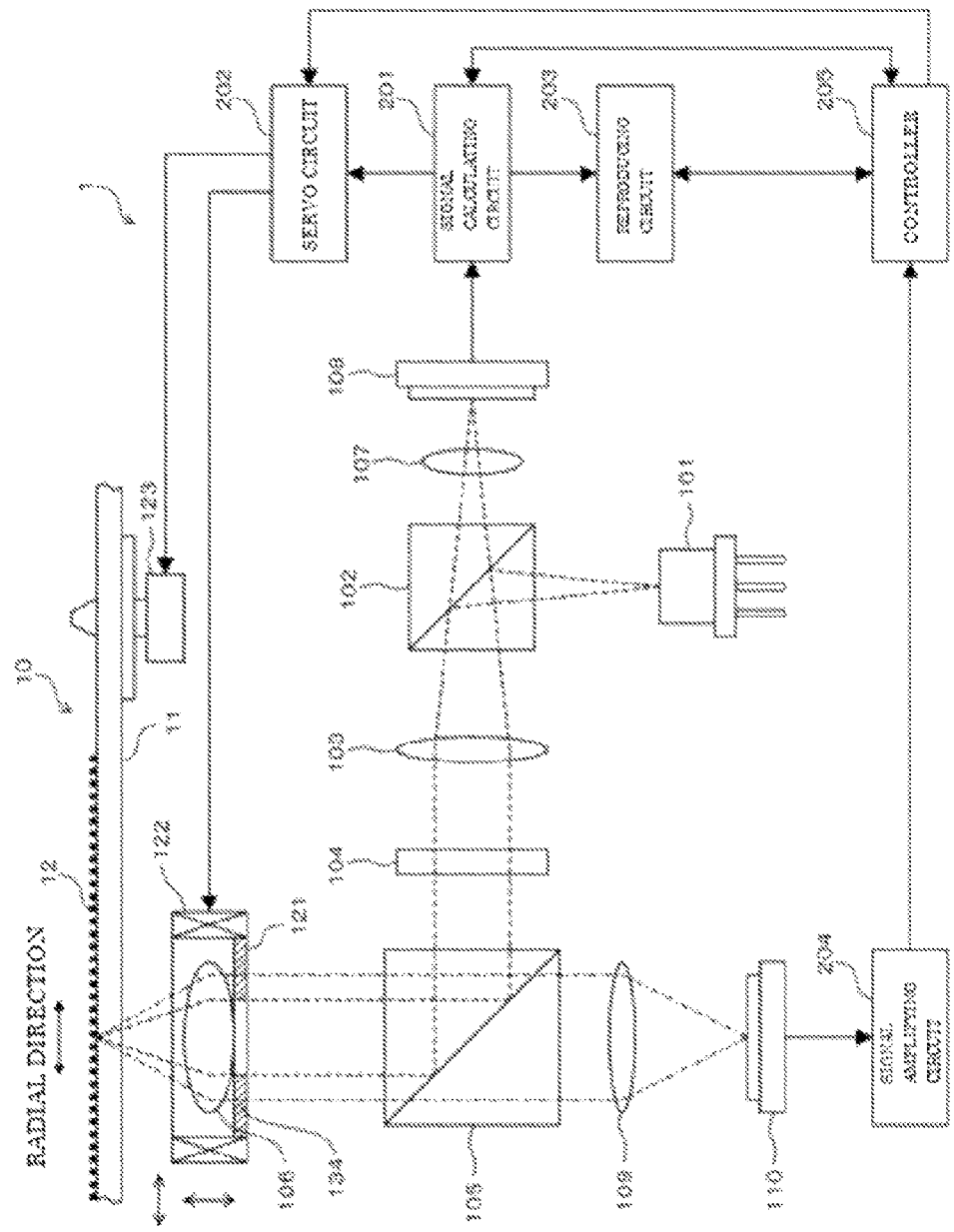
FIG. 28 is a view illustrating another configuration of the fluorescence detection device of the first exemplary embodiment.

In the first exemplary embodiment 1, aperture 111 is provided between semiconductor laser 101 and PBS 102. Alternatively, as illustrated in FIG. 28, aperture 134 that restricts the diameter of the excitation light may be provided on the side of dichroic prism 105 with respect to objective lens 106 so as to be held by holder 121. Aperture 134 has wavelength selectivity, blocks a predetermined peripheral portion for the excitation light, and wholly transmits the fluorescence. FIG. 28 is a view illustrating the case that aperture 134 is used in fluorescence detection device 1 of FIG. 3. In the configuration of fluorescence detection device 2 in FIGS. 7 and 10, aperture 134 may also be provided on the side of dichroic prism 105 with respect to objective lens 106 so as to be held by holder 121.

In this case, the diameter of the excitation light incident on objective lens 106 is decided by aperture 134 similar to the first exemplary embodiment. In this case, even if objective lens 106 is displaced in the tracking direction in the tracking control, because aperture 134 moves integrally with objective lens 106, a flux of the excitation light incident on objective lens 106 is not deviated from the center of objective lens 106. Therefore, as illustrated in FIGS. 3, 7, and 10, an optical characteristic of the excitation light is hardly degraded compared with the use of aperture 111.

Figures 29A, 29B, 29C:
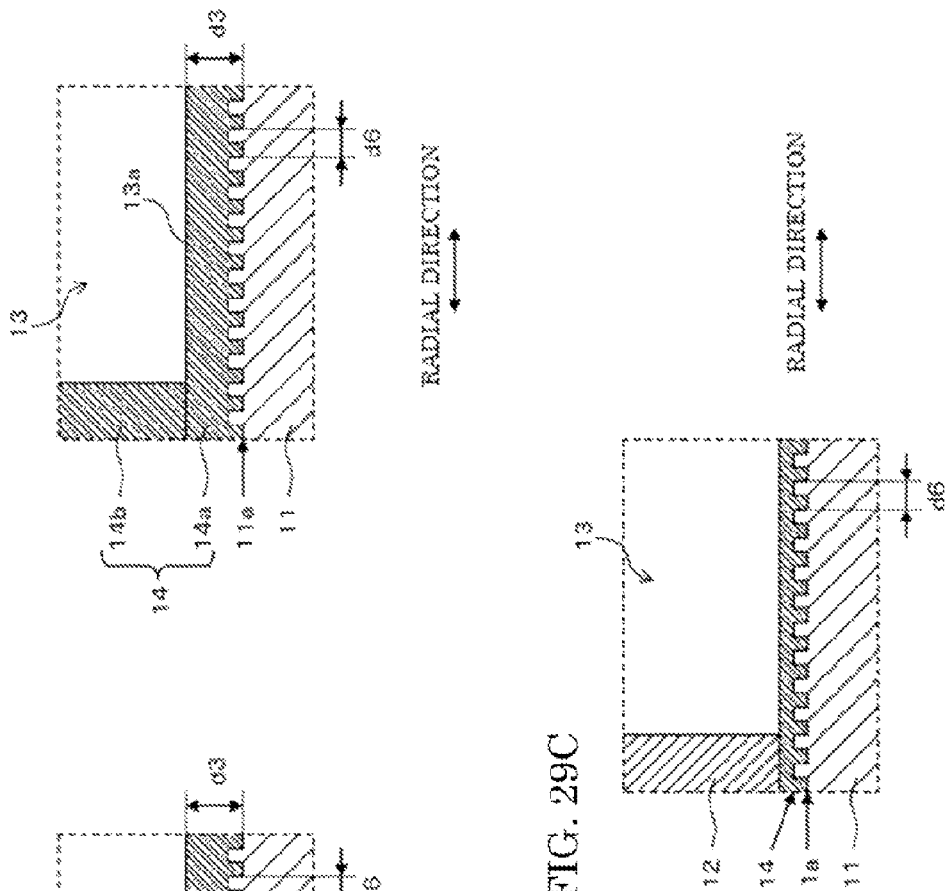
FIGS. 29A to 29C are views illustrating other configuration examples of the well of the second exemplary embodiment.
Figure 31:
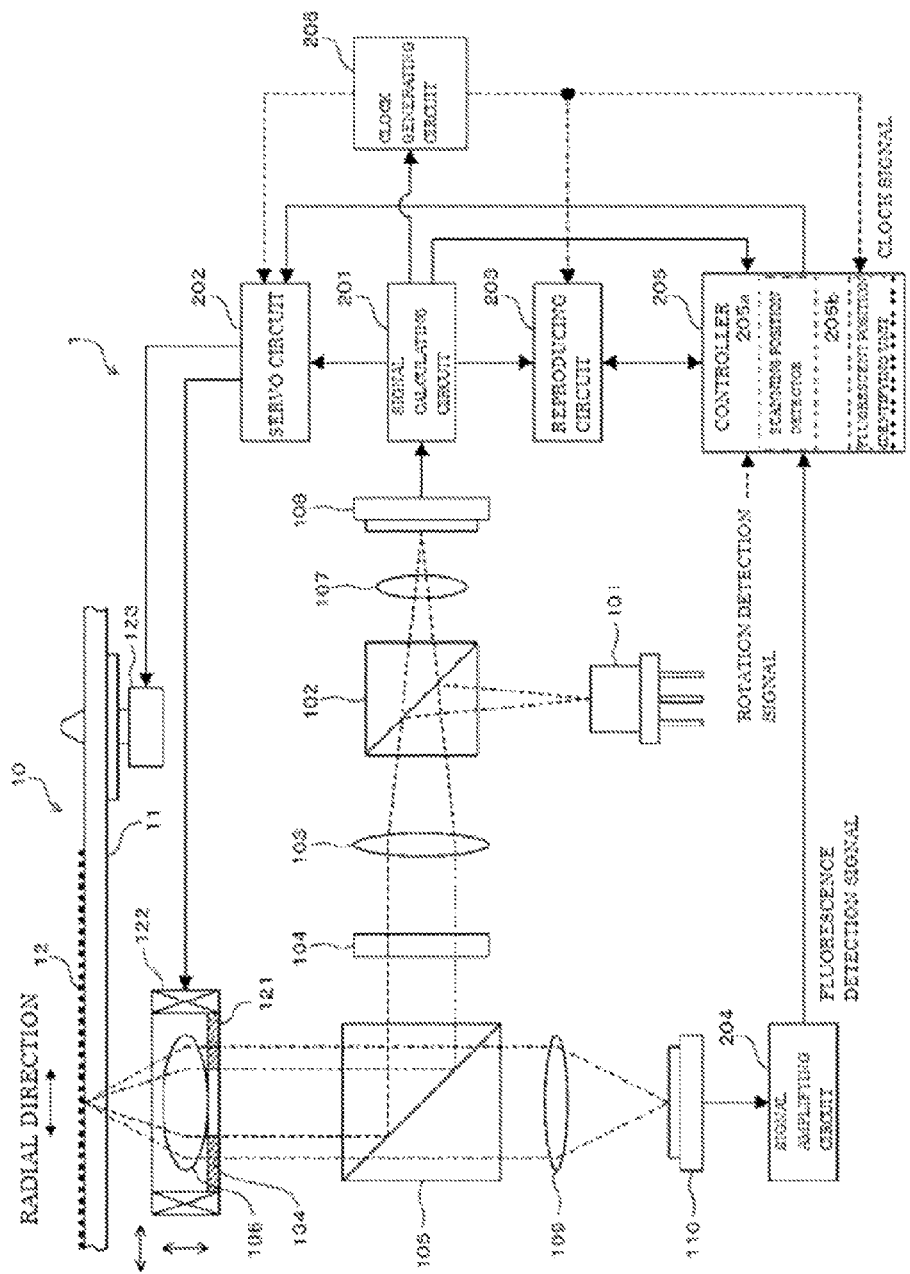
FIG. 31 is a view illustrating another configuration of the fluorescence detection device of the second exemplary embodiment.

In the second exemplary embodiment, well layer 12 is arranged on reflecting film 14. Alternatively, reflecting film 14 may be used as well layer 12. As illustrated in FIG. 29A, plural micro wells 13 may be formed in reflecting film 14 formed on the upper surface of base substrate 11. In this case, a material having a refractive index different from that of base substrate 11 may be used as reflecting film 14, and a resin material having a different refractive index can be used as reflecting film 14. Reflecting film 14 in FIG. 29A may be constructed with bottom layer 14*a* and top layer 14*b* as illustrated in FIG. 29B. In this case, bottom layer 14*a* may differ from top layer 14*b* in a material.

In the second exemplary embodiment, well 13 including bottom surface portion 13*a* is provided in well layer 12 arranged on reflecting film 14. Alternatively, bottom surface portion 13*a* of well 13 may constitute the upper surface of reflecting film 14. As illustrated in FIG. 29C, well 13 may be constructed with a through-hole in well layer 12, and formed on reflecting film 14.

In the second exemplary embodiment, biosensor substrate 10 has the disc shape. Alternatively, biosensor substrate 10 may have a square outline.

FIG. 30A is a view schematically illustrating a configuration example of biosensor substrate 20 having the square outline. FIG. 30A is a view of biosensor substrate 20 when viewed from the upper surface side.

In the configuration example, plural linear tracks (pit strings) are formed at equal intervals in biosensor substrate 20. Wells 13 are arranged so as to be arrayed in parallel with the track. Other configurations of biosensor substrate 20 are identical to those of the second exemplary embodiment. When biosensor substrate 20 is cut on line A-A', a sectional structure of biosensor substrate 20 is identical to that in FIG. 11C. Similar to the second exemplary embodiment, the address information is held in the pit string.

As illustrated in FIG. 30B, for example, the common address area has a square shape, and the common address area is allocated so as to be arrayed along the track. Similar to the second exemplary embodiment, the identical well address is provided to the track portion included in the identical common address area. The physical address applied to the track portion is similar to that in FIG. 14 of the second exemplary embodiment. The track number is held in each track portion together with the well address. The common address area is set wider than well 13. Well 13 is arranged in the substantial center of the common address area.

In the configuration example, biosensor substrate 20 and objective lens 106 are relatively moved in the direction parallel to the track. At this point, for example, biosensor substrate 20 is fixed, and the optical system including semiconductor laser 101 to aperture 111 and a housing holding holder 121 and objective lens actuator 122 are moved in the direction parallel to the track along the guide shaft. At that time, the focus control and the tracking control are similarly performed to objective lens 106, and the beam spot of the excitation light is moved along one track. When the beam spot moves to the terminal end of the one track, objective lens 106 is moved by a track pitch in the direction perpendicular to the track, and the track jump is performed to the adjacent track. Then, the housing is moved in the direction parallel to the track to scan the adjacent track. When the scanning is performed to the predetermined number of tracks, biosensor substrate 20 is moved in the direction perpendicular to the track such that objective lens 106 returns to a neutral position at the scanning position. Then, the similar operation is repeated to scan all the tracks.

In the configuration example, similar to the second exemplary embodiment, the identical well address identifying the position of well 13 is provided to the track portion traversing identical well 13, so that well 13 can be associated with the position of well 13 identified by the well address information on a one-on-one basis.

In the second exemplary embodiment, the track is formed by the pit string. Alternatively, the track may be formed by a continuous groove, or the track may be formed by a combination of the pit string and the groove. In the case that the track is formed by the groove, for example, the address information is held by meandering of the groove. That is, a meandering shape of the groove is modulated according to the address information.

In the second exemplary embodiment, aperture 111 is provided between semiconductor laser 101 and PBS 102. Alternatively, as illustrated in FIG. 32, aperture 134 that restricts the diameter of the excitation light may be provided on the side of dichroic prism 105 with respect to objective lens 106 so as to be held by holder 121. Aperture 134 has wavelength selectivity, blocks a predetermined peripheral portion for the excitation light, and wholly transmits the fluorescence.

In this case, the diameter of the excitation light incident on objective lens 106 is decided by aperture 134 similar to the second exemplary embodiment. In this case, even if objective lens 106 is displaced in the tracking direction in the tracking control, because aperture 134 moves integrally with objective lens 106, a flux of the excitation light incident on objective lens 106 is not deviated from the center of objective lens 106. Therefore, as illustrated in FIG. 17, an optical characteristic of the excitation light is hardly degraded compared with the use of aperture 111.

In the second exemplary embodiment, one semiconductor laser 101 is used as the light source. The present invention can be applied to a fluorescence detection device including an optical system other than the optical system of the second exemplary embodiment and a sample holding carrier having a configuration other than the configuration of the second exemplary embodiment. For example, like PTL 2, the present invention can be applied to a fluorescence detection device in which a light source emitting the excitation light to the well and a light source emitting the laser beam to the track are separately prepared and a sample holding carrier used in the fluorescence detection device.

Additionally, various changes can properly be made in the exemplary embodiments of the present invention within the technical thought of the claims.

The track jump control processing described with reference to FIGS. 21A to 25 can widely be used in not only the case that the common address area is set but also the case that the non-well area having a predetermined width exists in the direction traversing the track. For example, the control concerning the track jump can be extracted as the invention having the wider range, such as those described below.

(1) A fluorescence detection device that irradiates a sample holding carrier holding a fluorescently-labeled sample with irradiation light and detects fluorescence yielded from the sample irradiated with the irradiation light, the sample holding carrier including: a substrate; a track that is formed in an upper surface of the substrate; and plural sample accommodation units that are arranged on an upper surface side of the substrate to accommodate samples, wherein the sample accommodation unit is not arranged in the sample holding carrier in a belt-like area having a predetermined width in a direction perpendicular to the track, the fluorescence detection device includes:

a light source that emits the irradiation light;

an objective lens that causes the irradiation light to converge on the sample holding carrier;

an objective lens actuator that drives the objective lens;

a control unit that controls the objective lens actuator; and a light scanning unit that performs scanning along the track with the irradiation light caused to converge by the objective lens, wherein the control unit controls the objective lens actuator so as to move a position irradiated with the irradiation light in a direction traversing the track, when a scanning position of the irradiation light is included in the belt-like area.

(2) In the fluorescence detection device (1), the control unit acquires the information for skipping the belt-like area, and moves the position irradiated with the irradiation light in the direction traversing the track based on the acquired information.

According to the extracted present invention, the area where the sample accommodation unit is not arranged is skipped, so that the sample holding carrier can rapidly and smoothly be scanned with the irradiation light.

What is claimed is:

1. A sample holding carrier comprising:
   a substrate on which irradiation light is incident from a lower surface;
   a reflecting film that is arranged on an upper surface of the substrate to partially reflect the irradiation light; and
   a plurality of sample accommodation units that are arranged on an upper surface side of the reflecting film and have bottom surfaces,
   wherein the irradiation light is converged to be incident on the substrate, and a distance from a reflecting surface that is of a boundary between the reflecting film and the substrate to the bottom surface of each of the sample accommodation units is less than or equal to a focal depth of the irradiation light.

2. The sample holding carrier according to claim 1, further comprising:
   a track that is formed in the upper surface of the substrate, wherein address information identifying a position on the sample holding carrier is held in the track.

3. The sample holding carrier according to claim 1, wherein a parameter value that is used to derive the focal depth to be applied to the sample holding carrier is stored in the track.

4. A sample holding carrier according to claim 1, further comprising:
   a track that is formed in an upper surface of the substrate to hold predetermined information,
   wherein the track traverses a portion below the sample accommodation units, and identical well address information identifying a position of each of the sample accommodation units is provided to a plurality of track portions traversing the identical sample accommodation unit.

5. The sample holding carrier according to claim 4, wherein a common address area is set along the track and has a size that includes each of the sample accommodation units, the common address area having a width of a predetermined number of tracks in a direction traversing the track and a width of a predetermined track length in a direction along the track,
   each of the sample accommodation units is arranged such that the sample accommodation units are respectively allocated to each of the common address areas, and the identical well address information is provided to each of the track portions included in the identical common address area.

6. The sample holding carrier according to claim 4, wherein, in a group of the track portions to which the identical well address information is provided, track address information distinguishing one track portion from other track portions is provided to each of the track portions.

7. A fluorescence detection system that irradiates a sample holding carrier holding a fluorescently-labeled sample with irradiation light from a fluorescence detection device and detects fluorescence yielded from the sample irradiated with the irradiation light using the fluorescence detection device,
   wherein the sample holding carrier includes:
      a substrate on which the irradiation light is incident from a lower surface;
      a reflecting film that is arranged on an upper surface of the substrate to partially reflect the irradiation light; and
      a plurality of sample accommodation units that are arranged on an upper surface side of the reflecting film and have bottom surfaces,
   the fluorescence detection device includes an optical system that causes the irradiation light to converge to be incident on the substrate, and
   a distance from a reflecting surface that is of a boundary between the reflecting film and the substrate to the bottom surface of each of the sample accommodation units is less than or equal to a focal depth of the irradiation light.

8. The fluorescence detection system according to claim 7, wherein
   the sample holding carrier holds a parameter value that is used to derive the focal depth to be applied to the sample holding carrier, and
   the fluorescence detection device includes:
      a reading unit that reads the parameter value;
      a focal depth adjusting unit that changes the focal depth of the irradiation light; and
      a control unit that controls the focal depth adjusting unit so as to obtain the focal depth corresponding to the parameter value read by the reading unit.

9. A fluorescence detection device that irradiates a sample holding carrier holding a fluorescently-labeled sample with irradiation light and detects fluorescence yielded from the sample irradiated with the irradiation light,
   the sample holding carrier including: a substrate on which the irradiation light is incident from a lower surface; a track that is formed in an upper surface of the substrate; a reflecting film that is arranged on the upper surface of the substrate to partially reflect the irradiation light; and a plurality of sample accommodation units that are arranged on an upper surface side of the reflecting film and have bottom surfaces,
   the fluorescence detection device comprising:
      a light source that emits the irradiation light;
      an objective lens that causes the irradiation light to converge on the sample holding carrier;
      an objective lens actuator that drives the objective lens in at least a focus direction parallel to an optical axis and a tracking direction perpendicular to the track;
      a separation element that introduces the irradiation light emitted from the light source to the objective lens and separates the fluorescence from the irradiation light reflected by the sample holding carrier;
      a photodetector that receives the irradiation light, which is reflected by the sample holding carrier and separated from the fluorescence by the separation element, and outputs a signal in order to generate a focus error signal and a tracking error signal;
      a control unit that controls the objective lens actuator based on the focus error signal and the tracking error signal;
      a fluorescence detector that receives the fluorescence separated by the separation element; and
      a light scanning unit that changes a relative position between the objective lens and the sample holding carrier such that the irradiation light moves on the sample holding carrier along the track, wherein a distance from a reflecting surface that is of a boundary between the reflecting film and the substrate to the bottom surface of each of the sample accommodation units is less than or equal to a focal depth of the irradiation light.

10. The fluorescence detection device according to claim 9, wherein the sample holding carrier holds a parameter value that is used to derive the focal depth to be applied to the sample holding carrier, the fluorescence detection device further comprising:

a reading unit that reads the parameter value;

a focal depth adjusting unit that changes the focal depth of the irradiation light; and a focal depth control unit that controls the focal depth adjusting unit so as to obtain the focal depth corresponding to the parameter value read by the reading unit.

11. A fluorescence detection device according to claim 9, wherein the sample holding carrier holds predetermined information in the track, the track traverses a portion below the sample accommodation units, identical well address information identifying a position of each of the sample accommodation units is provided to a plurality of track portions traversing the identical sample accommodation unit, the fluorescence detection device further comprising:

a reproducing unit that reproduces the well address information from output from the photodetector; and a scanning position detector that detects a scanning position of the irradiation light on each of the track portions.

12. The fluorescence detection device according to claim 11, wherein, in a group of the track portions to which the identical well address information is provided, track address information distinguishing one track portion from other track portions is provided to each of the track portions, and the reproducing unit further reproduces the track address information based on the output from the photodetector, the fluorescence detection device further including a fluorescent position identifying unit that identifies a position where fluorescence is yielded on the sample holding carrier by associating the well address information reproduced by the reproducing unit and the track address information with the scanning position detected by the scanning position detector based on the output from the photodetector.

13. The fluorescence detection device according to claim 11, further comprising:

an objective lens actuator that drives the objective lens and a control unit that controls the objective lens actuator, wherein each of the sample accommodation units is not arranged in the sample holding carrier in a belt-like area having a predetermined width in a direction perpendicular to the track, and the control unit controls the objective lens actuator so as to move a position irradiated with the irradiation light in a direction traversing the track, when a scanning position of the irradiation light is included in the belt-like area.

* * * * *